(12) United States Patent
Schoonover et al.

(10) Patent No.: US 10,799,178 B2
(45) Date of Patent: Oct. 13, 2020

(54) VIRTUAL BURROW ASSAY FOR A DIVERSITY OF NEUROLOGICAL AND PSYCHIATRIC DISORDERS

(71) Applicants: Carl E. Schoonover, New York, NY (US); Andrew J. P. Fink, New York, NY (US); Richard Axel, New York, NY (US)

(72) Inventors: Carl E. Schoonover, New York, NY (US); Andrew J. P. Fink, New York, NY (US); Richard Axel, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 16/149,310

(22) Filed: Oct. 2, 2018

(65) Prior Publication Data
US 2019/0133521 A1    May 9, 2019

Related U.S. Application Data

(60) Provisional application No. 62/566,948, filed on Oct. 2, 2017.

(51) Int. Cl.
| | |
|---|---|
| *A61B 5/00* | (2006.01) |
| *A61K 49/00* | (2006.01) |
| *A61D 3/00* | (2006.01) |
| *A61B 5/16* | (2006.01) |
| *A61B 5/11* | (2006.01) |

(52) U.S. Cl.
CPC .............. *A61B 5/4884* (2013.01); *A61B 5/11* (2013.01); *A61B 5/1105* (2013.01); *A61B 5/16* (2013.01); *A61D 3/00* (2013.01); *A61K 49/0008* (2013.01); *A61B 2503/40* (2013.01); *A61B 2503/42* (2013.01); *A61D 2003/003* (2013.01)

(58) Field of Classification Search
CPC ....... A61B 5/4884; A61B 5/11; A61B 5/1105; A61B 2503/40; A61B 2503/42; A61D 3/00
USPC ...................................................... 340/573.1
See application file for complete search history.

(56) References Cited

U.S. PATENT DOCUMENTS

| | | | | |
|---|---|---|---|---|
| 3,739,751 A | * | 6/1973 | Mohr ................. | A61D 3/00 119/752 |
| 5,357,905 A | * | 10/1994 | Gordon .............. | A01K 15/027 119/708 |
| 7,086,350 B2 | | 8/2006 | Tecott | |
| 7,269,516 B2 | | 9/2007 | Brunner et al. | |

(Continued)

OTHER PUBLICATIONS

Alexandrov et al., Highthroughtput analysis of behavior of drug discovery, European Journal of Pharmacology, vol. 753, pp. 127-134, Jul. 2014.

(Continued)

*Primary Examiner* — John A Tweel, Jr.
(74) *Attorney, Agent, or Firm* — John P. White; Paul Teng; Cooper & Dunham LLP

(57) ABSTRACT

Methods and apparatuses are provided for a virtual burrow assay for a diversity of neurological and psychiatric disorders. For example, a virtual burrow array device including a virtual, burrow, a linear actuator and one or more sensors is provided.

20 Claims, 36 Drawing Sheets
(28 of 36 Drawing Sheet(s) Filed in Color)

(56) References Cited

U.S. PATENT DOCUMENTS

| | | | |
|---|---|---|---|
| 8,590,487 B1* | 11/2013 | Goddard, Jr. | A01K 1/031 |
| | | | 119/417 |
| 9,317,743 B2 | 4/2016 | Datta et al. | |
| 9,497,939 B2 | 11/2016 | Castranova | |
| 2017/0000081 A1 | 1/2017 | Betts-Lacroix et al. | |
| 2017/0251629 A1* | 9/2017 | Hickman-Miller | |
| | | | A01K 15/029 |
| 2019/0261597 A1* | 8/2019 | Tabachnik | A01K 1/031 |

OTHER PUBLICATIONS

Bouton et al., Conditioned fear assessed by freezing and by the suppression of three different baselines, Animal Learning & Behavior, 8(3), pp. 429-434, 1980.

Cianca et al., A Robotics-Based Behavioral Paradigm to Measure Anxiety-Related Responses in Zebrafish, PLOS One, vol. 8, issue 7, pp. 1-11, Jul. 2013.

Franceschi et al., Vision Guides Selection of Freeze or Flight Defense Strategies in Mice, Current Biology 26, pp. 2150-2154, Aug. 22, 2016.

Domenici et al., The Kinematics and Performance of the Escape Response in the Angelfish (*Pterophyllum eimekei*), Journal of Experimental Biology, 1991, pp. 187-205.

Hanell et al., Structured evaluation of rodent behavioral tests used in drug discovery research, Frontiers in Behavioral Neuroscience, Jul. 22, 2014.

Kim et al., A Simple Behavioral Paradigm to Measure Impulsive Behavior in an Animal Model of Attention Deficit Hyperactivity Disorder (ADHD) of the Spontaneously Hypertensive Rats, Biomolecules & Therapeutics, vol. 20, issue 1, pp. 125-131, Jan. 2012.

Komada et al., Elevated Plus Maze for Mice, Journal of Visualized Experiments, pp. 1-4, 2008.

Yilmaz et al., "Rapid Innate Defensive Responses of Mice to Looming Visual Stimuli", Current Biology 23, pp. 2011-2015, 2013.

Walf et al., The use of the elevated plus maze as an assay of anxiety-related behavior related behavior in rodents, Nature Publishing Group, pp. 1-15, 2007.

Stoelting: any-box [online] [retrieved on Jan. 25, 2019]. [retrieved on Jan. 25, 2019] Retrieved from the Internet: <URL: www.stoeltingco.com/anymaze/mazes/anxiety-depression/any-box.html>.

Med Associates Inc.: Elevated Plus Maze w/IR Beam Detection Package for Mouse [online] [retrieved on Jan. 25, 2019]. Retrieved from the Internet: URL:www.med-associates.com/product/elevated-plus-maze-pkg-with-ir-beam-detection-for-mouse/.

Futek: Model LSB200: Jr. Miniature S-Beam Load Cell, Sensor Solution[online] [retrieved on Jan. 25, 2019]. Retrieved from the Internet:<URL:www.futek.com/files/pdf/Product%20Drawings/lab200.pdf>.

Maze Engineers: Light Dark Box A Test of Anxiety, [online] [retrieved on Jan. 25, 2019]. Retrieved from the Internet::<URL:https://mazeengineers.com/portfolio/light-dark-box/>.

Actimetrics: LimeLight: Video tracking for Open Field—Plus Maze—Radial Arm Maze—Zero Maze—Novel Object Recognition—Conditioned Place Preference, [online] [retrieved on Jan. 25, 2019]. Retrieved from the Internet:<URL:www.actimetrics.com/products/limelight/>.

Firgelli Technologies Inc.: Miniature Linear Motion Series, [online] [retrieved on Jan. 25, 2019]. Retrieved from the Internet: <URL:www.trossenrobotics.com/shared/productdocs/L12_datasheet.pdf>.

New Way® Air Bushings [online] [retrieved on Jan. 25, 2019]. Retrieved from the Internet:<URL: www.newwayairbearings.com/catalog/air-bushings/>.

Panlab: Four Plate box—Aron test, [online] [retrieved on Jan. 25, 2019]. Retrieved from the Internet: <URL:https://www.panlab.com/en/products/four-plate-box-aron-test-panlab.

Panlab: Open Field box—for motor performance, learning and anxiety [online] [retrieved on Jan. 25, 2019]. Retrieved from the Internet:<URL:www.panlab.com/en/products/open-field-box-panlab.

Psychogenics: NeuroCube® [online] [retrieved on Jan. 25, 2019]. Retrieved from the Internet:<URL: www.psychogenics.com/ neurocube.html>.

Psychogenics: SmartCube® [online] [retrieved on Jan. 25, 2019]. Retrieved from the Internet:<URL: www.psychogenics.com/ smartcube.html>.

Vium: The Digital Vivarium®, [online] [retrieved on Jan. 25, 2019]. Retrieved from the Internet:<URL: https://www.vium.com/the-digital-vivarium/>.

Ennaceur et al., A new one-trail test for neurobiological studies of memory in rats. 1: Behavioral data, Behavioral Brain Research, vol. 31, pp. 47-59, 1998.

Bolles et al., The effect of predictive cues on freezing in rats, Animal Learning & Behavior, vol. 4 (1A), pp. 6-8 (1976).

Hofer, Cardiac and Respiratory Function During Sudden Prolonged Immobility in Wild Rodents, Psychosomatic Medicine, Vo. 32, No. 6 (Nov. 1970).

Cooke et al., Visual recognition memory, manifest as long-term habituation, requires synaptic plasticity in V1, Nat. Neurosci, vol. 18, Issue 2, pp. 262-271, (2015).

Davis, The Mammalian Startle Response, Neutral Mechanism of Startle Behavior, pp. 287-288, (1984).

Thompson et al., Habituation: a model phenomenon for the study of neuronal substances of behavior, Psychological Review, vol. 73, No. 1, pp. 16-43, (1966).

Gershman et al., Novelty and Inductive Generalization in Human Reinforcement Learning, Cognitive Science Society, vol. 7, pp. 391-415, (2015).

Roitman et al., Response of Neurons in the Lateral Intraparietal Area during Combined Visual Discrimination Reaction Time Task, The Journal of Neuroscience, vol. 22 (21), pp. 9475-9489, (2002).

Schoonover et al., A naturalistic assay for measuring behavioral responses to aversive stimuli at millisecond timescale, Department of Neuroscience and Howard Hughes Medical Institute, BioRxiv (2017).

Uexkull, A stroll through the worlds of animals and men: A picture book of invisible worlds, Semiotica, vol. 89-4, pp. 319-391, (1992).

Root, The participation of cortical amygdala in innate, odor-driven behavior, Nature, vol. 515(7526), pp. 269-273 (2014).

* cited by examiner

Standard measures of learned aversion

Time spent freezing

Rogan et al, 1997

Lick suppression

Table 1
Median Latencies in Seconds: Experiment 1

| Group | Session | | |
|---|---|---|---|
| | Last Training | Test 1 | Test 2 |
| | First Lick Latency | | |
| S | 25.3 | 309.5 | 206.9 |

Mahoney and Ayres, 1976

Place avoidance

Yan et al., 2008

Prior Art

Typlt ... Schmid Front Integr Neurosci. (2013)

VIRTUAL BURROW ASSAY FOR A DIVERSITY OF NEUROLOGICAL AND PSYCHIATRIC DISORDERS

This application claims the benefit of U.S. Provisional 62/566,948, filed Oct. 2, 2017, the contents of which are hereby incorporated by reference in its entirety.

All publications and other references mentioned herein are incorporated by reference in their entirety, as if each individual publication or reference were specifically and individually indicated to be incorporated by reference. Publications and references cited herein are not admitted to be prior art.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND

Traditional assays of aversive Pavlovian conditioning measure behavioral responses/phenomena that extend over many seconds, such as time spent freezing (FIG. 13) during a specified epoch (Bouton and Bolles, 1980) or conditioned suppression (Estes and Skinner, 1941). These slowly evolving behaviors are difficult to relate to the neuronal events that govern them, which unfold on a timescale of milliseconds. The flight from danger, in contrast, is a stereotyped behavioral motif whose onset consists of a rapid transition in behavioral state (Blanchard et al., 1998; De Franceschi et al., 2016; Domenici and Blake, 1991; Walther, 1969; Yilmaz and Meister, 2013). Mice, for example, initiate flight within 250 msec of the presentation of a looming visual stimulus (De Franceschi et al., 2016; Yilmaz and Meister, 2013). In the wild, mice poised at the threshold of its burrow must evaluate whether it is safe to exit, or whether a perceived threat warrants hasty retreat to the safety of the burrow (Birke et al., 1985; Blanchard and Blanchard, 2008; Blanchard and Blanchard, 1989).

Commonly employed rodent behavioral assays for anxiety include the elevated plus maze, the open field test, and the light-dark box test. Despite enthusiasm for NK1 antagonists in the late 1990s/early 2000s, based in part on observing good activity in traditional assays such as the elevated plus maze, the open field test and the light-dark box test, these compounds failed to show activity in clinical trials. The poor predictive power of these assays is one of the reasons why many large pharmaceutical companies have moved out of this area. Traditional assays measure the activity of anxiolytic agents by introducing the animal into an innately aversive context (e.g. exposure to a predatory threat overhead), thereby inducing anxiety-like behavior (e.g. avoidance of the exposed location). However, the circuit mechanisms that regulate anxiety may not be related to the circuits that mediate defensive responses to external predatory threats (e.g. Humans who suffer from anxiety do not require stressors, much less predatory threat—to experience anxious thoughts or exhibit anxiety related behavior). Therefore, modulation of defensive responses to predatory threat by a pharmacological agent may not be predictive of activity of this agent on internally-generated anxiety.

Moreover, such traditional assays depend on voluntary exploration of a complex, aversive environment by the animal, and measure location preference over a period of several minutes. Another drawback of traditional assays is that animals habituate to the aversive context; this renders it challenging to test an animal multiple times, and to perform longitudinal studies over time (e.g. to measure the efficacy of SSRIs that typically take several weeks to reach peak activity).

Deficits in motor performance are symptoms of Parkinson's disease (PD; resting tremor, rigidity, akinesia, bradykinesia and postural instability), Huntington's disease (HD; involuntary jerking or writhing movements (chorea), tremors, muscle problems, such as rigidity or muscle contracture (dystonia), impaired gait, posture and balance), Essential tremor (tremor), Attention-deficit/hyperactivity disorder (fidget). Transient tic disorder/Tourette's syndrome (muscle twitch), Dyskinesias (chorea, tics, diminished voluntary movement, and involuntary muscle movements), Dystonia (uncontrolled movements), Muscular Dystrophy (MD; weakness), Amyotrophic lateral sclerosis (ALS; weakness); Ataxia (impaired balance, impaired coordination), Multiple Sclerosis (MS; balance, involuntary movements, weakness, overactive reflexes), Traumatic brain injury (TBI; balance), and Stroke (general loss of coordination). A hallmark of Parkinson's disease is a reduced ability to initiate voluntary movement. Standard assays of motor deficits, which are primarily focused on locomotion or other alternating limb movements such as swimming or rotarod, and simple measures of locomotion (e.g. beam interruptions during open field activity) present interpretation challenges. More specific assays of akinesia in rodents (e.g. rotarod, grid test) similarly assay only movement related to locomotion and because they are difficult for the animal to perform, require some form of training—thus engaging neural systems unrelated to those implicated in Parkinson's disease (PD). Moreover, the fact that these tasks require skilled movement rather than movement that is typical for the organism [many animals fail to complete the minimum requirements of the task (e.g. time spent on the rod/grid) and must be excluded from analysis] hinder interpretability and validity with respect to the typical movement disorders in human PD patients. On the other hand, humans suffering from PD show deficits in voluntary movement initiation for even mundane actions such as standing up or walking.

Learned helplessness (the sense of powerlessness arising from persistent failure to succeed) is a symptom of Depression. A commonly employed model of learned helplessness in the rodent consists in exposing animals to repeated and uncontrollable electric shocks, then re-exposing them to these same painful stimuli in the presence of an easy escape route. Rodents typically fail to initiate escape, or do so at long latencies (i.e. submit to the shocks rather than escaping). Interpretation of this assay (which is considered one of the well validated models of depression) is confounded by the fact that the neural systems that are engaged by pain, fear and freezing—which are likely to play an important role in this behavior—may be only tangentially related to the neural system(s) that is/are responsible for depression. The other two most commonly employed assays for depression are the forced swim test and the tail suspension test, which rely on the threat of drowning and inescapable suspension by the tail, respectively (both measure the time at which the animals become immobile, appearing to 'give up'). Although physical and psychological forms of torture are also known to cause depression in human, these contingencies constitute special cases and should not be employed as the basis for modeling depression in rodents.

Sensory deficits (detection, discrimination), in particular olfactory deficits, are an early indicator of the onset of Alzheimer's disease (AD), Parkinson's disease (PD) and Huntington's disease (HD). The best existing assays for measuring olfactory deficits in rodent models rely upon instrumental (a.k.a. operant) conditioning in which the animal is trained to produce a specific motor action, such as a lever press to indicate detection or left/right choice for discrimination, of a given odorant. This kind of paradigm relies upon two neural systems (those required for cognition and motor learning) that are unrelated to the sensory system that is being assayed. In addition to injecting unnecessary complexity, and therefore noise in the behavioral measurement, any impairment in cognitive or motor function (which are present in AD, PD, and HD) risks affecting the animal's performance independent of any sensory deficit.

Memory deficits are symptoms of Alzheimer's disease (AD), Parkinson's disease (PD), and cognitive decline associated with aging. Traditional rodent behavioral models for memory deficits (e.g. Morris water maze, Pavlovian (a.k.a. classical) and instrumental conditioning) require motivating the animal using threat or reward. For example in the Morris water maze task a rodent is forced to swim around a large pool until it locates a hidden dry platform; memory is assayed by measuring how long the animal takes to locate the platform during subsequent introductions into the maze. The paradigm motivates the animal by threatening its survival (it will drown unless it finds the platform) in order to produce an interpretable behavior (latency to finding the platform). In addition to engaging neural systems required for encoding and retrieving memories, the Morris water maze task likely engages neural systems that are unrelated to memory (e.g. emotion, motivation, survival, swimming). This introduces significant confounds; for instance diazepam, an anxiolytic, impairs performance in the Morris water maze but it remains unclear whether this is due to it having an effect on emotional state or on the encoding of memories (or on the interaction between the two neural systems that regulate these processes). Other traditional paradigms for assaying memory similarly rely upon unrelated neural systems (e.g. pain, hunger, thirst, feeding, drinking, execution of learned motor skills such as lever pressing), injecting unnecessary complexity and potential confounds.

Neophobia (the extreme or irrational fear or dislike of anything novel or unfamiliar) is a hallmark of both Schizophrenia and Autism spectrum disorder (ASD). Since assays of neophobia (such as the open field test) typically rely on the animal's propensity to explore a potentially threatening environment, they do not permit disambiguation between fear of predators, and aversion to novelty. Additionally, the oddball paradigm (in which presentations of sequences of repetitive stimuli are infrequently interrupted by a deviant stimulus), which is commonly employed to assess schizophrenia and ASD patients has no analog in the rodent for lack of a clear behavior indicating detection of an oddball stimulus.

There is unmet need for a rodent behavior model that is predictive of a diverse set of neurological/psychiatric disorders including anxiety, depression, motor deficits, sensory deficits and cognitive deficits.

BRIEF SUMMARY

This application describes apparatuses and methods for a virtual burrow assay (VBA) to detect behavioral responses of animals (e.g., head-fixed rodents) to stimuli.

In an aspect of this disclosure, a virtual burrow assay device is provided for detecting behavioral responses of an animal which typically inhabits a burrow based on the animal entering (ingress) or exiting (egress) a virtual burrow, and such device includes a virtual burrow configured to slide along an anterior-posterior axis of the animal; a head stabilizer to which the head of the animal is fixed, the head-fixed animal being permitted to egress (exit from) out of and ingress (enter into) into the virtual burrow; a port for delivering stimuli and/or rewards that is coupled to the virtual burrow, the animal being required to egress in order to approach and/or investigate the source of the stimulus and/or reward; a linear actuator which is coupled to the virtual burrow and configured to be adjustably retracted to an egress position along an axis of movement of the virtual burrow and to be advanced to an ingress position along the axis of movement of the virtual burrow; a position sensor to detect a position of the virtual burrow and a force sensor to detect a force exerted by the animal against the linear actuator, when the linear actuator is in the egress position; and a controller to cause, based on the position detected by the position sensor and the force detected by the force sensor, the linear actuator to be advanced from the retracted egress position to the ingress position in which the animal is in control of the position of the virtual burrow.

In another aspect of this disclosure, the linear actuator is coupled to the virtual burrow via a tether that is disposed to be slackened when the linear actuator is advanced to the ingress position to free the animal to ingress, and the force sensor detects the force exerted by the animal against the linear actuator when the animal pulls on the tether.

In another aspect of this disclosure, a method of detecting behavioral responses of an animal based on the animal entering (ingress) or exiting (egress) a virtual burrow, to using a virtual burrow assay device including a virtual burrow, a head stabilizer, a controller, a linear actuator, a position sensor and a force sensor is provided, and such method includes sliding the virtual burrow along an anterior-posterior axis of the animal, the animal being head-fixed to a head stabilizer and being permitted to egress out of and ingress into the virtual burrow; delivering stimuli and/or rewards via a port that is coupled to the virtual burrow, the animal being required to egress in order to approach and/or investigate the source of the stimulus and/or reward; adjustably retracting, by the controller, the linear actuator which is coupled to the virtual burrow to an egress position along an axis of movement of the virtual burrow and advancing the linear actuator to an ingress position along the axis of movement of the virtual burrow; detecting, via the position sensor, a position of the virtual burrow and detecting, via the force sensor, a force exerted by the animal against the linear actuator, when the linear actuator is in the egress position; and causing, by the controller and based on the position detected by the position sensor and the force detected by the force sensor, the linear actuator to be advanced from the retracted egress position to the ingress position in which the animal is in control of the position of the virtual burrow.

In another aspect of this disclosure, a method of testing whether (i) administering a pre-defined compound, or (ii) otherwise manipulating neuronal physiology of the animal (e.g., using optogenetic, chemogenetic or behavioral interventions), has an ameliorative effect on response of an animal is provided which comprises subjecting the animal to the above method of detecting behavioral responses of the animal, both with and without (i) administering the compound to the animal or (ii) otherwise manipulating the neuronal physiology of the animal, and determining the behavior response of the animal.

BRIEF DESCRIPTION OF THE DRAWINGS

The patent or application file contains at least one drawing executed in color. Copies of the patent or patent application publication, based on this application, with color drawing(s) will be provided by the Office upon request and payment of the necessary fee.

FIG. 1A (second from right) shows a head-fixed mouse exiting (egress) and FIG. 1A (far right) shows a head-fixed mouse entering (ingress) the virtual burrow.

FIG. 2B (Right) shows ingress response from a single animal to 15 air puffs at high temporal resolution

DETAILED DESCRIPTION

Figure 1A:
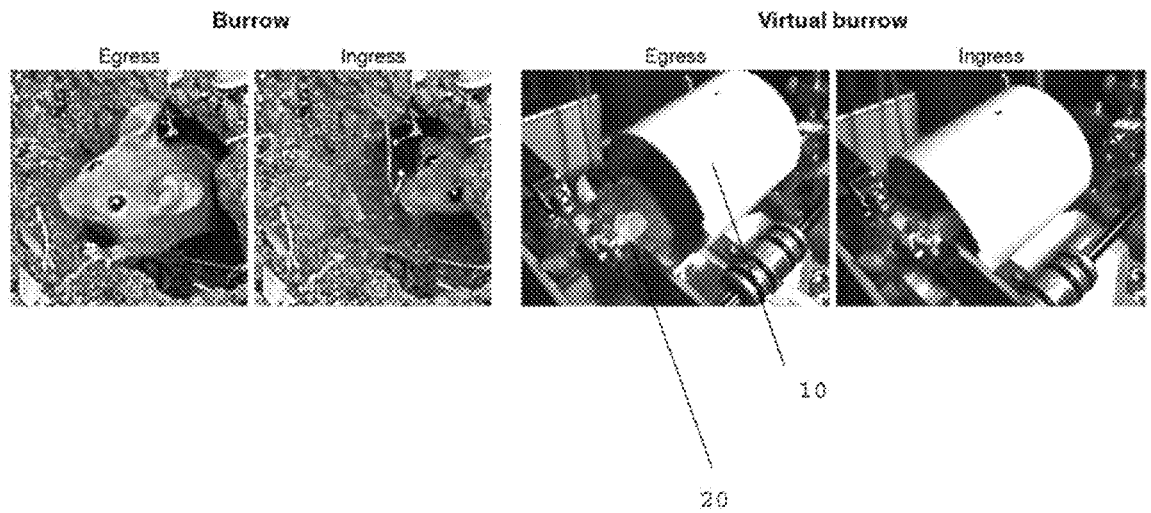
FIG. 1A (far left) shows a mouse in the wild exiting (egress) and FIG. 1A (second from left) shows a mouse entering (ingress) its burrow.
Figure 15A:
FIG. 15A shows a burrow in the wild.
Figure 15B:
FIG. 15B shows an animal poised to leave the burrow.

The following exemplary embodiments and experimental details sections are set forth to aid in an understanding of the subject matter of this disclosure but are not intended to, and should not be construed to, limit in any way the invention applicants claim, FIG. 1A (far left) and FIG. 15b shows a mouse in the wild exiting (egress) and FIG. 1A (second from left) shows a mouse entering (ingress) its burrow (FIG. 15a) (stills courtesy of Misterduncan, YouTube, Mar. 25, 2009). The Virtual Burrow Assay (VBA) device 1 simulates the scenario in which a mouse, poised at the threshold of its burrow, continuously evaluates whether to remain exposed to potential threats outside or to retreat inside an enclosure, as shown in FIG. 1A (second from right) in which a head-fixed animal (e.g., a rodent such as a mouse) is exiting (egress) the virtual burrow 10 and as shown in FIG. 1A (far right) in which the virtual mouse is entering (ingress) the virtual burrow 10. The VBA device 1 recapitulates in the laboratory the behavioral contingencies of a mouse poised at the threshold of its burrow, and it suitable for measuring novelty detection as well as aversion to both conditioned and innately aversive cues. When presented with aversive stimuli, mice exhibit a stereotyped retreat whose onset is determined by measuring the position of a moveable burrow. This withdrawal, which requires no training, is characterized by an abrupt transition that unfolds within milliseconds—a timescale the same as or similar to that of neuronal dynamics, permitting direct comparison between the two. This advantageously allows the behavior of the mouse to be monitored as brain activity unfolds, since the same temporal scale is involved as between the nervous system and the detected behavioral response. The assay is compatible with standard electrophysiological and optical methods for measuring and perturbing neuronal activity. The capacity to precisely measure the onset of behavioral responses to aversive cues would permit comparison of transitions in behavioral state and transitions in neuronal activity.

The VBA device 1 is not limited to measurement of behavioral responses to aversive stimuli, but rather can be used for measurement of a wide variety of behaviors (innate and learned), of positive (e.g., a food odor) stimuli and/or rewarding stimuli (e.g., food or water), neutral stimuli and negative stimuli, as well as socially relevant stimuli (e.g., pheromones or alarm calls). Head-fixing the animal permits sensitive neural recording and perturbation modalities, constrains behavior, permits easier interpretation and reduces variability (less possible behavioral outputs), while still providing naturalistic contingencies. Further, by tapping into innate behaviors (ingress, egress) rather than relying on trained behaviors, in order to probe even sophisticated cognitive functions such as long-term memory, the virtual burrow assay device 1 reduces the layers between observable behavior and the mental function/disfunction to be studied.

More generally, the use of innate behaviors to probe basic sensory and cognitive functions may reduce the number of layers of neural processing that separate the relevant computations and observable behavior. An operant sensory discrimination task, for instance, engages a diversity of circuits, such as those required for signaling reward, regulating satiety/motivation, learning the structure of the task, or learning, planning and executing new motor actions—circuits that may not be related to the circuits implementing the cognitive process under study, but whose tight integration with them may lead to difficulty in the interpretation of behavior, concomitant neural activity, and targeted perturbations. Moreover, key features of motor function—including balance, tremor, chorea, limb and core strength, movement initiation, and movement velocity—can be precisely measured by tracking the position of the burrow and the force exerted against, for example, a tether 40.

Figure 1B:
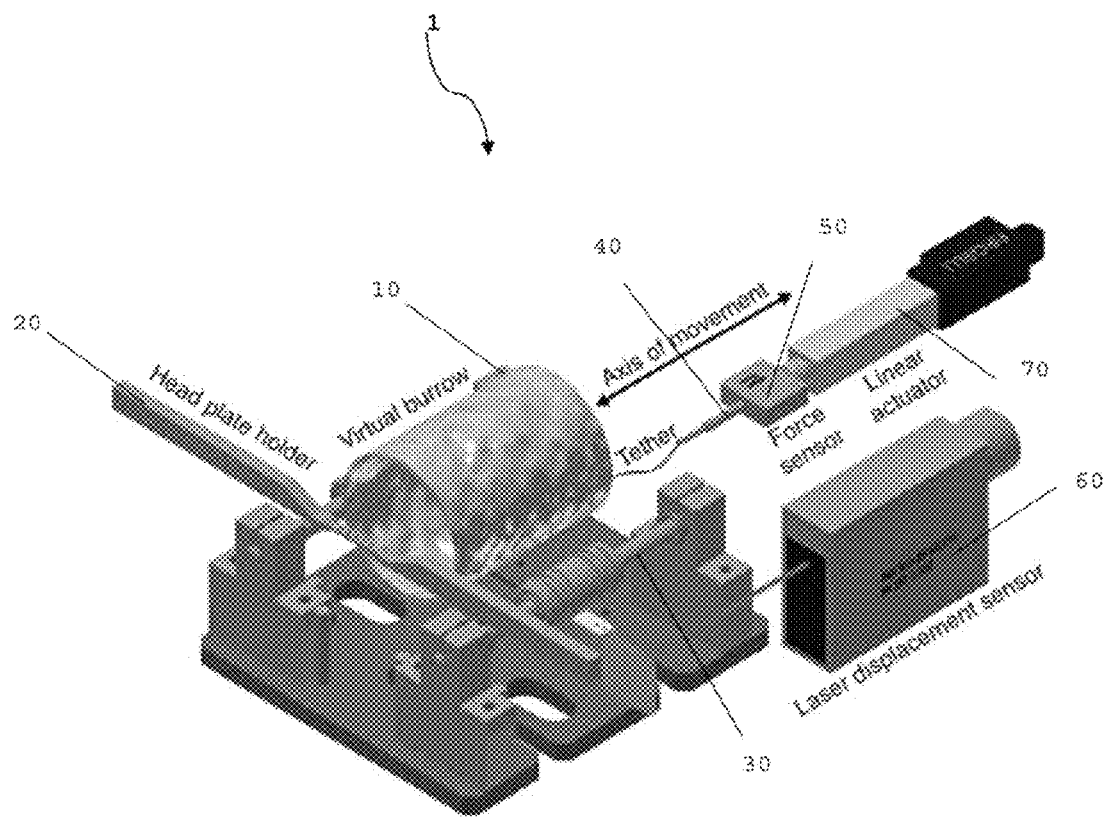
FIG. 1B shows schematically a virtual burrow assay device.
Figure 14:
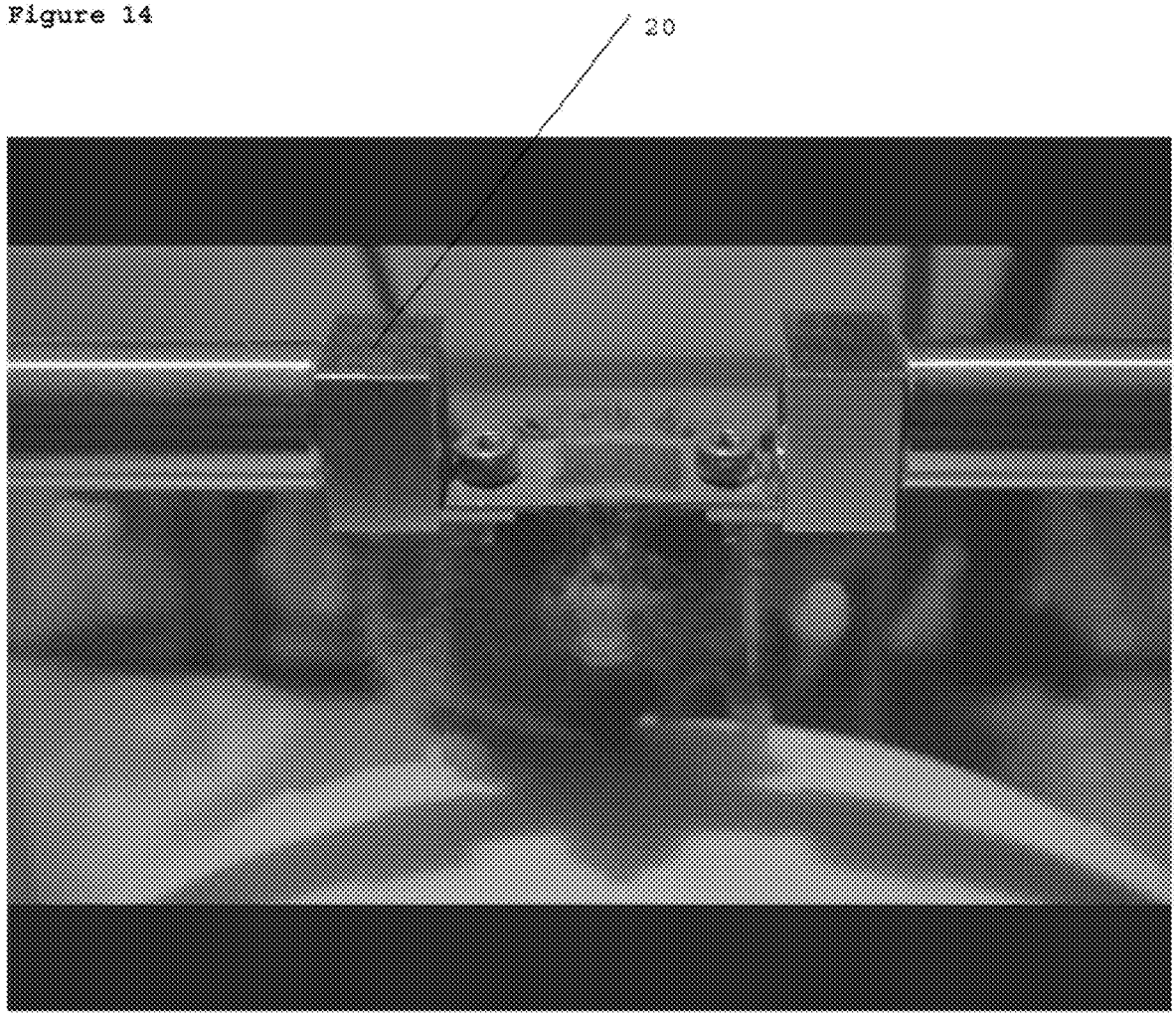
FIG. 14 shows a head-fixed animal.
Figure 16A:
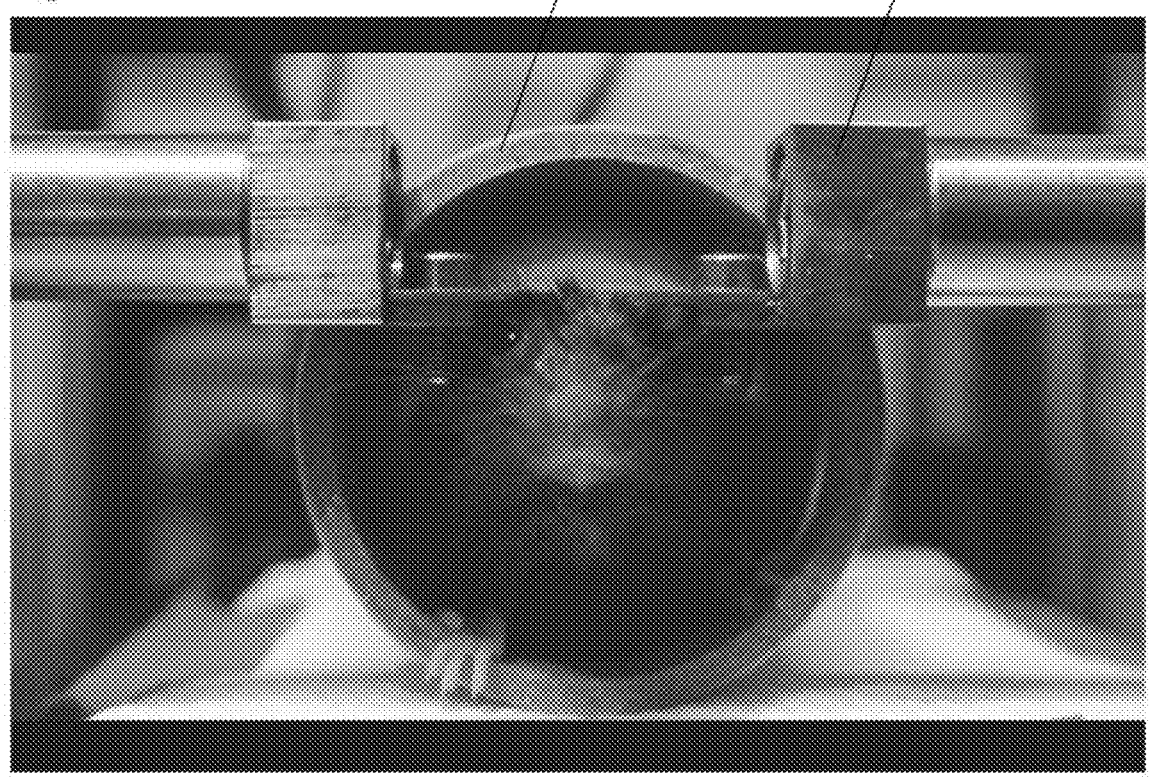
FIGS. 16A and 16B shows a head-fixed animal in the virtual burrow.
Figure 16B:
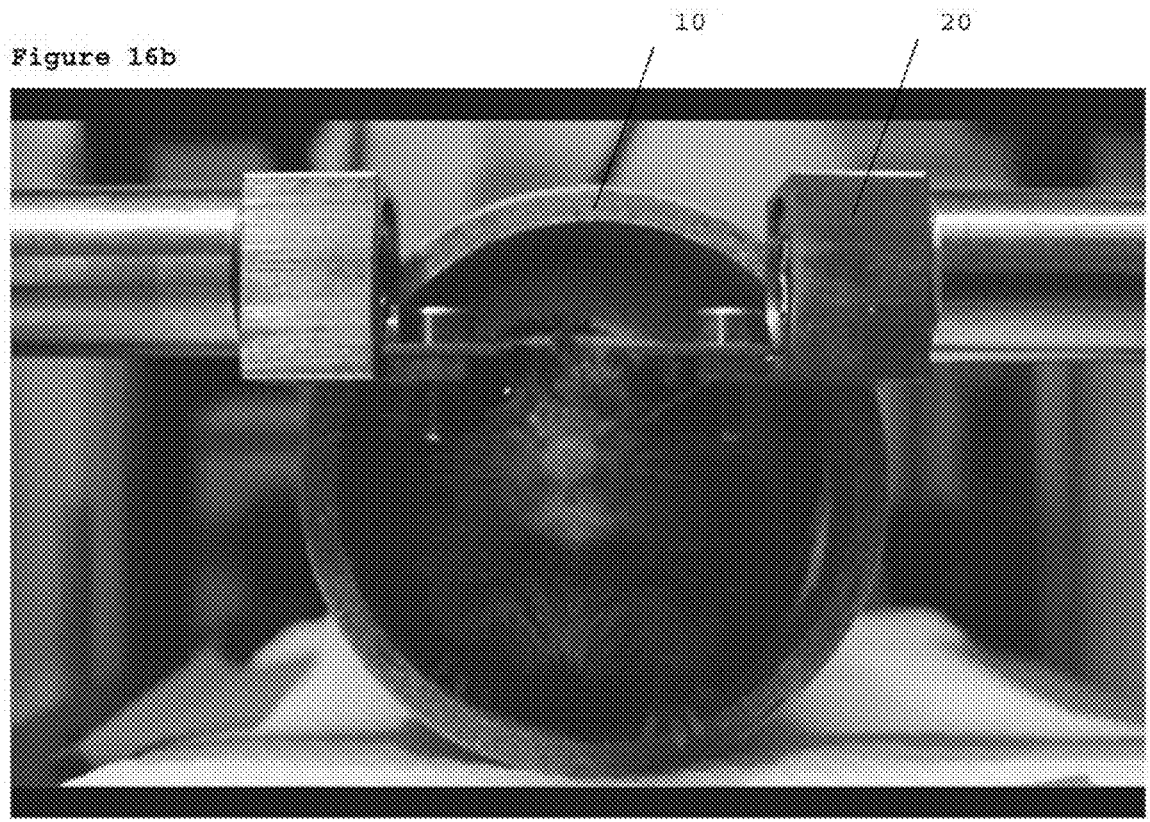
Figure 17:
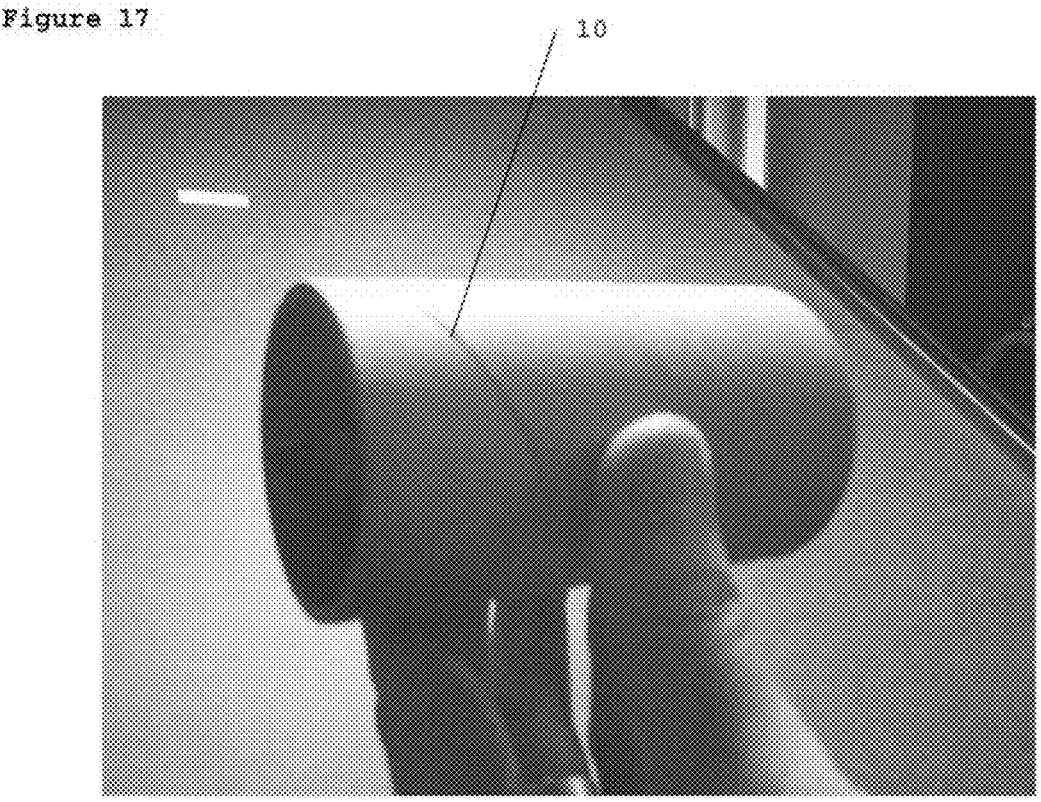
FIG. 17 shows an example of a virtual burrow.
Figure 18:
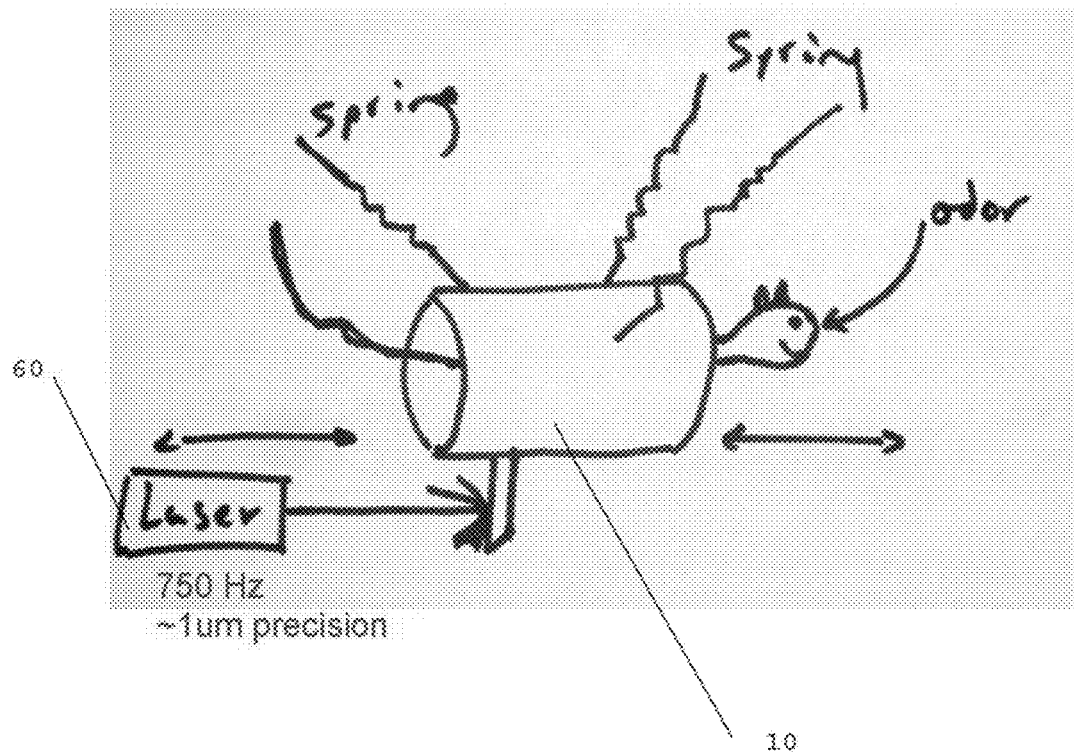
FIG. 18 shows a diagram of the virtual burrow assay.
Figure 19A:
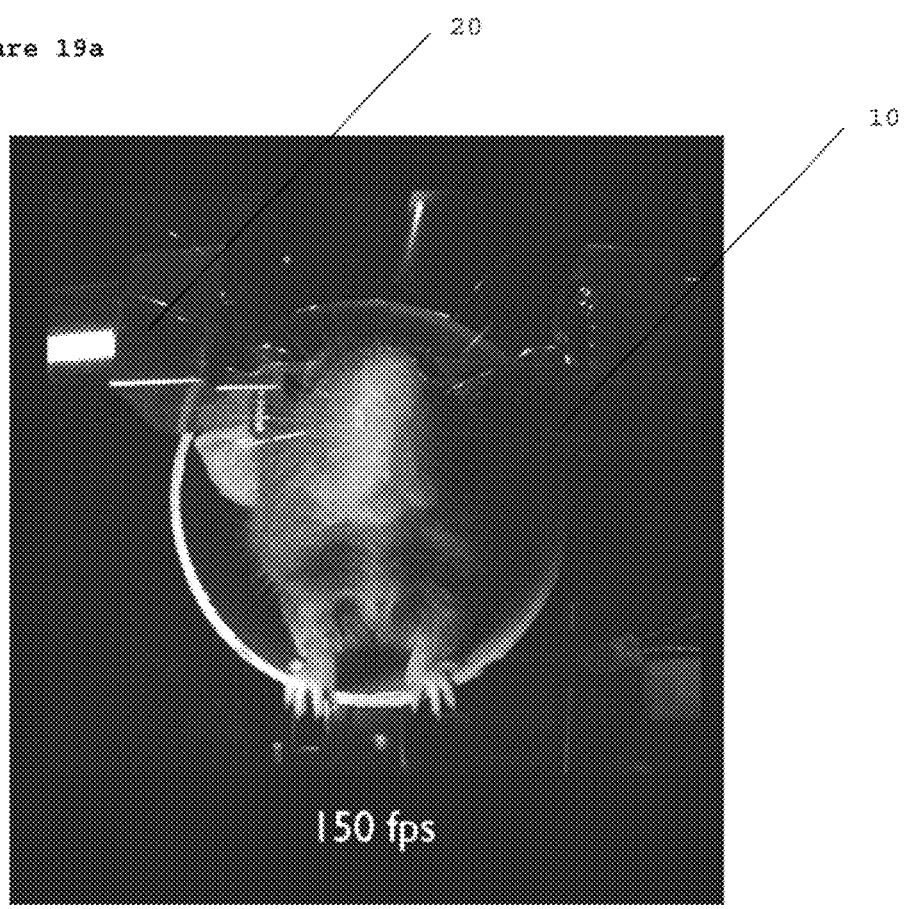
FIG. 19a shows a mouse in the virtual burrow.
Figure 19B:
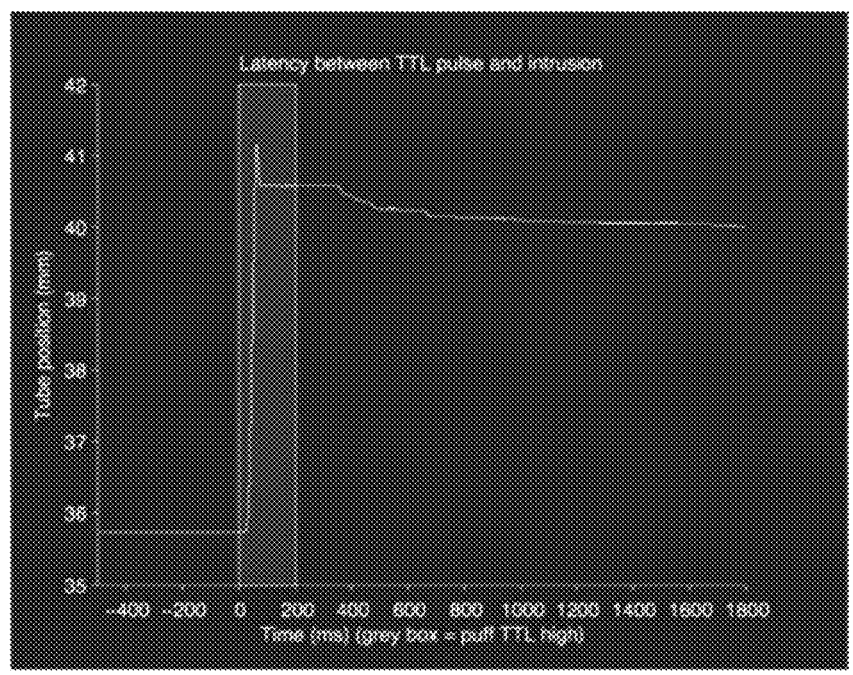
FIG. 19b shows latency between the TTL pulse and intrusion.
Figure 20:
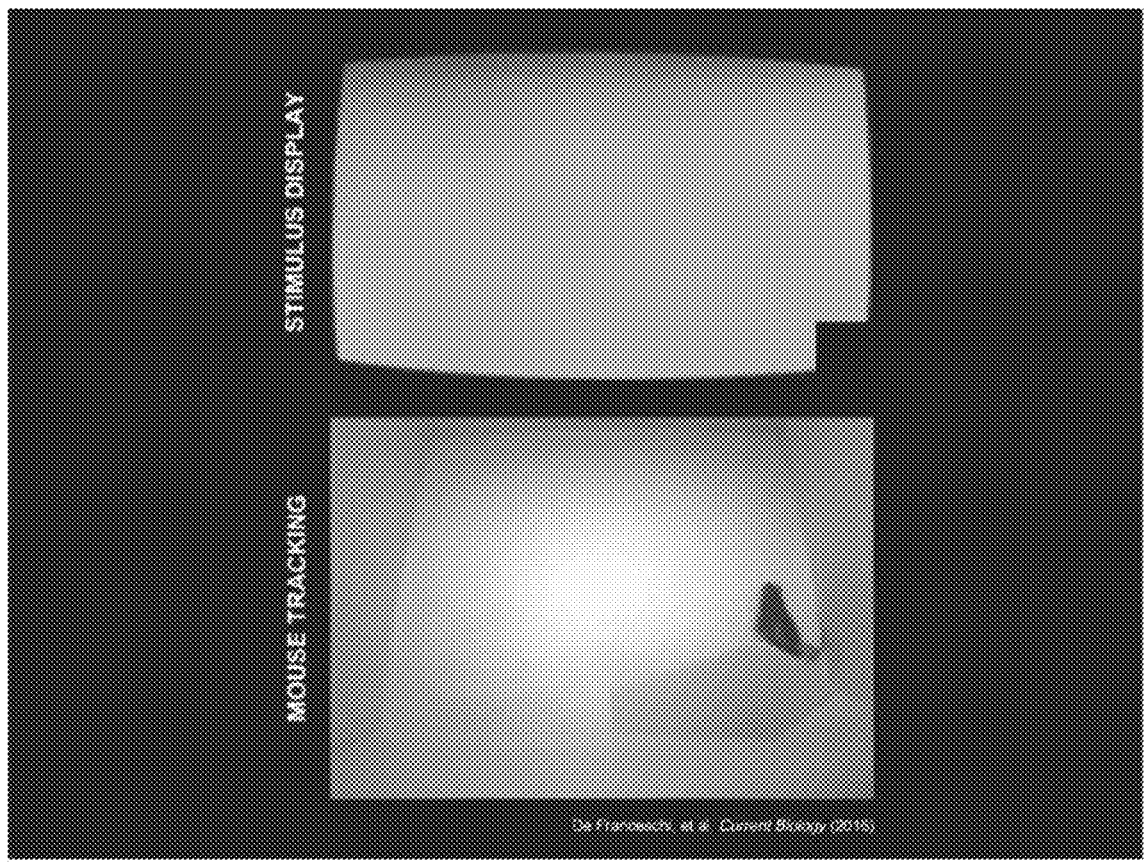
FIG. 20 shows a standard approach for a stimulus display, and a mouse tracking display.
Figure 21A:
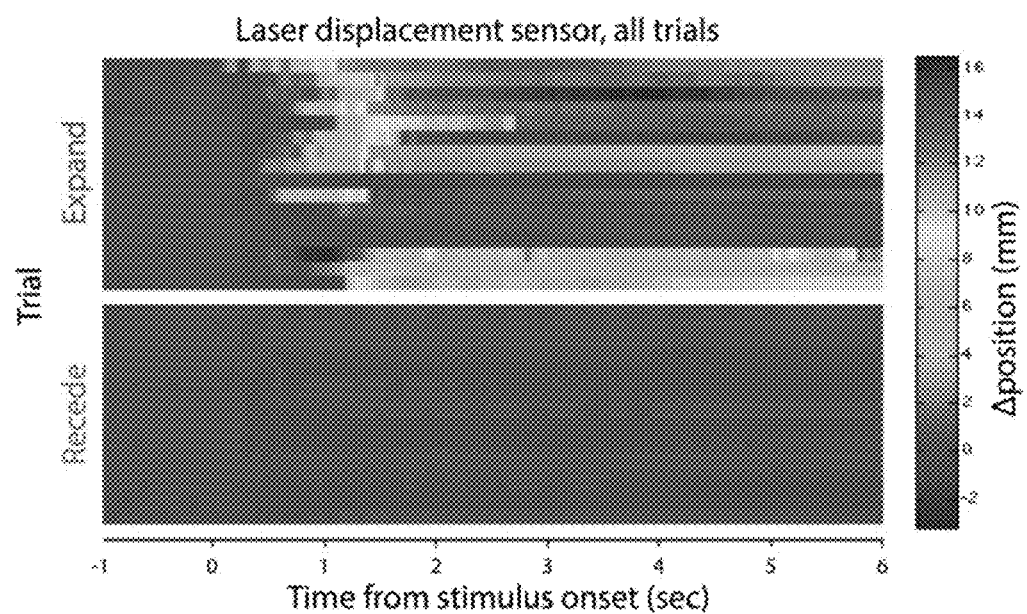
FIG. 21a shows laser displacement sensor data for all trials.
Figure 21B:
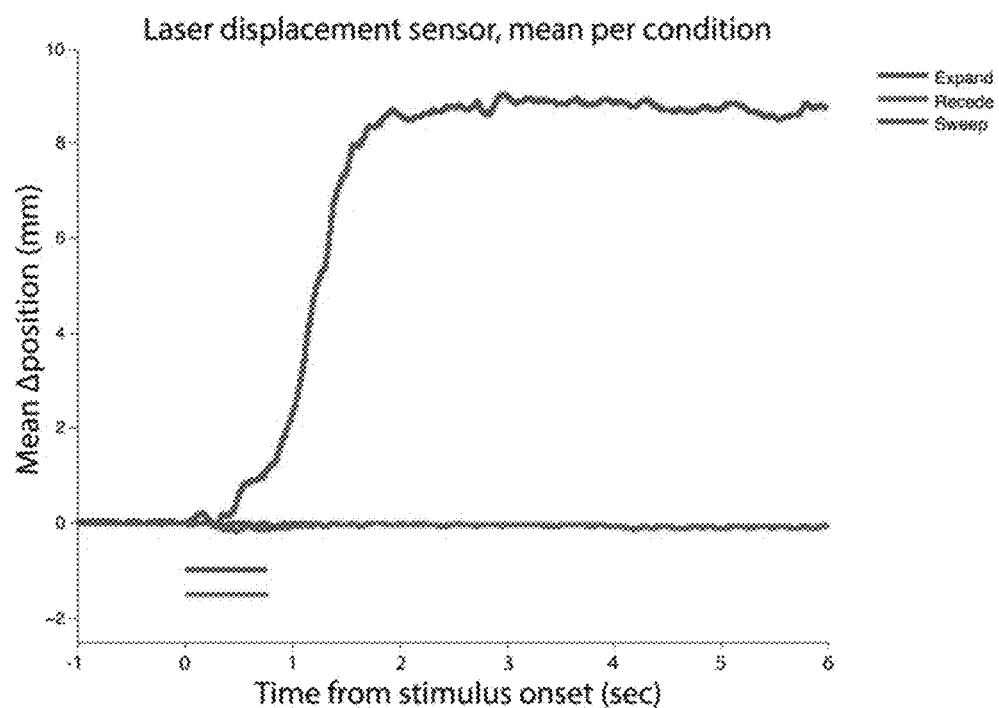
FIG. 21b shows laser displacement sensor data, mean per condition.

FIG. 1B (and FIG. 18) shows schematically a virtual burrow assay device 1 that detects the temporally precise onset of responses to aversive stimuli by exploiting a rapid and stereotyped motor sequence. In the virtual burrow assay device 1, the mouse is preferably head-fixed and secured to a head-plate holder 20 (FIGS. 14, 16a and 16b), and stands inside a virtual burrow 10 (e.g., a cardboard or 3D-printed tube enclosure, as shown in FIG. 17). The head plate holder may be made of metal and come in from the side of or from above the virtual burrow 10. The virtual burrow 10 may be constrained to slide back and forth along the anterior-posterior axis of the body of a head-fixed mouse. The virtual burrow assay device 1 may further comprise a linear actuator 70 which can retract the burrow along a single axis of movement via a tether 40, and the virtual burrow 10 may be constrained by a pair of near-frictionless or low friction air bearings 30 that slide along two precision oriented rails, parallel to the anterior-posterior axis of the animal's body. The mass of the tube and bearing system may be, for example, comparable to the weight of an adult mouse (~30 g). A sensor, such as a laser displacement sensor 60, measures burrow position (FIGS. 21a and 21b), and another sensor, such as a force sensor 50, measures the force generated by the animal when pulling via the tether 40 against the linear actuator 70 (Rendering courtesy of Tanya Tabachnik, Advanced Instrumentation, Zukerman Min Brain Behavior Institute). The analog voltage signals from the laser displacement sensor 60 and the force meter 50 may be acquired and digitized by a data processing device.

Figure 1C:
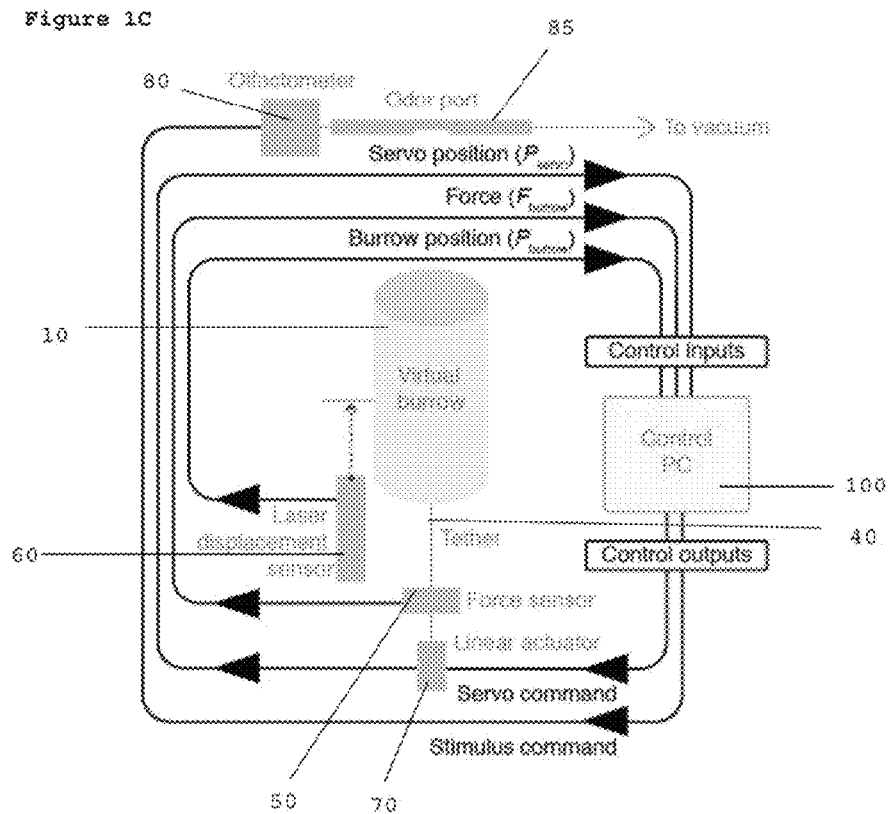
FIG. 1C shows a schematic of a control system for the virtual burrow assay.

FIG. 1C shows a schematic of a control system controlling the virtual burrow assay device 1 (control inputs and outputs are depicted in black, and devices are depicted in grey) including a controller or control PC 100. The controller 100 can be a microcontroller, a circuit, or an integrated box where the controller executes programs of instructions stored in a non-transitory computer readable medium. During an inter-trial interval (ITI), the linear actuator 70 retracts the burrow to the egress position. Once the animal's initial resistance subsides, as measured by the force sensor 50, the linear actuator 70 advances, slackening the tether 40 and freeing the animal to ingress. Trial initiation occurs once the animal has freely maintained the egress position for a predetermined time period (e.g., at least 10 sec). In the event of premature ingress, the trial is aborted and the linear actuator 70 retracts. An olfactometer 80 may deliver the odor to the animal via odor port 85.

Figure 1D:
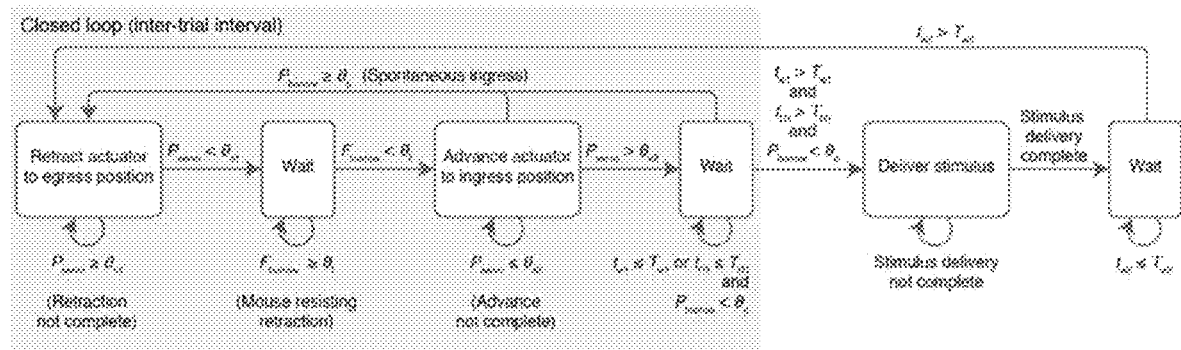
FIG. 1D shows a finite state machine diagram of the virtual burrow assay.

FIG. 1D shows a finite state machine diagram of the virtual burrow assay. During the inter-trial interval (ITI) the burrow may be retracted to the egress position by the linear actuator 70 ("Retract actuator to egress position"). The retraction may be considered complete once the position of the servo motor ($P_{servo}$) of the linear actuator is less than a specified retraction position ($\theta_{s1}$). As long as the force against the tether 40 ($F_{burrow}$) exceeds a preset threshold ($\theta_f$), the linear actuator remains in the retracted position ("Wait"). Once $F_{burrow} < \theta_1$, the linear actuator 70 advances to the ingress position ("Advance actuator to ingress position"), slackening the tether 40. Once $P_{servo}$ reaches the slacked position ($\theta_{s2}$), the system waits ("Wait"). If at any point the position of the burrow ($P_{burrow}$) exceeds a specified threshold ($\theta_p$) the burrow is again retracted and the system returns to an initial state. If, however, the animal remains in the egress position and $P_{burrow} < (\theta_p)$ for a duration ($t_{ITI}$) exceeding both the ITI ($T_{ITI}$) and an enforced delay ($T_{w1}$) following advance of the linear actuator 70 to the ingress position ($t_{w1}$), then the ITI concludes and a stimulus is delivered ("Deliver stimulus"). Throughout the period of stimulus delivery, the linear actuator 70 remains in the advanced position with the animal in complete control of burrow position. Following stimulus delivery ($t_{w2}$), once a second delay period ($T_{w2}$) has elapsed, the system returns to the initial state and the linear actuator 70 retracts the burrow.

When placed inside the virtual burrow 10, mice invariably attempt to enter the tube as far as possible, pulling it to an "ingress" position, where they remain during an initial acclimation period. In preparation for each trial, a tether 40 pulls the tube away from the body to an "egress" position, forcing the animal to exit the burrow. After initially resisting the retraction of the burrow, mice eventually maintain this exposed, egress position voluntarily. The tether 40 is then slackened to permit free ingress and stimuli are presented while the mouse is in full control of the position of the virtual burrow 10 (FIG. 1D). The assay measures the position of the burrow on a millisecond timescale and detects the precise timing of the transition from egress (FIG. 1A, second from right) to ingress (FIG. 1A, far right).

Prior to testing, naïve mice may be head-fixed in the VBA device 1 and given a predetermined amount of time (5-10 mn) to acclimate to the contingencies in open loop (free movement of the burrow). Applicant found that, without exception, mice maintained the burrow in the ingress position throughout this habituation period. Then the mice become acclimated to the closed loop regime, and after an initial period of sustained struggle to maintain the burrow in the ingress position, mice cease resisting and eventually consent to holding the burrow in the egress position even after the linear actuator 70 has advanced, slackening the tether 40 and granting the mouse control over the burrow. The duration of the closed-loop acclimation period varied across mice (5-20 mn). Trial blocks may begin once the animal reliably holds the burrow in the egress position for >30 sec between spontaneous ingresses. Trial initiation may be delayed until after the mouse has held the burrow in the egress position with minimal movement for several seconds so as to ensure that the animal is in a comparable behavioral state prior to each trial.

Figure 2A:
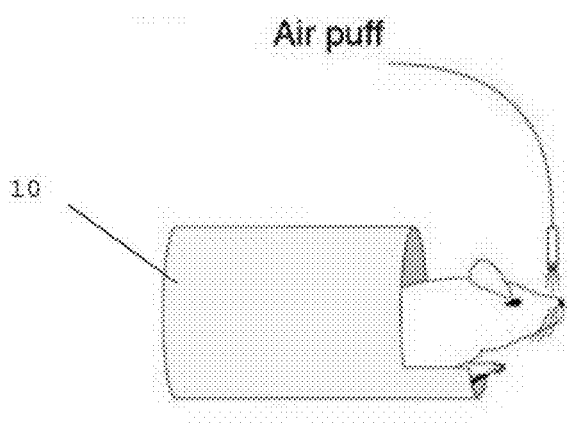
FIG. 2A shows a diagram of experimental set up of the virtual burrow assay.
Figure 2B:
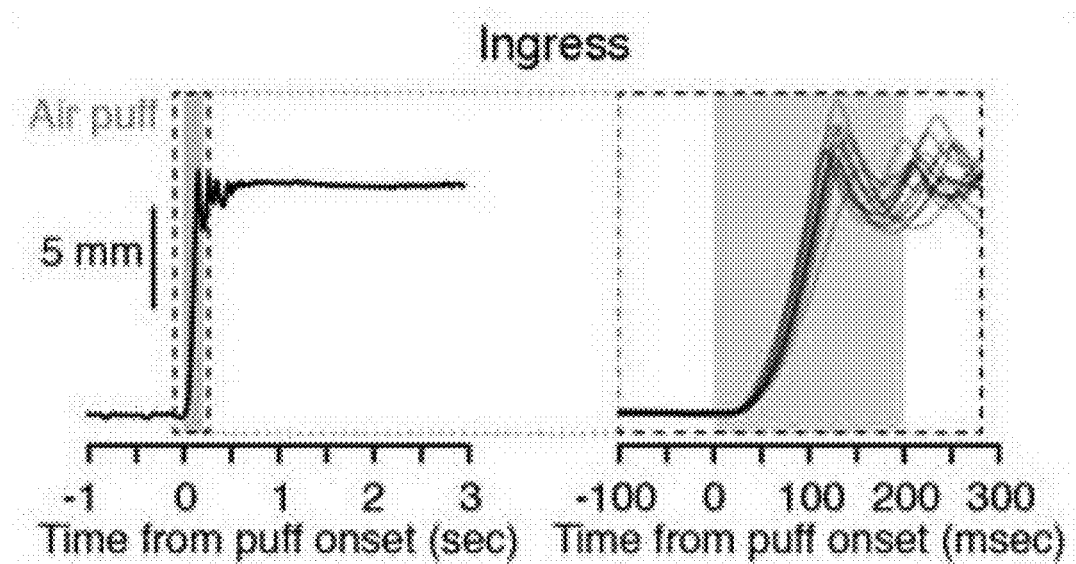
FIG. 2B (left) shows a burrow position as a function of time showing a single ingress in response to a strong air puff.
Figure 2C:
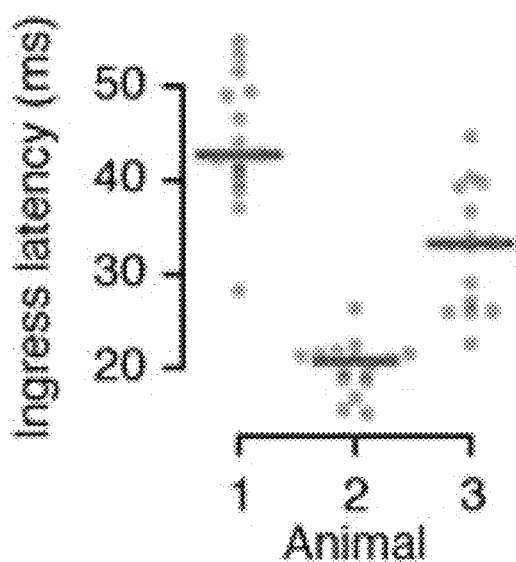
FIG. 2C shows latency to ingress onset in three animals.

FIG. 2A shows a diagram of an experimental set up. With the mouse head-fixed within the virtual burrow 10, an air puff stimulus may be delivered to the nose. Applicant first determined whether an innately aversive stimulus, such as air puff, induces ingress, and if so, the degree to which this response is stereotyped and rapid. Strong air puff delivered to the snout (80 PSI, 2-mm distance) elicited short latency, rapid ingress in all mice tested on all trials (n=3 mice, 15 trials per mouse) (FIGS. 2B, 2C). Animals generated this behavior by pulling the burrow up to the ingress position in a coordinated, simultaneous movement of their fore- and hind-limbs.

FIG. 2B (left) shows a burrow position as a function of time, showing a single ingress in response to a strong air puff (grey box, 200 msec, 80 psi). Upward deflections correspond to burrow movement towards the animal's body (ingress), downward deflections correspond to burrow movement away from the animal's body (egress), and upward going, high-amplitude, sustained deflection corresponds to ingress following an air puff. In FIG. 2B (Right), 15 ingress responses from a single animal to 15 air puffs at high temporal resolution are shown, where the dashed box demarcates epoch in which scaling is expanded at right.

FIG. 2C shows latency to ingress onset in three animals, where individual trials are represented by grey points, and the red line represents a median. The latency to ingress varied little across 15 consecutive trials within each animal, but considerably across animals (FIG. 2C). In contrast, a weak air puff (2 PSI, 15-cm distance) rarely elicited ingress and instead caused the animal to flinch. This apparent startle response (Davis, 1984) was visible as a transient change in burrow position clearly distinct from the ongoing movement of the burrow caused by the animal's breathing (FIG. 2D).

Figure 2D:
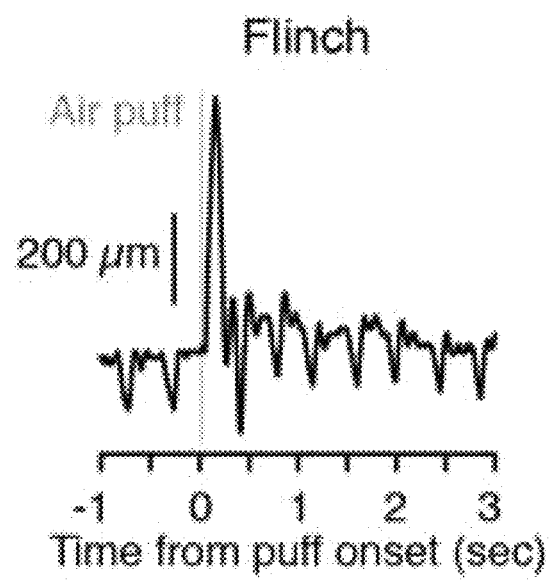
FIG. 2D shows a startle-like flinch in response to light air puff.

FIG. 2D shows startle-like flinches in response to a light air puff, where downward going, approximately 2-Hz oscillations correspond to the animal's breathing cycle, and upward going low-amplitude, transient deflection corresponds to startle in response to air puff (grey boxes, 20 msec, 2 psi) directed toward the animal nose. The reliability and low latency of the response to strong air puff, together with the fact that no training is required, suggest that ingress in the VBA device 1 exploits an innate, highly stereotyped behavioral program. These results demonstrate that this assay is capable of capturing the fine temporal properties of this behavior.

Figure 2E:
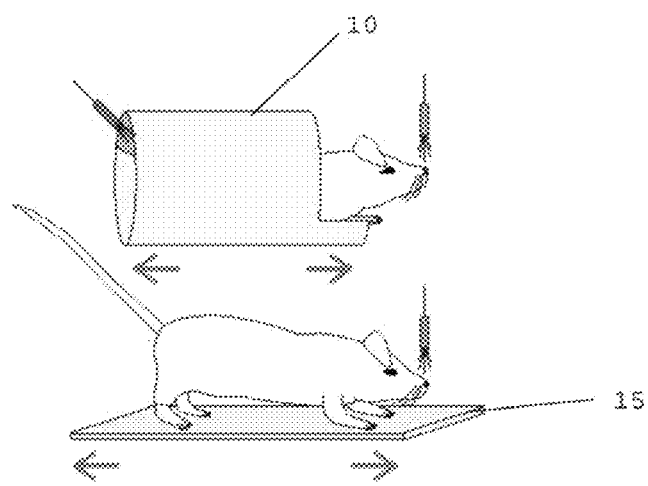
FIG. 2E shows an example of the virtual burrow.
Figure 2F:
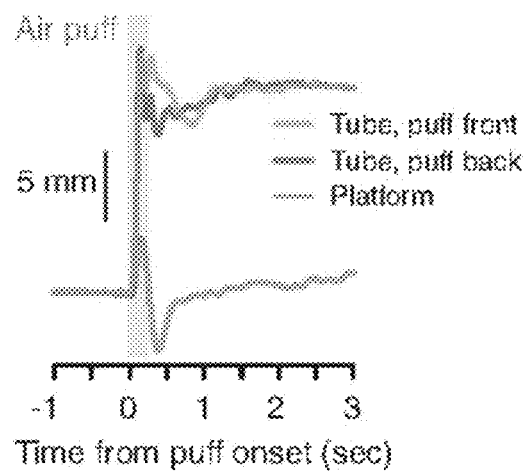
FIG. 2F is a comparison of responses to air puffs delivered to the snout with air puffs delivered to the hindquarters.
Figure 2G:
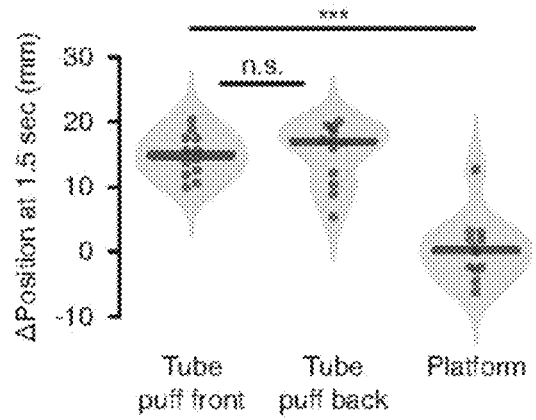
FIG. 2G shows a change in burrow position over time.

Applicant additionally sought to establish whether ingress in response to strong air puff reflects flight to shelter inside the virtual burrow 10, or merely backwards movement away from the source of the stimulus, first by comparing responses to air puffs delivered to the snout with air puffs delivered to the hindquarters (FIG. 2F top, orange vs. green). FIG. 2E shows an example of a tube as the virtual burrow 10 and a platform 15 for the animal. FIG. 2F shows a mean change in burrow position in response to air puff (grey box) across all animals and all trials (N=4 animals, 3 trials each, per condition). FIG. 2G shows a change in burrow position at T=1.5 sec relative to pre-stimulus epoch, pooled across animals and trials. A Wilcoxon rank-sum test was employed to evaluate whether the change in burrow position differed significantly (p(tube-front, tube-back)=0.71, p(tube front, platform.)=9.7×10-05, N=4 mice, 3 trials each, per condition). Individual trials, grey points. Normalized, smoothed histogram, light grey shading. Median, red line. ***indicates p<0.001, n.s. indicates p≥0.05.

As observed previously, all animals ingressed on all trials when air puffs were directed at the snout (FIGS. 2F orange and 2G left, N=4 mice, 3 trials each). When air puffs were directed at the hindquarters, mice also invariably ingressed (FIGS. 2F green and 2G middle, N=4 mice, 3 trials each), which is remarkable since absent head-fixation this action would have resulted in movement towards the source of the air puff.

Thus, the drive to ingress into the virtual burrow 10 overcomes the drive to move in the opposite direction of the air puff. Second, in order to determine whether the enclosure of the virtual burrow 10 is necessary to elicit ingress Applicant replaced the tube with a flat, open platform 15 (FIG. 2E). Mice in this configuration exhibited a transient, flinch-like response to air puff (N=4 mice, 3 trials each), followed by erratic movement of the platform 15 across relatively small distances with no preference in direction (FIG. 2F pink, FIG. 2G right, 14.9 mm median displacement in tube vs. 0.2 mm on platform 15). Thus ingress, which requires the presence of an enclosure, and these observations, together with the high reliability, low latency, and low variability of the response to strong air puff—observed without training—suggest that ingress in the VBA device 1 reflects an innate behavioral program to flee to shelter that unfolds at millisecond timescale.

By simulating key features of the mouse Umwelt (von Uexküll, 1957), Applicant has elicited a set of naturalistic behavioral motifs in spite of the contrivance of head-fixation. These behaviors come readily to mice that have undergone neither training nor extensive acclimation. This, together with the low latency and low variability of the response to noxious air puffs across trials and across animals (FIG. 2A-C); the observation that the drive to ingress can override the drive to move away from the source of the air puff; and the observation that ingress depends upon the availability of an enclosure (FIG. 2D-G); suggests that ingress in the VBA device 1 is reflective of an innate behavioral program to flee to safety. Selective ingress to looming stimuli that evoke flight in freely moving mice (De Franceschi et al., 2016; Yilmaz & Meister, 2013) suggests that ingress is akin to a flight response (FIG. 3). The observation that mice in the VBA device 1 either ingress or egress in response to unanticipated stimuli depending on the configuration of the assay (FIG. 4), parallels the behavior of unconstrained animals, which exhibit either exploration or avoidance depending upon context (Berlyne, 1950; Gershman & Niv, 2015).

Figure 3A:
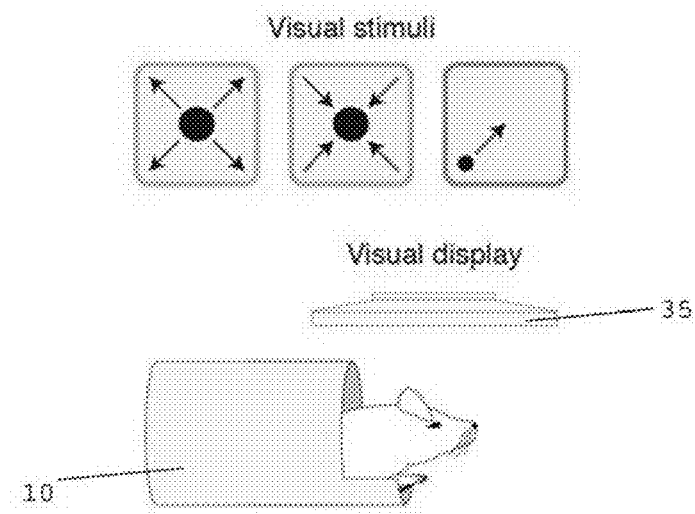
FIG. 3A shows visual stimuli presented to the animal.

Applicant evaluated how behavior in the VBA device 1 compares to the behavior of freely moving animals by presenting stimuli known to trigger specific behavioral responses (De Franceschi et al., 2016; Yilmaz and Meister, 2013). As shown in FIG. 3A, an expanding black disk (left), a contracting black disk (middle), and a sweeping black disk of constant size (right), presented on a visual display 35 were positioned directly over a mouse head-fixed within the virtual burrow (bottom). Applicant employed a visual "looming" stimulus that elicits flight in freely moving mice (De Franceschi et al., 2016; Yilmaz and Meister, 2013) (FIG. 3A) and observed that mice ingressed on 80% of trials in response to an expanding black disk displayed above their heads (FIG. 3A, top left, B, "loom", C, orange, and D, left). This response did not habituate, in contrast to the behavior of freely moving mice (De Franceschi et al., 2016). Presentation of either a contracting black disk (FIG. 3A, top middle, B, "recede", C, pink, and D, middle) or a small black disk sweeping across the visual field (FIG. 3A, top right, B, "sweep", C, green, and D, right) elicited ingress on only 0% or 13% of trials, respectively. Again, this observation is consistent with the behavior of freely moving mice, which do not exhibit flight in response to these stimuli (De Franceschi et al., 2016). These data show that a visual stimulus that selectively elicits flight in feely moving mice selectively elicits ingress in the VBA device 1.

Figure 3B:
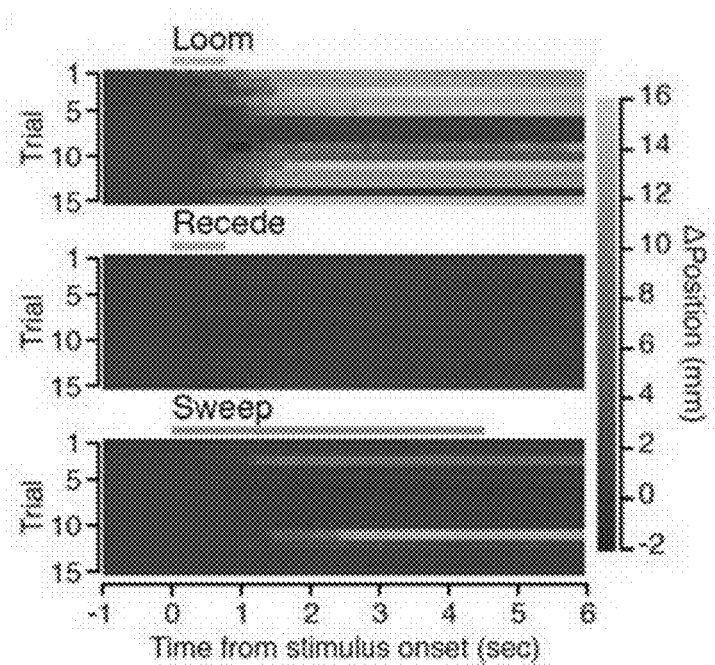
FIG. 3B shows responses to three visual stimuli.
Figure 3C:
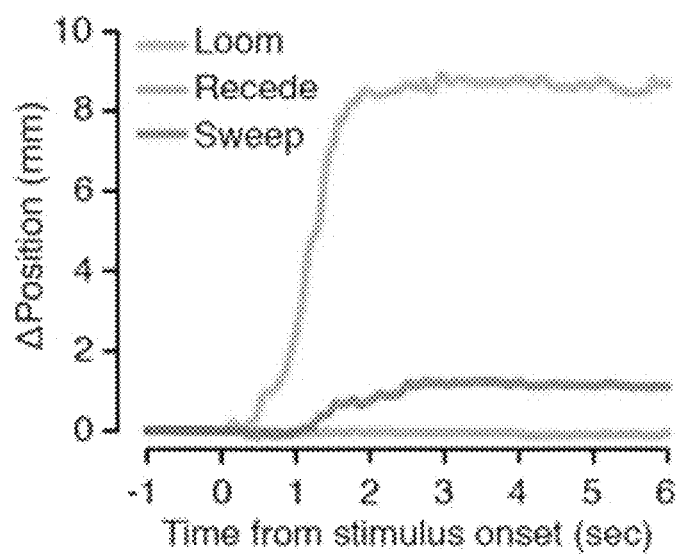
FIG. 3C shows the mean change in burrow position per condition across all animals and trials.

FIG. 3B shows responses to three visual stimuli (n=9 mice, 3 per condition, 5 trials each): Expanding ("loom"), disk widening from 2° to 50° over 250 msec, holding the 50° disk for 500 msec; Contracting ("recede"), disk diminishing from 50° to 2° over 250 msec, holding the 2° disk for 500 msec; Sweeping ("sweep"), 5° disk sweeping smoothly across the diagonal of the screen at a rate of 21/sec (De Franceschi et al., 2016). Color map corresponds to change in burrow position (delta position) with respect to baseline.

Figure 3D:
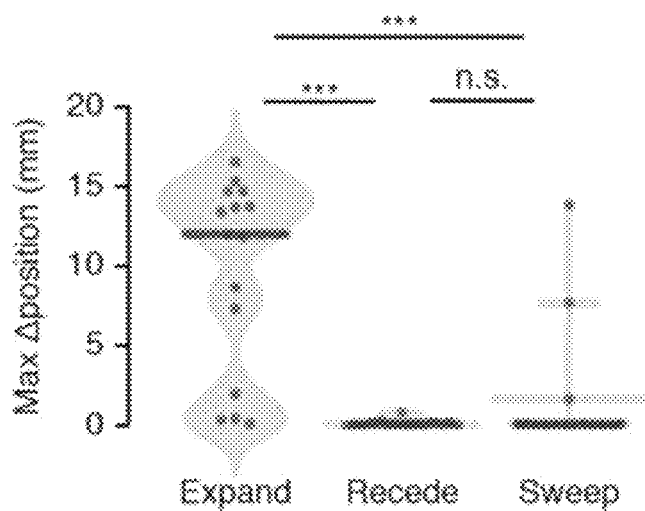
FIG. 3D shows the maximum change in burrow position following stimulus onset per condition across all animals and all trials.

FIG. 3D shows a maximum change in burrow position in the 6 sec following stimulus onset per condition across all animals and all trials. Ingress was defined as a maximum displacement of the burrow relative to the pre-stimulus baseline position >0.85 mm during 5 sec following stimulus onset. The empirical likelihood of ingress was 0.80, 0.00 and 0.20 for loom, recede, and sweep, respectively (9 mice total, 3 mice per stimulus condition, 5 trials per mouse). The grey points in FIG. 3D correspond to individual trials, the Normalized smoothed histogram corresponds to the light grey shading, and the median corresponds to the red line. A two proportion z-test was employed to evaluate whether the probability of ingress differs significantly across stimulus conditions. \*\*\* indicates p<0.001, n.s. indicates p≥0.05.

Figure 4A:
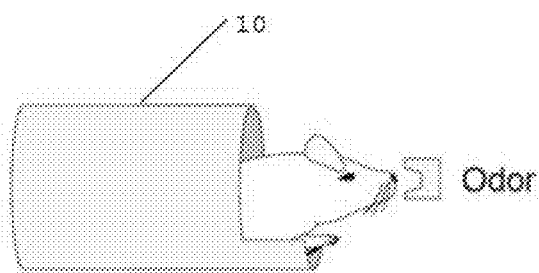
FIG. 4A shows odor stimuli delivered to the animal within the virtual burrow assay.

FIG. 4a shows how mice habituate to novel stimuli: as they become more familiar with a given stimulus they ingress less. Applicant hypothesized that the rate of habituation to novel stimuli may serve as an assay for anxiety; specifically, applicant hypothesized that anxiolytic agents would reduce ingress probability over repeated stimulus presentations.

Figure 9A:
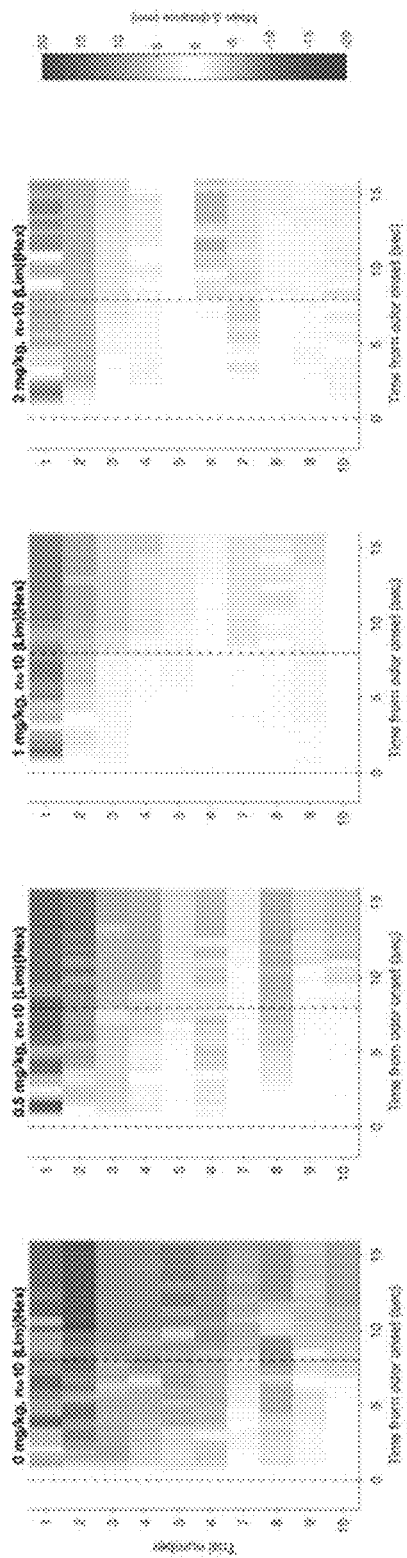
FIG. 9a shows the average position of the burrow over time in five animals per condition of diazepam treatment (tested twice, two weeks apart, at two different drug concentrations for cross-validation); trial number (Y axis); red indicates ingress, blue egress, white no movement relative to pre-trial burrow position; neutral odor stimulus onset at 0, offset at 8 sec.
Figure 9B:
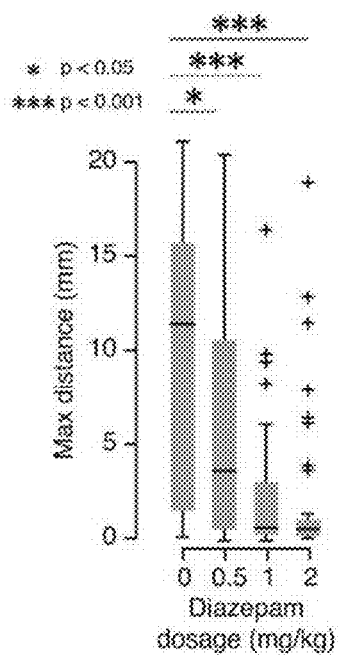
FIG. 9b shows a relationship between ingress and dosage administered.
Figure 9C:
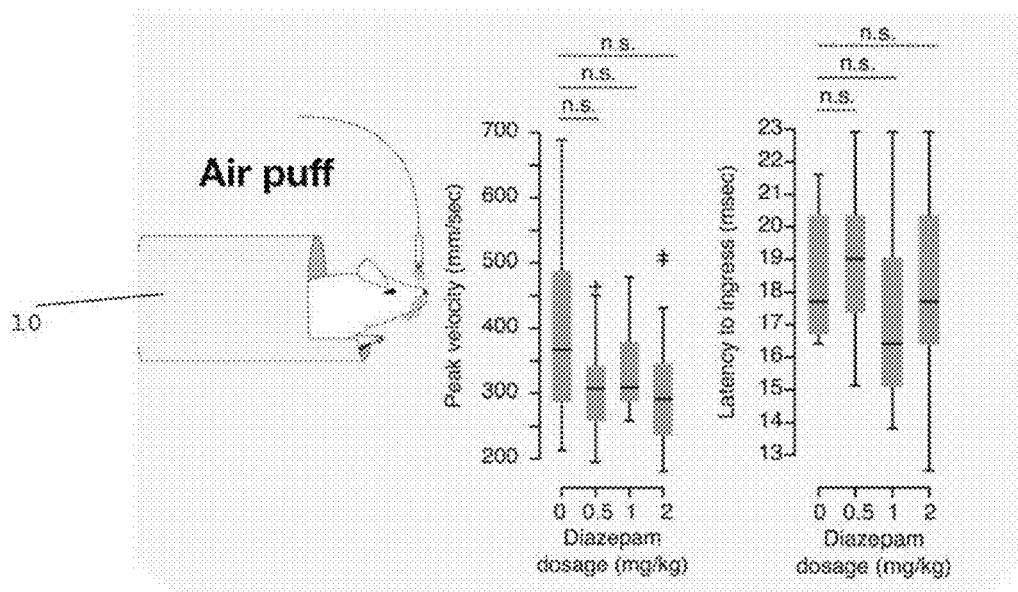
FIG. 9c shows the animals response to an air puff.

Applicant tested this hypothesis by administering to wild-type (C57BL/6J) adult male mice a range of concentrations of the anxiolytic Diazepam (0, 0.5, 1 and 2 mg/kg) and measuring the rate of habituation over ten trials. FIG. 9a shows the average position of the burrow over time in five animals per condition (tested twice, two weeks apart, at two different drug concentrations for cross-validation); trial number (Y axis); red indicates ingress, blue egress, white no movement relative to pre-trial burrow position; neutral odor stimulus onset at 0, offset at 8 sec. FIG. 9b shows a strong dependency of ingress on the dose of Diazepam administered. However, as shown in FIG. 9c, Applicant found the dosage has no measurable effect on the animal's response to an air puff, and neither peak velocity nor latency to ingress are dependent on dosage, and therefore the animal's motor functions with respect to this assay were unaffected at all doses tested. In preliminary experiments, Applicant found that animals habituate to odorant stimuli more rapidly when administered the anxiolytic Diazepam.

In addition, Applicants have demonstrated that the VBA device 1 can measure the effect of the SSRI Fluoxetine (i.e. Prozac), which complements the demonstration above (e.g., that the VBA device 1 can measure the effect of the anxiolytic Diazepam, i.e. Valium), where the animals reaction is a function of the amount administered to the mouse.

Figure 10A:
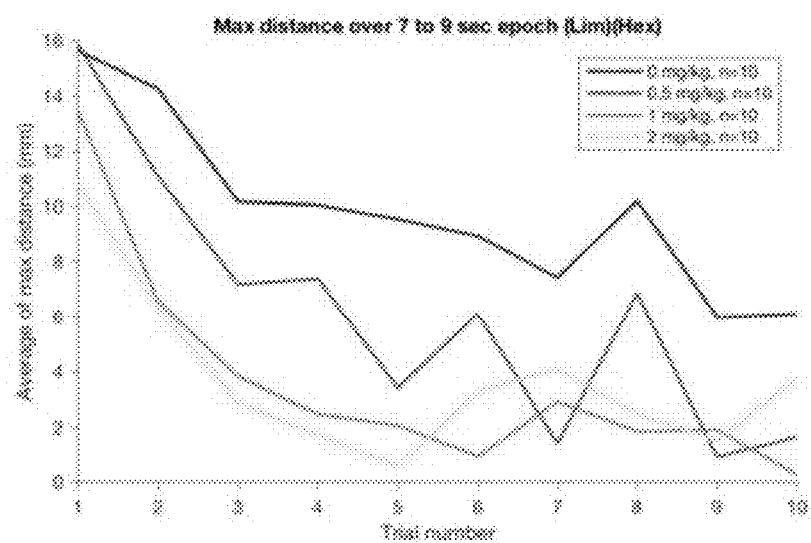
FIG. 10a shows a quantification: mean movement
Figure 10B:
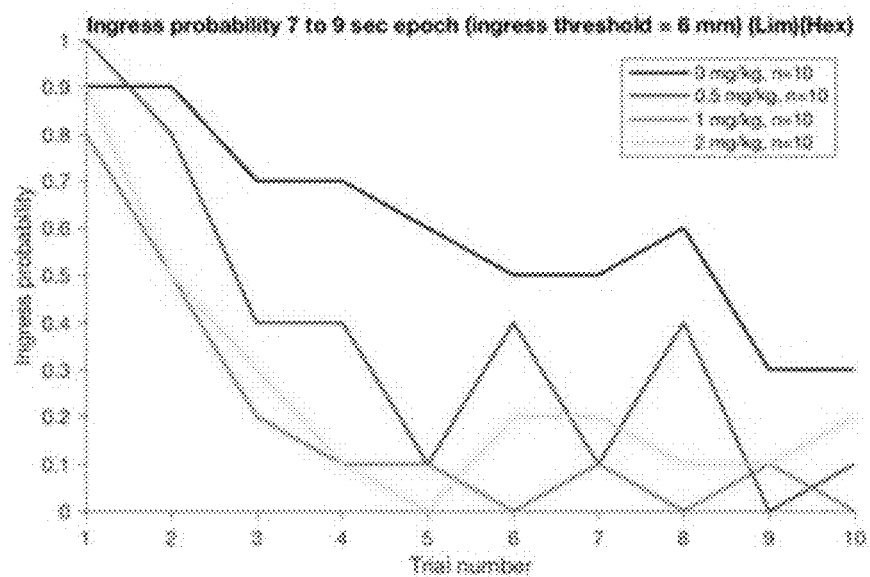
FIG. 10b shows an ingress probability (bottom), as a function of trial number (X axis), grouped by drug concentration.
Figure 11A:
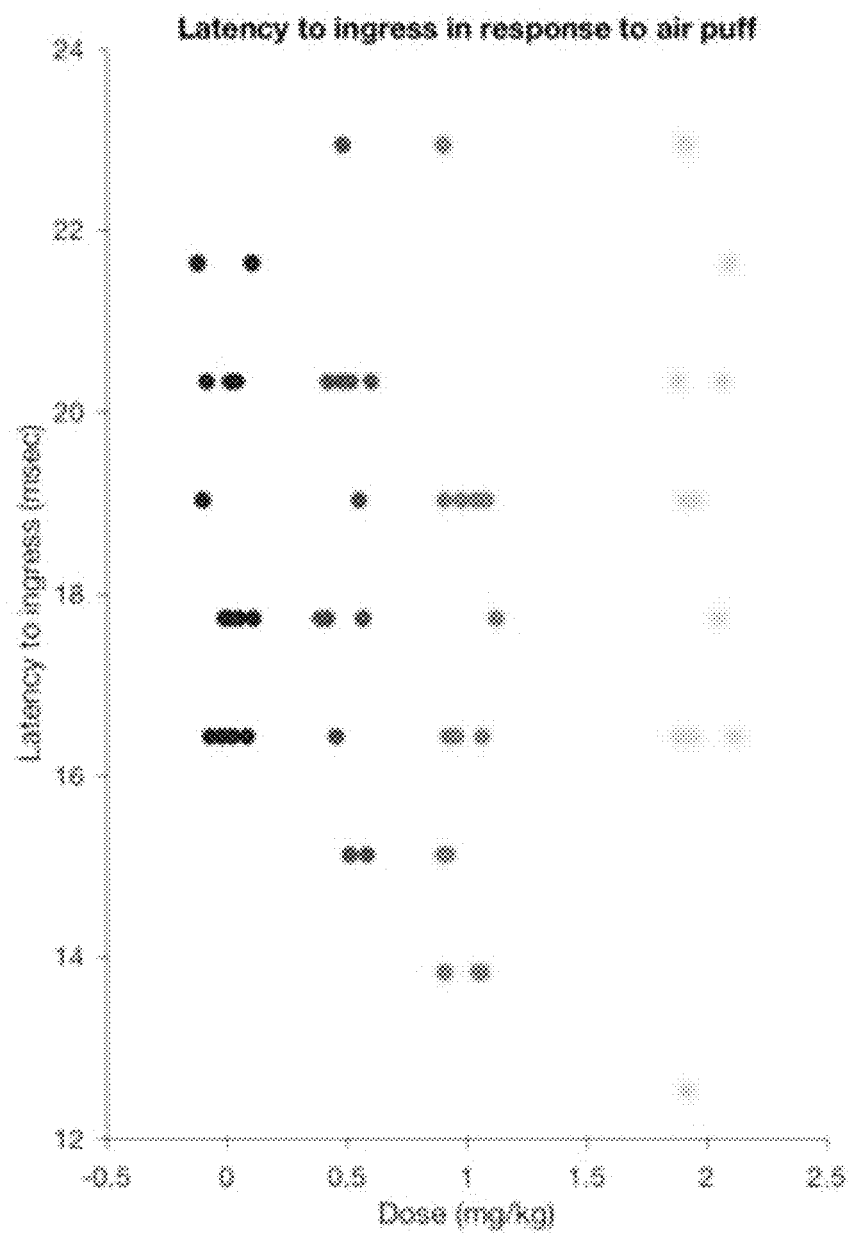
FIG. 11a shows the latency to ingress' in response to a noxious air puff directed at the snout.
Figure 11B:
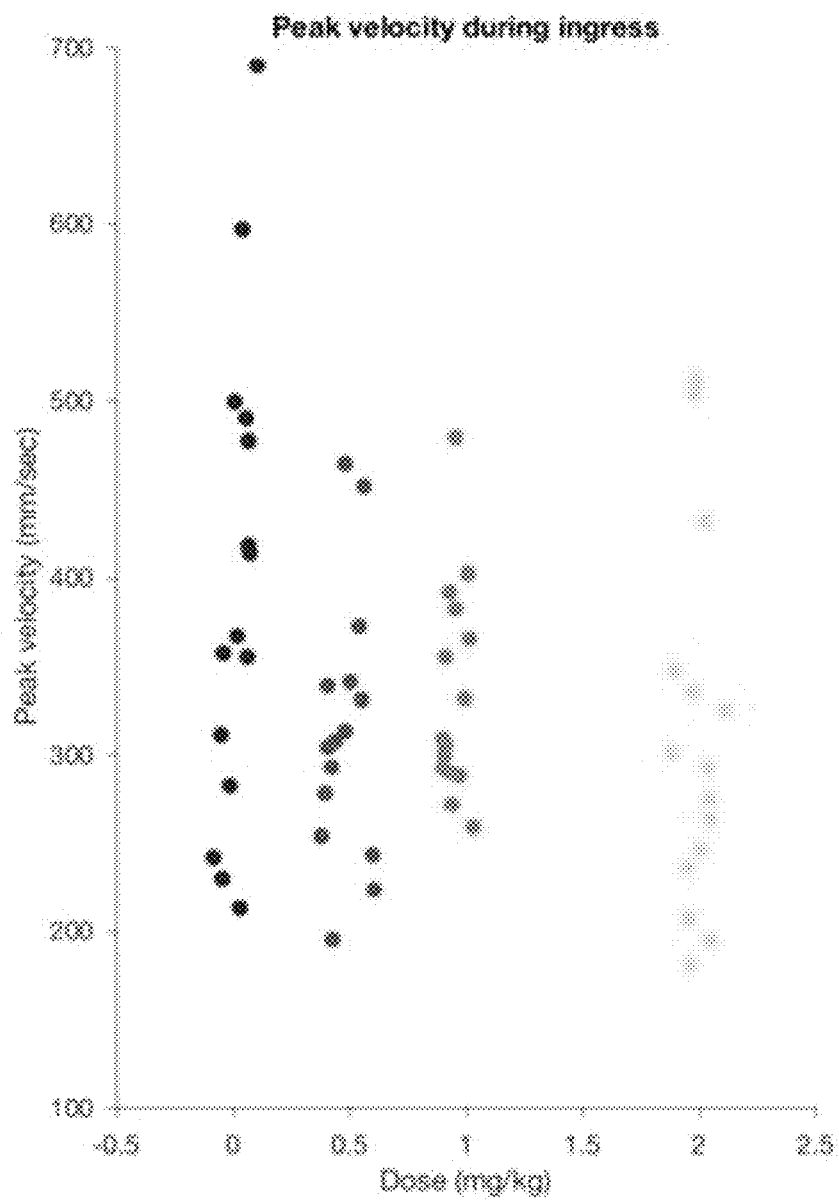
FIG. 11b shows the peak velocity of the burrow during the ingress.

FIGS. 10a and 10b are a quantification of the data of FIG. 9a: mean movement (top panel) and ingress probability (bottom), as a function of trial number (X axis), grouped by drug concentration. A concentration dependence can be observed in some cases on a single trial basis and is clear in individual animals; improved statistical power may be achieved by grouping several trials together. FIGS. 11a and 11b demonstrate that drug concentration has a negligible effect on the motor skills required to displace the burrow: top panel shows the latency to ingress in response to a noxious air puff directed at the snout (lower numbers indicate faster responses), bottom panel shows the peak velocity of the burrow during the ingress. Together, these results confirm the hypothesis that anxiolytic agents reduce ingress probability, and suggest that responses to novel neutral odorant stimuli in the VBA device 1 can be used as an assay for anxiety.

Figure 4B:
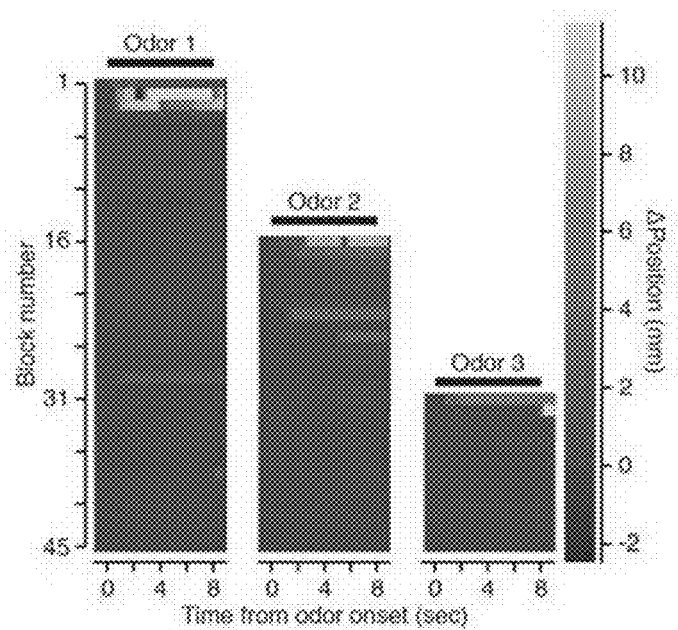
FIG. 4B shows habituating responses to sequential presentation of novel stimuli (Cooke et al. 2015) from a representative mouse, ingressing only on early trials.
Figure 4C:
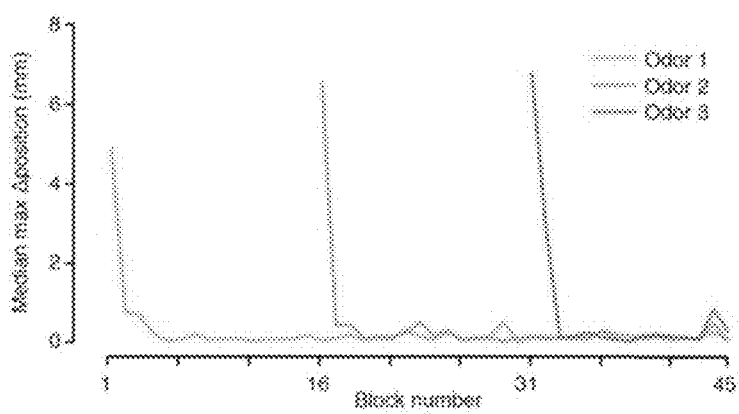
FIG. 4C shows the median value across mice of maximum change in burrow position, per odor condition, per block.

As shown in FIG. 4A, three odor stimuli were delivered to mice within the virtual burrow assay. FIG. 4B shows habituating responses to sequential presentation of novel stimuli (Cooke et al. 2015), from a representative mouse, and FIG. 4C shows the median value across mice of maximum change in burrow position, per odor condition, per block. FIG. 40 shows the maximum change in burrow position for each odor during the first three trials (left) and all later trials (right), pooled across animals. The probability of ingress ($p_{ingress}$) for all odors on the first three trials (left) and all subsequent trials, Odor 1: $p_{ingress}$ (trials 1-3)=0.80, $p_{ingress}$ (trials 4-45)=0.18; Odor 2: $p_{ingress}$ (trials 1-3)=0.67, $p_{ingress}$ (trials 4-30)=0.20. Odor 3: $p_{ingress}$ (trials 1-3)=0.60, $p_{ingress}$ (trials 4-15) 0.23, where individual trials correspond to grey points, and Normalized smoothed histogram corresponds to light grey shading, and Median corresponds to a red line. A two-proportion z-test on ingress probability pooled across all mice (n=5) and all trials was employed to evaluate whether the probability of ingress differed significantly; ingress defined as maximum displacement <0.75 mm during the 8-sec stimulus epoch. * indicates p<0.05, *** indicates p<0.001.

A habituated response can transiently increase following presentation of a different stimulus, a phenomenon termed dishabituation (Groves & Thompson, 1970; Thompson & Spencer, 1966). However, renewed ingress to Odor 1 was not observed following the first presentation of Odor 2 or Odor 3. On early trials mice occasionally exit the virtual burrow before initiating their ingress. Applicant speculated that this voluntary "egress" corresponds to an exploratory bout, and to test this the odor source was coupled to the burrow, so that egress from the burrow brought the odor source closer to the animal's nose, while ingress distanced it (FIG. 4E). FIG. 4E shows an example of an odor port coupled to the virtual burrow 10; the mouse is required to egress in order to draw the odor source closer to its nose. The odor port may deliver a stimulus a stimuli and/or a reward, where the animal being is required to egress in order to approach and/or investigate the source of such stimulus and/or reward (e.g., food or water or a food odor).

Applicant reasoned that granting the animal control over its proximity to an odor port 85 would allow it to select between the drive to explore an odorant stimulus (by exiting the burrow) and the drive to remain inside. In contrast to all other experiments, in which trials were initiated while the animal was in a mandatory egress position, here the animals were granted control over burrow position at all times and almost invariably maintained full ingress prior to stimulus delivery. Applicant observed that under this configuration mice exited the virtual burrow 10 for brief (~1 sec) bouts before resuming a fully ingressed position (FIG. 4F). FIG. 4F shows a habituating response of a representative mouse to repeated presentations of an odorant stimulus, where Downward-going traces correspond to egress, and a grey arrow indicates odorant stimulus onset (8-sec duration).

This response habituated, with the animals egressing further on early than on later trials (median egress 21.9 mm for trials 1-2 versus 10.5 mm for trials 3-5, N=5 mice, FIG. 4G, FIG. 4H). Together, these results indicate that the VBA device 1 measures selective responses to unanticipated stimuli-ingress or egress, depending upon the configuration of the assay—and that these behaviors can be employed to measure habituation. FIG. 4G shows mean responses across all mice tested (N=5), where warmer colors depict egress rather than ingress. FIG. 4H shows a Maximum change in burrow position during the first two trials (left) and the subsequent three trials (right), pooled across animals. A Wilcoxon rank-sum test was employed to evaluate whether the maximum change in burrow position differed significantly (p(trials 1-2, trials 3-5)=0.0021, N=5 mice). Individual trials, grey points. Normalized, smoothed histogram, light grey shading. Median, red line. ** indicates p<0.01.

Figure 4D:
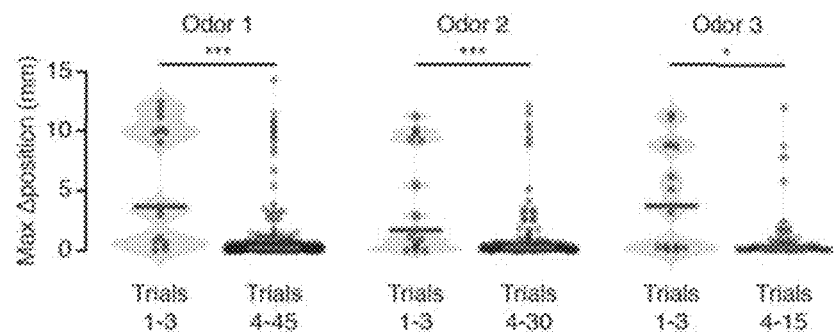
FIG. 4D shows the maximum change in burrow position for each odor during the first three trials (left) and all later trials (right), pooled across animals.
Figure 4E:
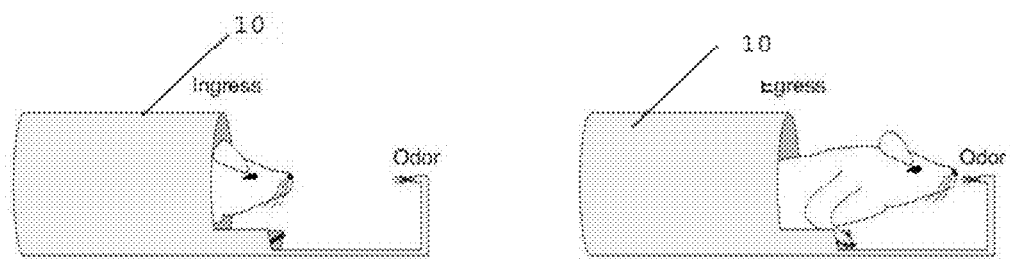
FIG. 4E shows a diagram of the odor port coupled to the virtual burrow.
Figure 4F:
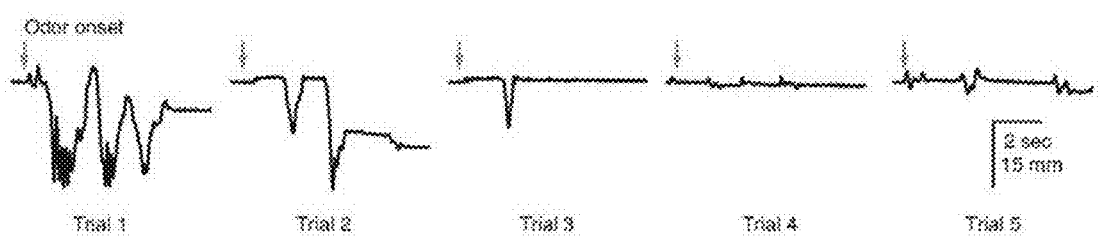
FIG. 4F shows a habituating response of an animal to repeated presentations of an odorant stimulus, egressing only on early trials.
Figure 4G:
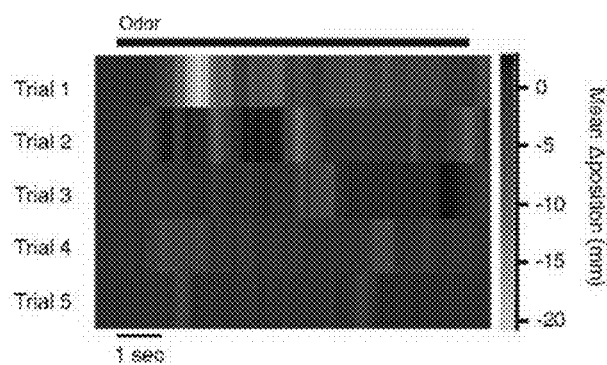
FIG. 4G shows mean egress responses across all animals tested.
Figure 4H:
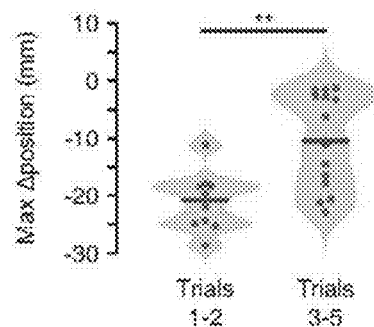
FIG. 4H shows a maximum change in burrow position during the first two trials (left) and the subsequent three trials (right), pooled across animals.
Figure 22A:
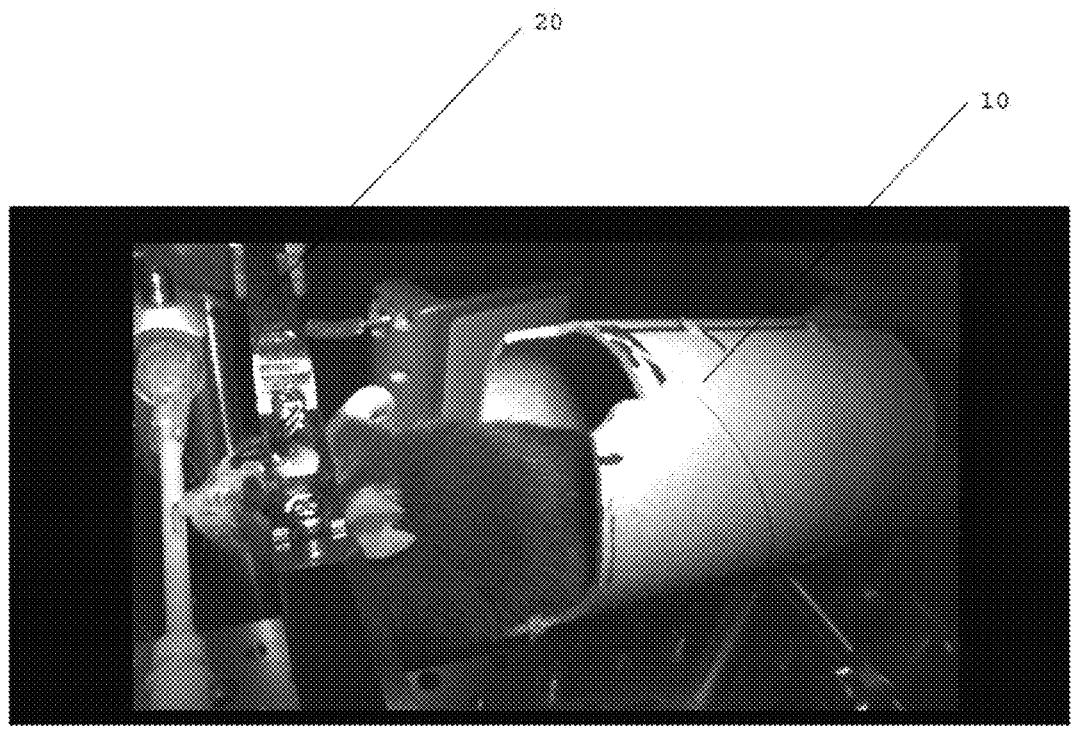
FIG. 22a shows a head fixed animal being presented a stimulus.

Applicant found that when presented with novel, neutral odorants (FIG. 22a) mice initially ingress, but the response largely habituates after the first three trials (Odor 1, FIG. 4A-C, first 15 blocks, and FIG. 4D, left panel). Applicant asked whether this behavior reflects nonspecific habituation to all olfactory stimuli or whether it is stimulus selective. After 15 presentations of Odor 1 applicant introduced a second, novel, neutral odor (Odor 2, 4B,C blocks 16-30, Odor 1 and Odor 2 presented in pseudorandom order within each block) and found that while mice selectively ingressed in response to Odor 2 during early trials, they remained unresponsive to the familiar odor. Similarly, after 15 blocks of Odors 1 and 2, applicant introduced a third, novel, neutral odor (Odor 3, FIG. 4B, FIG. 4C, blocks 31-45, Odor 1, Odor 2, and Odor 3 presented in pseudorandom order within each block) and again observed ingress in response to the novel odor during early trials but not to the familiar ones. Applicant found that the probability of ingress on the first three presentations of a given odor was significantly higher than the probability of ingress on later presentations of that same odor for all odors tested (FIG. 4D). These data indicate that the VBA device 1 can be employed to detect selective responses to novel stimuli.

In contrast to traditional assays, sensory detection and discrimination can be directly measured in the VBA device 1 without any training, bypassing these confounds (e.g. FIG. 4), and by using only passive exposure to neutral stimuli and measuring behavioral evidence of habituation, the VBA device 1 can assay memory directly without any need for motivating and/or training the animal, bypassing these confounds (e.g. a multi-day version of the experiment described in FIG. 4). The VBA device 1 implements a sensitive assay of habituation to stimuli that requires no training or positive/negative reinforcers (e.g. FIG. 4). Applicant anticipates that rodent models of Schizophrenia and ASD will habituate more slowly to novel stimuli than wildtype animals, and such habituation experiment (FIG. 4) could be easily translated into an oddball paradigm that mirrors the one employed in humans.

Figure 5A:
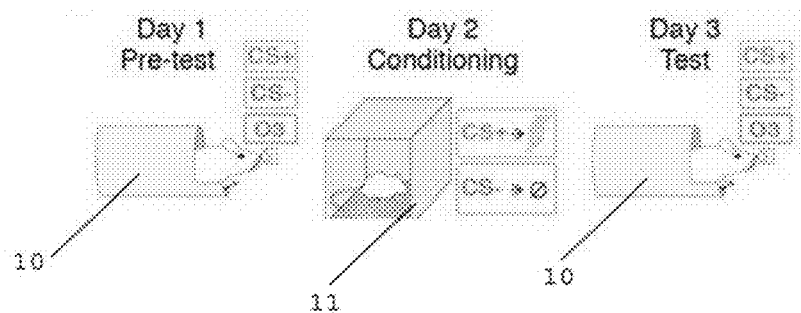
FIG. 5A shows odor stimuli presented to mice.
Figure 22B:
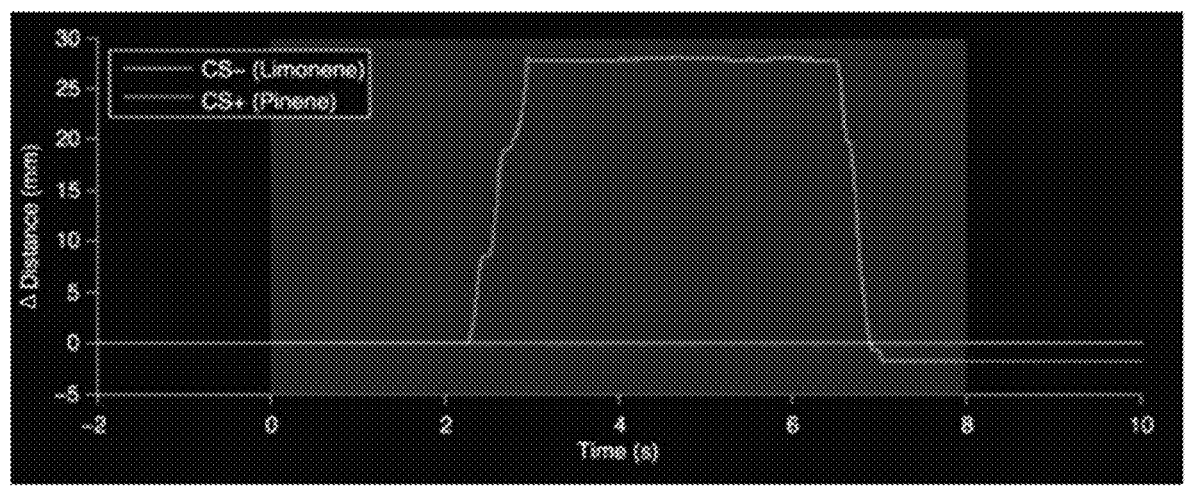
FIG. 22b shows the position of the virtual burrow over time when CS− and CS+ odorants are presented to the animal.
Figure 23A:
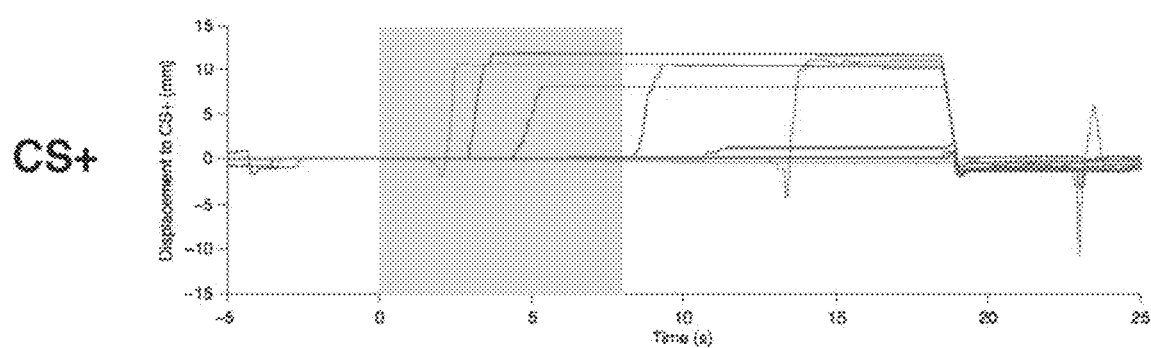
FIG. 23a shows displacement to CS+ over time.
Figure 23B:
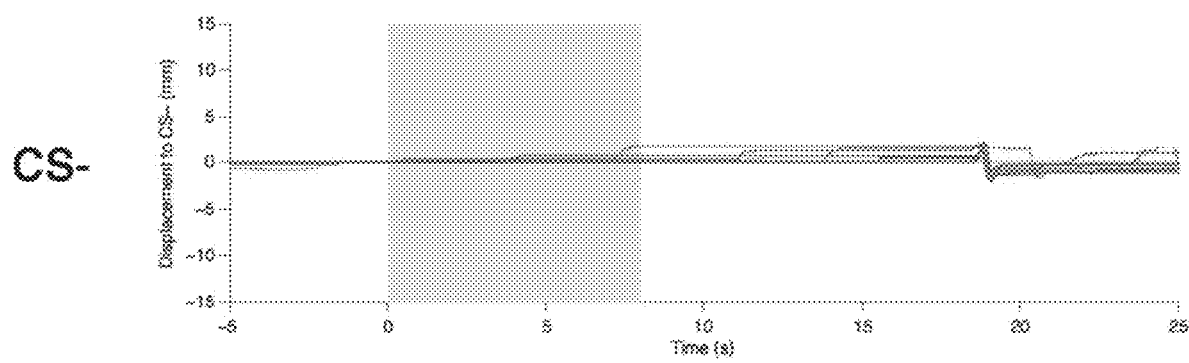
FIG. 23b shows displacement of CS− over time.
Figure 24A:
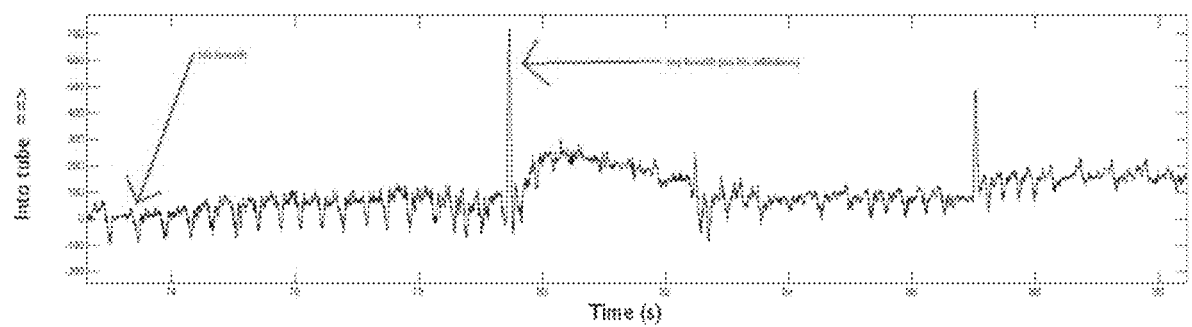
FIG. 24a shows a distance into the tube over time.
Figure 24B:
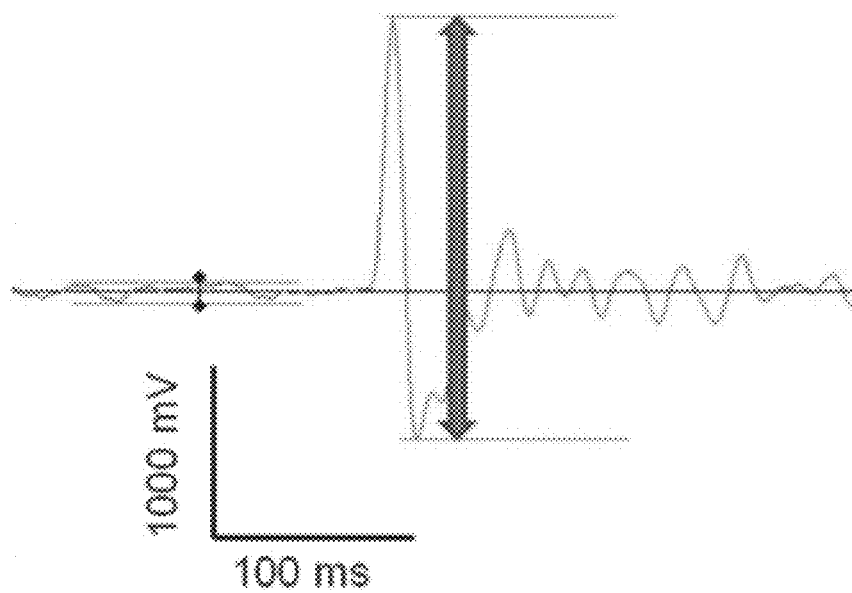
FIG. 24b shows a measurement of voltage over time.
Figure 25:
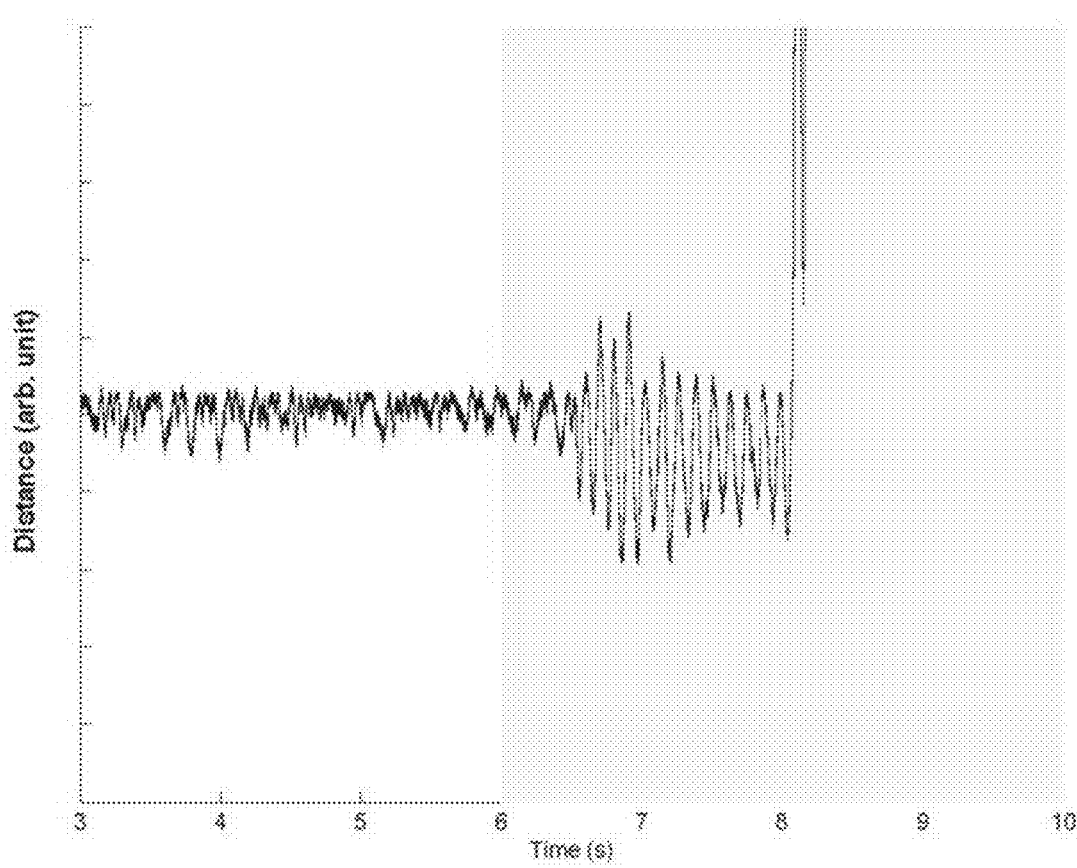
FIG. 25 shows a plot of distance over time.
Figure 26:
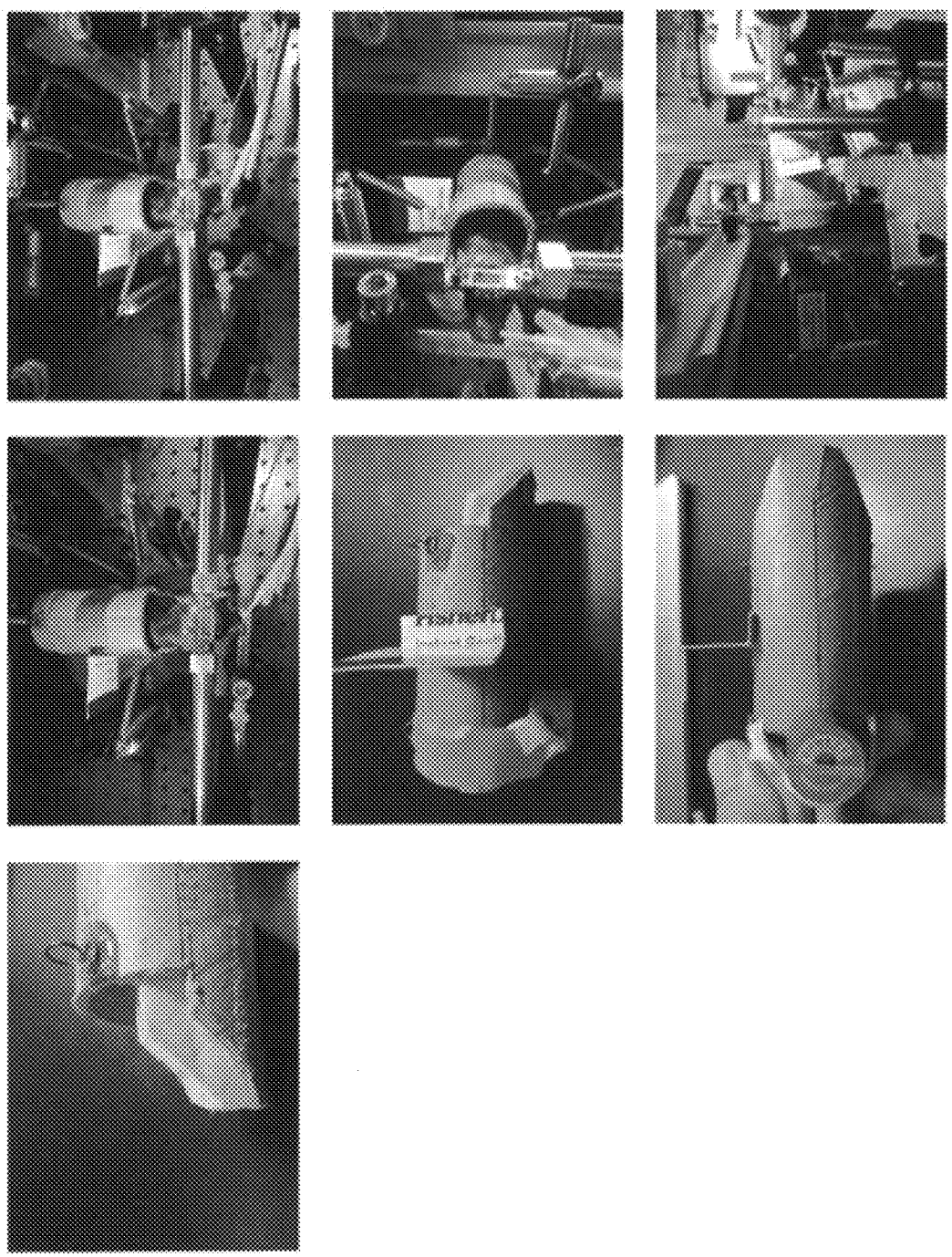
FIG. 26 shows various views of the virtual burrow assay.

Applicant next determined whether the VBA device 1 can measure responses to aversively conditioned stimuli. As shown in FIG. 5A, applicant employed a classical conditioning paradigm in which on day 1 (Pre-test) responses in the VBA device 1 to three neutral odorants were measured. On day 2 (Conditioning) applicant placed the mice in a fear conditioning box 11 and paired one odor with foot shock (CS+) and presented a second odor without foot shock (CS−); the third odor presented during pre-test (O3) was never presented on day 2. On day 3 (Test) applicant measured responses in the VBA device 1 to all three odor stimuli (FIG. 5A). Following classical conditioning, in which a CS+ odorant is paired with foot-shock and the CS− odorant is not, mice ingress in response to the CS+ alone, a behavior that extinguishes after repeated presentation (FIG. 22b, FIG. 23a and FIG. 23b). The VBA device 1 thus affords single-trial determination of whether a given stimulus evokes an aversive response and resolves the precise timing of ingress, permitting examination of the neuronal state that precedes this behavioral transition. The assay may accommodate modalities other than olfaction and is compatible with standard electrophysiological and optical methods for measuring and perturbing neuronal activity.

The selective response to a second odor following habituation to the first demonstrates that the response decrement is due neither to adaptation of the sensory epithelium nor to effector fatigue (Groves & Thompson, 1970; Rankin et al., 2009; Thompson & Spencer, 1966). Since this habituation is stimulus-selective, the VBA device 1 can implement a discrimination assay that requires no training. This strategy has been employed across many experimental systems, ranging from the olfactory system of freely moving rodents to the visual system of human infants (Friedman, 1972), and can be exploited to construct psychometric curves for detection or discrimination without training.

Figure 5B:
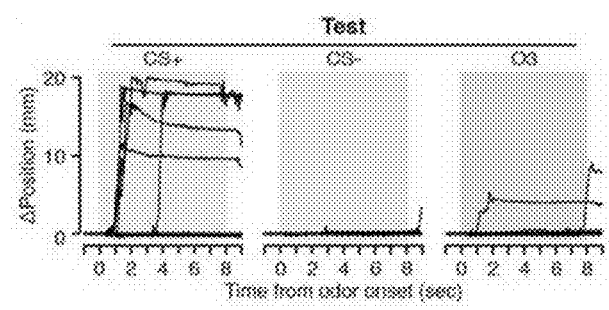
FIG. 5B shows change in burrow position relative to pre-stimulus baseline on individual trials after odor-shock conditioning from a representative mouse.
Figure 5C:
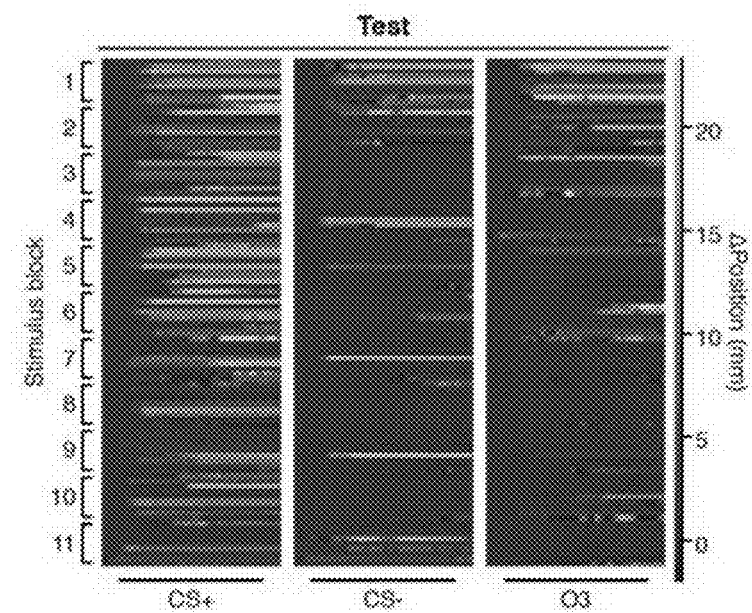
FIG. 5C shows a change in burrow position relative to pre-stimulus epoch.
Figure 5D:
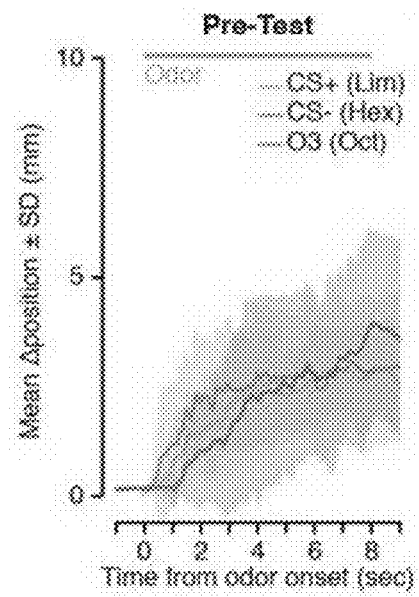
FIGS. 5D, 5E shows the mean change in burrow positions during Pre-test (D) and Test (E) relative to pre-stimulus baseline per odor condition during stimulus blocks 2-7.
Figure 5E:
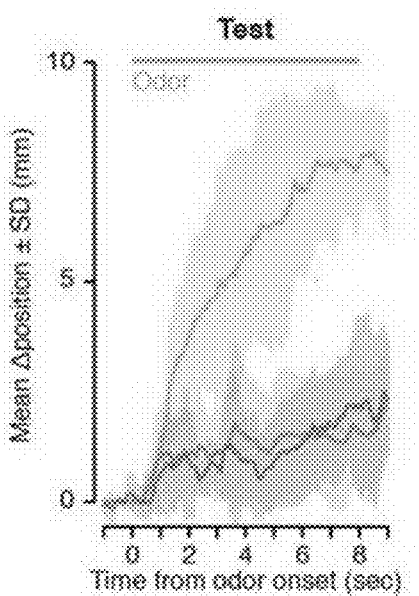

FIG. 5B shows a change in burrow position relative to pre-stimulus baseline on individual trials after odor-shock conditioning from a representative mouse, where the colored box demarcates odor stimulus epoch, and CS+: paired with shock; CS−: unpaired with shock; Odor 3 (O3): not presented in fear conditioning box 11. FIG. 5C shows a change in burrow position relative to pre-stimulus baseline (color map), ordered by mouse within each stimulus bloc, where the lines at the bottom indicate odor stimulus epoch (8-sec duration). FIGS. 5D, 5E graphically show a mean change in burrow positions during Pre-test (D) and Test (E) relative to pre-stimulus baseline per odor condition during stimulus blocks 2-7 (shading indicates ±1 standard deviation, n=9 mice), where the grey line the top corresponds to odor stimulus epoch.

Figure 5F:
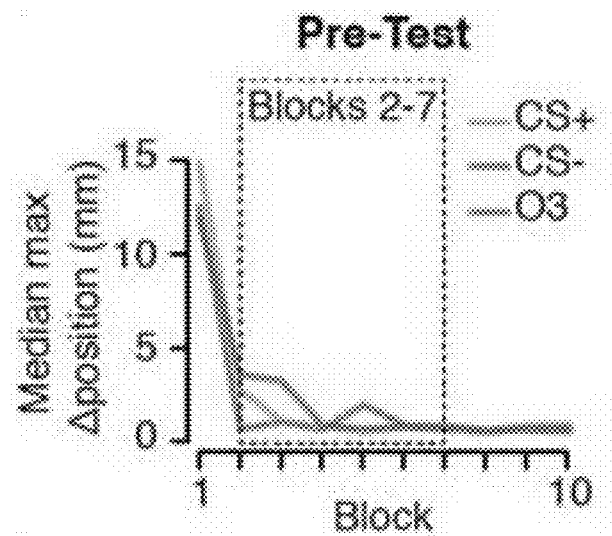
FIGS. 5F, 5G shows a median value across mice of maximum change in burrow position, per odor condition, per block during pre-test (F) and Test (G).
Figure 5G:
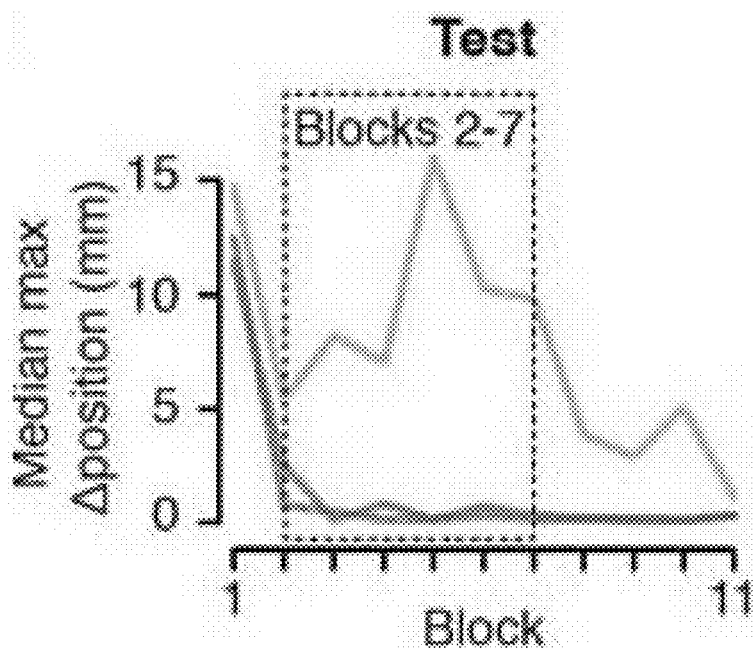
Figure 5H:
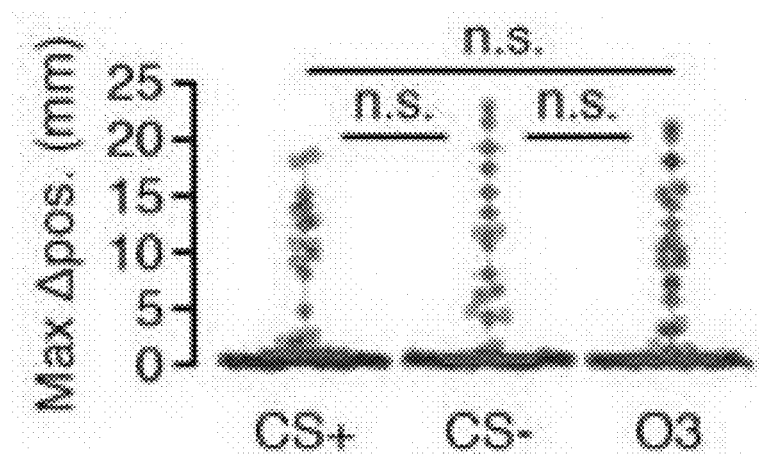
FIGS. 5H, 5I shows maximum change in burrow position during the odor stimulus, per condition across all animals and all trials during Pre-test (H) and Test (I).
Figure 5I:
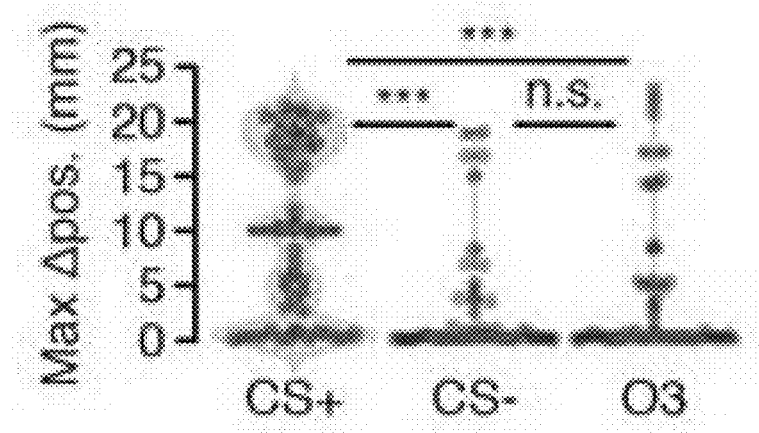

FIGS. 5F, 5G show a median value across mice of maximum change in burrow position, per odor condition, per block during pre-test (F) and Test (G), where Dashed boxes demarcate blocks 2-7, used to obtain mean responses and to perform statistical tests. FIGS. 5H, 5I graphically shows a maximum change in burrow position during the odor stimulus, per condition across all animals and all trials during Pre-test (H) and Test (I). Individual trials are represented by grey points, normalized, smoothed histogram, is represented by light grey shading, and a red line represents a median. The probability of ingress for each odor stimulus during Test: CS+: $P_{ingress}$=0.76; CS−: $P_{ingress}$=0.35; O3: $P_{ingress}$=0.39; $P_{ingress}$ (CS+)>$P_{ingress}$ (CS−) $p<0.001$; $P_{ingress}$ (CS+)>$P_{ingress}$ (O3) $p<0.001$, two-proportion z-test on ingress probability pooled across all mice on blocks 2-7; ingress defined as maximum displacement >0.75 mm during the 8-sec stimulus. *** indicates $p<0.001$, n.s. indicates $p<0.05$.

Applicant found that mice ingressed in response to all three odor stimuli during the first block of Pre-test (FIG. 5F, block 1) and habituated over subsequent presentations (FIG. 5D,F,H), consistent with the observation that animals ingress in response to novel odors (FIG. 4). Following odor-shock pairing, applicant found that the likelihood of ingress was markedly higher in response to the CS+ than to the two stimuli not paired with shock (CS+ 76%, CS− 35%, O3 39%, FIG. 5B,C,E,G,I). Moreover, mice ingressed markedly more to the CS+ during Test than during Pre-test (Test 76%, Pre-test 37%, FIG. 5D versus E, F versus G, and H versus I). All nine mice tested exhibited a greater likelihood of ingress to CS+ than to CS− or O3; in eight out of nine this effect was significant (p<0.05, two-proportion z-test on trials 2-7 to mitigate the effects of novelty served on the first trial and extinction observed on the last three trials). This result is robust to the choice of ingress threshold over a range of 0.5 to 10 mm (FIG. 5, FIG. 6). Thus the VBA device 1 can detect stimulus-selective conditioned responses following aversive conditioning.

Figure 5J:
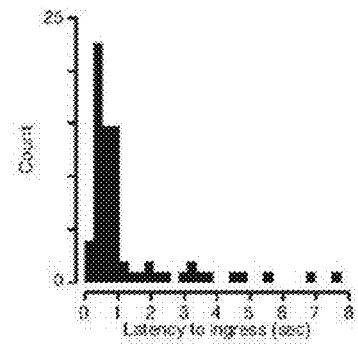
FIG. 5J shows a distribution of ingress onset latency during CS+ trials for the animals.
Figure 5K:
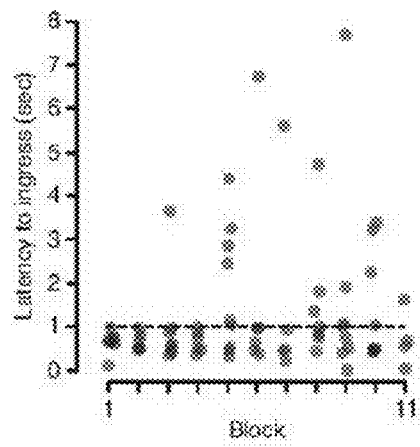
FIG. 5K shows ingress onset latency for the animals as a function of block number.
Figure 5L:
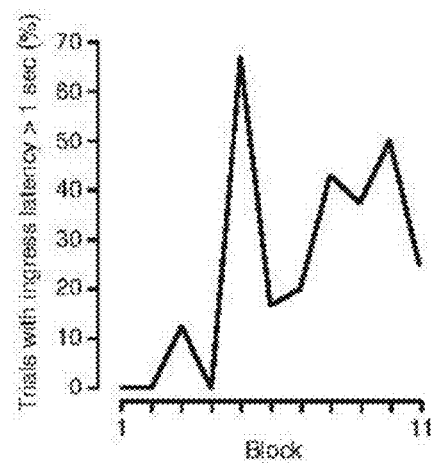
FIG. 5L shows a fraction of ingresses whose latency exceeded 1 sec.
Figure 6:
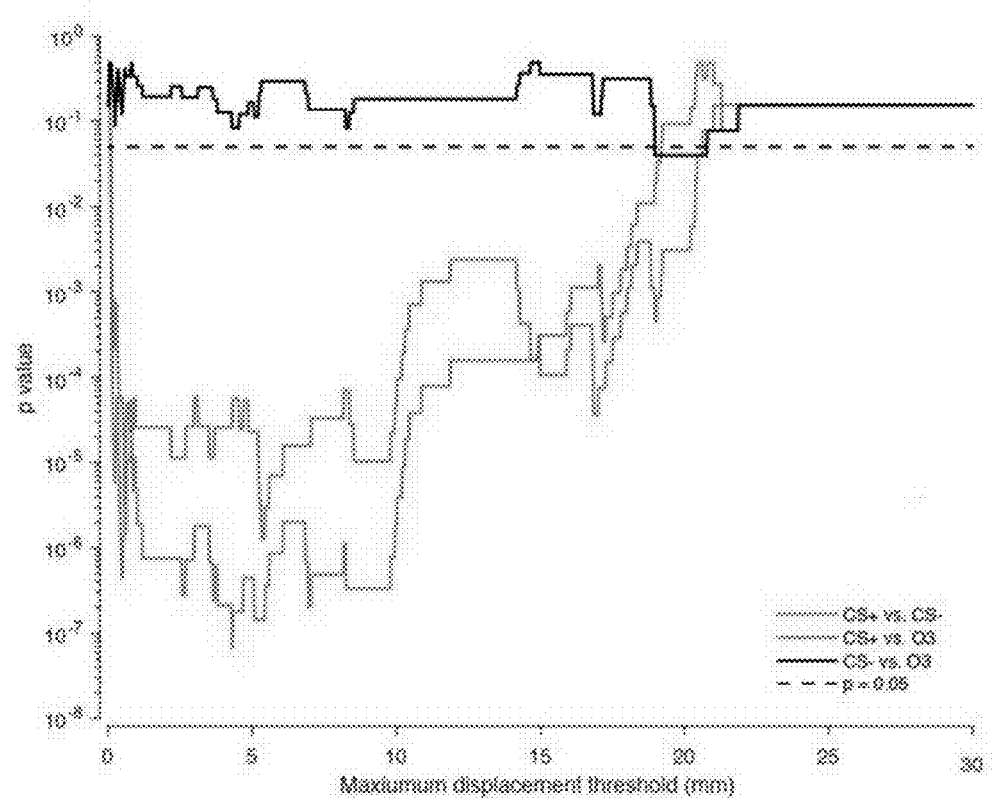
FIG. 6 shows robustness of statistical test to choice of ingress threshold.

FIG. 5J shows a distribution of ingress onset latency during CS+ trials for all mice, where Ingress onset is defined as the first time bin in which displacement exceeded 0.75 mm following stimulus onset. FIG. 5K shows ingress onset latency for all mice as a function of block number, where a dashed line indicates a threshold for high latency ingresses (>1 sec). FIG. 5L shows a fraction of ingresses having a latency exceeding 1 sec.

Figure 7:
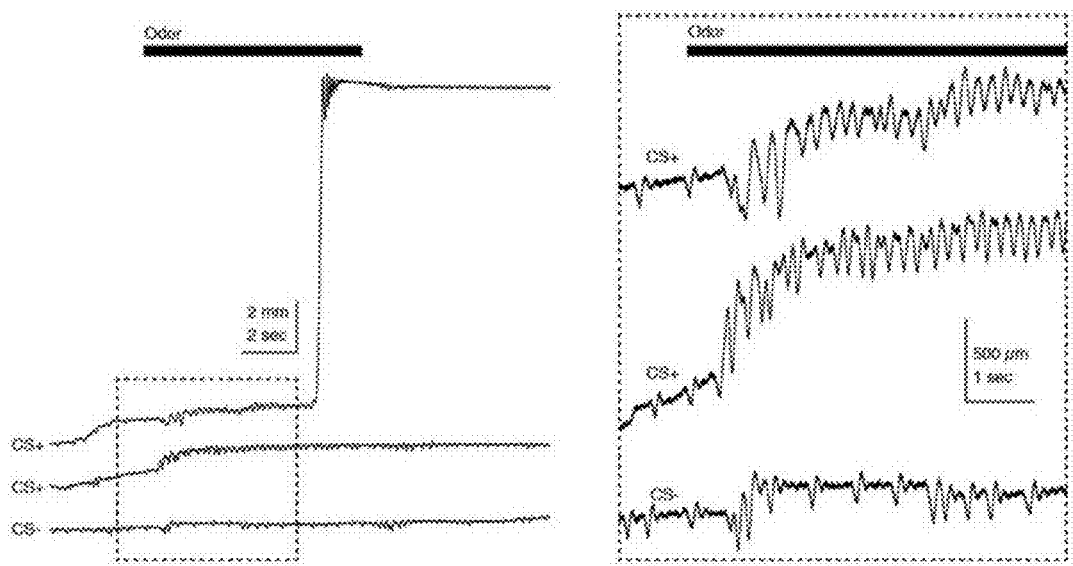
FIG. 7 shows tremble in response to aversively conditioned odor stimuli.

A subset of mice exhibited a second behavioral response specific to the CS+ following conditioning: an oscillation in burrow position (FIG. 5, FIG. 7). The high frequency of this oscillatory response distinguished it from the lower frequency oscillations that correspond to the animal's breathing cycle (FIG. 5, FIG. 7, top and middle traces versus bottom trace; see also FIG. 2D).

Simultaneous video recording (not shown) indicated that it is instead associated with trembling of the animal's body. This trembling sometimes preceded ingress by several seconds (FIG. 5, FIG. 7, top trace), or occurred on ingress-free trials (FIG. 5, FIG. 7, middle trace), and was selective for the CS+ stimulus following conditioning.

FIG. 6 graphically shows robustness of statistical test to choice of ingress threshold, where an effect of maximum displacement threshold on the two-proportion z-test p value for the pooled test data (n=9 mice), and the dashed line indicates p=0.05.

FIG. 7 graphically shows tremble in response to aversively conditioned odor stimuli, and the virtual burrow position during three individual trials recorded during Test, in response to CS+ and CS−. High-frequency, low amplitude trembling was directly measured following fear conditioning. Odor stimulus epoch is denoted by the black bar (top), and the dashed box at left demarcates epoch in which scaling is expanded at right. High frequency and amplitude oscillation were observed during presentation of the CS+ (top, middle) but not the CS− (bottom), and low frequency and amplitude oscillation preceding the stimulus epoch corresponds to the animal's breathing cycle.

Figure 8:
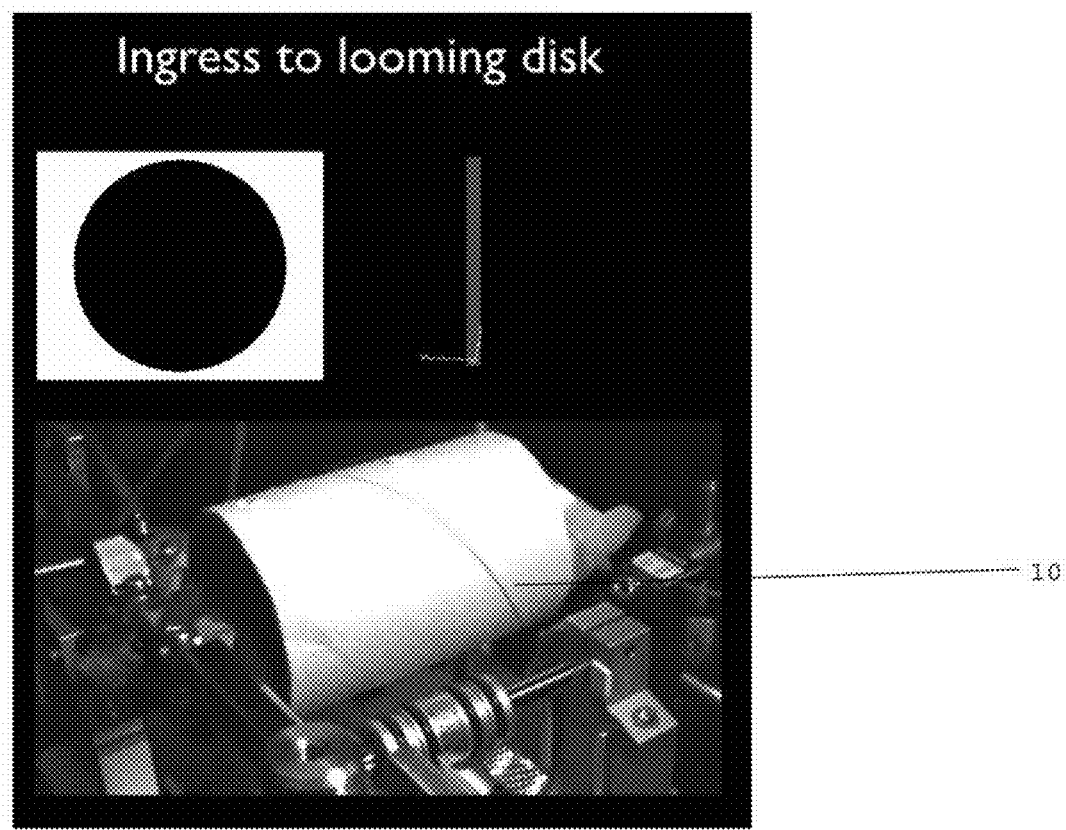
FIG. 8 (top left panel) shows a visual stimulus presented on a screen positioned above the animal's head; bottom panel shows a mouse head-fixed in the VBA; top right panel shows a position of the virtual burrow measured by a laser displacement sensor (grey rectangle indicates the stimulus epoch).

FIG. 8 (top left panel) shows a visual stimulus presented on a screen positioned above the animal's head; bottom panel shows a mouse head-fixed in the VBA device 1; top right panel shows a position of the virtual burrow 10 measured by a laser displacement sensor 60 (grey rectangle indicates the stimulus epoch).

This application also describes methods for detecting behavioral responses of an animal to aversive stimuli. A method, according to one embodiment (FIG. 12), includes sliding the virtual burrow along an anterior-posterior axis of the animal, the animal being head-fixed to a head stabilizer and being permitted to egress and ingress the virtual burrow (step S120); adjustably retracting, by the controller, the linear actuator which is coupled to the virtual burrow to an egress position along an axis of movement of the virtual burrow and advancing the linear actuator to an ingress position along the axis of movement of the virtual burrow; (step S121); detecting, via the position sensor, a position of the virtual burrow and detecting, via the force sensor, a force exerted by the animal against the linear actuator, when the linear actuator is in the egress position (step S122); and causing, by the controller and based on the position detected by the position sensor and the force detected by the force sensor, the linear actuator to be advanced from the retracted egress position to the ingress position in which the animal is in control of the position of the virtual burrow step (S123).

Additional steps may optionally be added to the method to impart additional features or characteristics to the VBA device 1.

Applicant has designed an assay to measure flight-like responses to both conditioned and innately aversive stimuli in head-fixed mice. The Virtual Burrow Assay captures a facet of the mouse Umwelt (the environment as it is experienced by members of a species) (von Uexküll, 1957) by simulating the scenario in which the animal is poised at the threshold of its burrow and evaluates whether to remain exposed to potential threats outside or to retreat inside the enclosure.

Looming stimuli that selectively evoke flight in freely moving mice (De Franceschi et al., 2016; Yilmaz and Meister, 2013) also selectively elicit ingress in headfixed mice in the VBA device 1 (FIG. 3). Noxious air puffs delivered to the nose invariably evoke ingress at latencies of tens of milliseconds (FIG. 2). This behavior comes readily to naïve, head-fixed mice that have neither undergone training nor extensive acclimation, suggesting that the reliability and stereotypy of their responses are the manifestation of an innate behavioral program.

Rodents exhibit a variety of defensive behaviors in response to innately aversive and conditioned cues, including flight, freezing, crouching, defensive threat, defensive attack, and burying of potentially threatening objects (Blanchard and Blanchard, 2008; Blanchard et al., 1986; Blanchard et al., 1998). The category of response elicited by a given cue depends on the context in which it is presented (Bolles and Collier, 1976; Bouton and Bolles, 1980; Pinel and Triet, 1978; Yilmaz and Meister, 2013), the nature of the conditioned stimulus (Karpicke et al., 1977; Pinel and Triet, 1978), and the ongoing behavioral state of the animal (Fentress, 1968a, b).

Applicant observed four stimulus-induced behaviors in this assay: flinch, ingress, egress bout and tremble. Applicant interpreted flinch in response to mild air puff as a startle response (Davis, 1984); ingress as a flight-like response, whose abrupt onset and selective release by looming visual stimuli resembles stimulus-selective flight in freely-moving animals (De Franceschi et al., 2016; Yilmaz and Meister, 2013); egress bout as exploration; and tremble as freezing. Indeed, while mice typically ingress in response to CS+ presentation (FIG. 5), in some cases animals also exhibit a selective tremble response to the aversive cue (FIGS. 5 and 7), an observation applicant has also made in video taken of freely moving animals during aversive conditioning (data not shown). Since mice produce these distinct behaviors (ingress, tremble) in response to an unchanging external stimulus, this assay may permit the investigation of the mechanism of action selection downstream of stimulus detection.

Novel stimuli typically trigger exploration (Berlyne, 1950) but can also evoke defensive behaviors. For instance, rats have been observed to avoid for hours an unfamiliar object placed in an otherwise familiar context (Chitty and Shorten, 1946; Shorten, 1954). Placing familiar food in a novel context inhibits feeding (novelty-induced hypophagia)—a phenomenon mitigated by anxiolytics (Dulawa and Hen, 2005). These results indicate that under some circumstances novelty may be aversive. When applicant presented novel, neutral odor stimuli to mice in the VBA device 1, they initially ingressed before habituating over repeated presentations. The VBA device 1 thus can measure the transition from novelty to familiarity (Cooke et al., 2015; Groves and Thompson, 1970; Horn, 1967). Moreover, since this novelty response is stimulus-specific, the VBA device 1 may also be employed as a stimulus discrimination assay that requires neither Pavlovian nor instrumental conditioning.

The VBA device 1 is compatible with standard electrophysiological and optical methods for measuring and perturbing neuronal activity. Since it measures ingress latency at a millisecond timescale it permits alignment of, and direct comparison with, neuronal dynamics. Such alignment to sharp transitions in behavioral state has proved fruitful in primate neurophysiology: for instance, alignment to the precise time of eye saccades indicating a perceptual decision permits the investigation of the neuronal events underlying a decision process (Roitman and Shadlen, 2002).

The VBA device 1 could be employed to model symptoms associated with a wide range of neurological and psychiatric disorders, including Depression, Alzheimer's disease, Parkinson's disease, Huntington's disease, Schizophrenia, Autism spectrum disorder, Stroke, Traumatic brain injury, Multiple Sclerosis, Amyotrophic lateral sclerosis, Muscular Dystrophy, Essential tremor, Transient tic disorder, Tourette's syndrome, Ataxia, Dyskinesias, and Dystonia.

The VBA device 1's high sensitivity in time and space permits it to measure motor deficits symptomatic of a diversity of neurological diseases, without the need for sophisticated videography equipment or data analysis by either complex algorithms or time/resource-intensive human scorers.

The VBA device 1 differs in several important respects from traditional assays. Since the VBA device 1 measures behavior unfolding at a millisecond timescale it permits alignment of, and direct comparison with, neuronal dynamics. In addition, in contrast to traditional assays which measure the activity of anxiolytic agents by introducing the animal into an innately aversive context (e.g. exposure to a predatory threat overhead), thereby inducing anxiety-like behavior (e.g. avoidance of the exposed location), the VBA device 1 employs neutral stimuli to assess the animal's pre-existing, internal baseline level of anxiety. This distinction is critical, since the circuit mechanisms that regulate anxiety may not be related to the circuits that mediate defensive responses to external predatory threats (e.g., Humans who suffer from anxiety do not require stressors, much less predatory threat, to experience anxious thoughts or exhibit anxiety related behavior). Therefore, modulation of defensive responses to predatory threats by a pharmacological agent may not be predictive of activity of this agent on internally-generated anxiety.

The VBA device 1 captures behavioral responses with millisecond precision, exploits a stereotyped behavior that requires no training, and is compatible with standard electrophysiological and optical methods for measuring and perturbing neuronal activity. Retreat in the VBA device 1 marks an abrupt behavioral transition that unfolds at a timescale similar to that of neuronal dynamics.

This precise timestamp permits alignment of behavioral state with underlying neuronal activity, as does the eye saccade in primate neurophysiology (Roitman and Shadlen, 2002).

In addition, while traditional assays listed above depend on voluntary exploration of a complex, aversive environment by the animal, the VBA device 1 relies on simple, highly reproducible sensory stimuli. Moreover, the closed-loop system that determines trial onset affords control over, and reproducibility of, the behavioral state of the animal immediately prior to each trial. In pilot experiments applicant has observed that the number of experiments required to observe a statistically significant effect is dramatically reduced in comparison to traditional assays. Applicant speculates that this is due either to a reduction in these two sources of variability (stimulus and pre-trial behavioral state) across animals, or to increased sensitivity of the assay.

As discussed, one drawback of traditional assays is that animals habituate to the aversive context; this renders it challenging to test an animal multiple times, and to perform longitudinal studies over time—e.g. to measure the efficacy of SSRIs that typically take several weeks to reach peak activity. This problem may be easily circumvented in the VBA device 1 by employing a different stimulus every time the animal is tested—thus requiring many fewer animals for a longitudinal study, and permitting within-animal comparisons across time. This also permits, as applicant have demonstrated in pilot experiments, the use of cross validation to eliminate any potential confounds due to variability across individuals.

In addition, the VBA device 1 does not rely on stressors such as exposure to predatory threat to induce anxious-like behavior, but rather probes the internal baseline anxiety level of the animal using neutral stimuli. Applicant speculates that this better models anxiety in human patients. The VBA device 1 further:

- Affords better control over both the stimulus and the pre-trial behavioral state of the animal.
- Requires fewer experiments to achieve comparable statistical power.
- Employs a Fine temporal scale that permits direct comparison of behavior with neural dynamics.
- Supports multiple tests in the same animal and longitudinal studies.

The VBA device 1 is trial-based and measures transitions in behavioral state that unfold over milliseconds, in contrast to traditional assays that measure location preference over a period of several minutes. This permits direct comparison with neural dynamics, which also unfold on a millisecond timescale, therefore supporting both correlative and causal investigation using the contemporary arsenal of tools for measuring and perturbing neural activity (large-scale electrophysiology and imaging, optogenetic activation and silencing).

The assay is easy to use; each experiment requires approximately 2 mn of setup by the technician and 10 mn of data acquisition, which is fully automated and does not require supervision, permitting experiments to run in parallel; the analysis is also fully automated (i.e. no human scoring of video).

Applicants anticipate that, in addition to implementing a novel rodent model of anxiety, the VBA device 1 could be employed to assay symptoms associated with a wide variety of neurological and psychiatric disorders, and that it would overcome some of the shortcomings of current rodent behavioral models.

Because the mouse stands inside a tube that is floating on a nearly frictionless, or low friction, track, the VBA device 1 captures extremely fine movements of the animal's body and limbs. For example, the animal's breathing cycle is clearly visible in the measurement of tube position, and subtle (low amplitude, high frequency) trembling of its body, difficult to resolve unless using high frame-rate video, is readily apparent in the laser signal (e.g. FIG. 2 and FIG. 7). The VBA device 1's high sensitivity in time and space would permit it to measure motor deficits symptomatic of a diversity of neurological diseases—this without the need for sophisticated videography equipment or data analysis by either complex algorithms or time/resource-intensive human scorers. Example applications follow:

- Tremor/involuntary movement/muscle twitch/chorea: head-fixing the animal in the VBA device 1 in open-loop mode would yield an assay of tremor and other involuntary movements in animals at rest, by simply recording the value detected by position sensor over time. Assay is sensitive enough to record breathing cycle, so tremor should be easy to catch (see, e.g., FIG. 2C). Alternatively in closed-loop mode the VBA device 1 could measure these deficits during active movement. In the closed-loop mode when the tube is retracted from the animal's body, the resistance exerted by the animal is measured by a force meter 50.

In wild-type mice, this signal decays smoothly, but uncontrolled movements would produce large deviations from this smooth decay. Compared to standard assays of motor deficits, which are primarily focused on locomotion or other alternating limb movements such as swimming or rotarod, control of the VBA device 1 requires coordinated movements of different muscle groups and motor patterns different from those involved in locomotion, and could provide a more sensitive assay of motor impairments associated with diverse diseases.

- Weakness: Wild-type mice invariably resist retraction of the tube away from the body, as measured by a force sensor 50 coupled to the tether 40 that retracts the tube. The animals are extremely motivated to do so and can generate up to four times their body weight in resistance. Two modes can be recorded: transient force (e.g., during initial response to pullback) a sustained force (e.g., >0.5 seconds), which seem to reflect different motor actions and may be under control of differently configured muscle groups and circuits. The assay thus records the strength with which the animal resists exposure, yielding a readout of animal strength. Importantly, the force with which the animal resists tube retraction is generated by the coordinated action of diverse limb and body wall muscles and so is a more comprehensive measure of strength (limb and core) than traditional assays, which focus on grip strength, which depends highly on the strength of the digits.

- Impaired coordination: Mice exhibit a highly stereotyped motor behavior in response to noxious air puff directed to the face, ingressing within approximately 20 milliseconds of puff onset via a coordinated movement of all four limbs. Impaired motor coordination would manifest itself in a decrease in tube velocity, an increase in the latency between puff onset and response, and an increase in variance in this latency. The stereotypy of this motor sequence, and the low variability in response latency both within and across animals render this a simple assay of motor coordination capable of detecting even subtle defects on the millisecond scale. Critically, despite its rapid expression and high stereotypy it requires no training.

- Impaired balance/overactive reflexes: As the air pressure within the VBA device 1's air bearings 30 is increased, the stability of the tube decreases due to a decrease in friction. Applicant has observed that a small subset of wildtype mice cannot control the tube under very low friction conditions, resulting in frequent bouts of oscillation in which the animal repeatedly overcorrects for small movements. Applicant expects that these oscillations would be much more prevalent in animals whose balance is impaired or who have overactive reflexes.

- Initiation of volitional movement: Simple measures of volitional movement (e.g. beam interruptions during open field activity) present interpretation challenges. More specific assays of akinesia in rodents. (e.g. rotarod, grid test) similarly assay only movement related to locomotion and, because they are difficult for the animal to perform, require some form of training—thus potentially engaging neural systems unrelated to those implicated in PD. Moreover, the fact that these tasks require skilled movement rather than movement that is typical for the organism (many animals fail to complete the minimum requirements of the task (e.g.

time spent on the rod/grid) and must be excluded from analysis) raises issues regarding interpretability and validity with respect to the typical movement disorders in human PD patients. Such volitional movement can be used to model Autism (e.g., whether the mouse comes out to investigate or stays inside the burrow).

Humans suffering from PD show deficits in voluntary movement initiation for even basic actions such as standing up or walking; thus a better assay in the rodent would focus on motor actions that are easy for the animal to perform and that that require no training.

The VBA device 1 in closed-loop mode could directly measure the frequency of volitional movement initiation by recording the number of spontaneous ingresses that mice produce during the inter-trial intervals in the absence of stimuli. The kinetics of this behavior are highly stereotyped, permitting comparison across individual events and across mice. Critically, the animals produce this stereotyped action without any training, so it is not necessary to rely on instrumental learning and the gradual honing of motor skills typically necessary to repeatedly perform low-variability actions.

Sensory/cognitive: Measurement of sensory detection and discrimination using short-term habituation; Measurement of long term memory using long-term habituation; using habituation rather than Pavlovian or instrumental paradigms to study sensory/cognitive features excludes circuits that orchestrate motor, motivational, consummatory, and 'task structure' learning—which could also be impacted in mouse models of PD and therefore present interpretation confounds.

Akinesia: a hallmark of Parkinson's disease is a reduced ability to initiate voluntary movement. Simple measures of locomotion (e.g. beam interruptions during open field activity) present interpretation challenges. More specific assays of akinesia in rodents (e.g. rotarod, grid test) similarly assay only movement related to locomotion and because they are difficult for the animal to perform require some form of training—thus engaging neural systems unrelated to those implicated in PD. Moreover, the fact that these tasks require skilled movement rather than movement that is typical for the organism (many animals fail to complete the minimum requirements of the task (e.g. time spent on the rod/grid) and must be excluded from analysis) hinder interpretability and validity with respect to the typical movement disorders in human PD patients. Humans suffering from PD show deficits in voluntary movement initiation for even mundane actions such as standing up or walking; thus a better assay in the rodent would focus on motor actions that are easy for the animal to perform (i.e. normal movements) that require no learning. The VBA device 1 in closed-loop mode could implement such an assay by measuring the frequency of spontaneous ingresses that mice produce during inter-trial intervals even in the absence of a stimulus. Applicant has been treating this behavior as a bug to be corrected (by pulling the animal back out during the ITI) but it could instead be exploited to measure the propensity of an animal to spontaneously initiate movement—and, critically, provide a millisecond scale timestamp of these events to permit direct comparison with and manipulation of the neural substrates that regulate movement initiation.

The VBA device 1 could also be employed to implement a more valid behavioral model of learned helplessness that does not rely on acute pain, fear, or life-threatening danger. Wild-type animals habituate to the contingencies of the VBA device 1 in closed-loop mode over a period of approximately 5-10 minutes (i.e. eventually cease spontaneous ingress and hold the burrow in the egress position for extended periods of time). Applicant anticipates that rodent models of depression will show more rapid habituation to these contingencies, i.e. yield to the contingencies of the closed-loop regime faster than wildtype animals—and conversely that drugs such as SSRIs will decrease the rate of habituation in wild-type mice. Critically, this assay of learned helplessness would not depend upon acute threat to the well-being of the animal, but simply measure the rate at which it submits to a "frustrating" but benign set of circumstances.

Sensory detection and discrimination can be directly measured in the VBA device 1 without any training, bypassing the confounds discussed in reference with Sensory deficits (detection, discrimination), in particular olfactory deficits, are an early indicator of the onset of Alzheimer's disease (AD), Parkinson's disease (PD) and Huntington's disease (HD) (e.g. FIG. 4).

By using only passive exposure to neutral stimuli and measuring behavioral evidence of habituation, the VBA device 1 can assay memory directly without any need for motivating and/or training the animal, bypassing confounds (e.g. a multi-day version of the experiment described in FIG. 4) discussed with reference to memory deficits, which are symptoms of Alzheimer's disease (AD), Parkinson's disease (PD), and cognitive decline associated with aging.

Neophobia (the extreme or irrational fear or dislike of anything novel or unfamiliar) is a hallmark of both Schizophrenia and Autism spectrum disorder (ASD). The VBA device 1 implements a sensitive assay of habituation to stimuli that requires no training or positive/negative reinforcers (e.g. FIG. 4). Applicant anticipates that rodent models of Schizophrenia and ASD will habituate more slowly to novel stimuli than wildtype animals. Since assays of neophobia (such as the open field test) typically rely on the animal's propensity to explore a potentially threatening environment, they do not permit disambiguation between fear of predators, and aversion to novelty. Additionally, the oddball paradigm (in which presentations of sequences of repetitive stimuli are infrequently interrupted by a deviant stimulus), which is commonly employed to assess schizophrenia and ASD patients has no analog in the rodent for lack of a clear behavior indicating detection of an oddball stimulus. The habituation experiment (FIG. 4) could be easily translated into an oddball paradigm that mirrors the one employed in humans.

The VBA device 1 establishes a causal relationship between the state of (a) neuronal network(s) and behavioral output, as an assay to examine the acquisition of information about the statistics of the world. In nature, an organism is required to sample its limited sensory space in order to estimate the statistics, and weigh the relative values, of the risks and rewards of its environment. The VBA device 1 recreates such a world in the laboratory such that the animal's behavior is easily interpretable and subject to minimal noise. Behavior is generally slow and noisy, especially in the laboratory; therefore two conditions must be satisfied: (1) the behavioral state and the network state must be relatable, i.e. measured and compared at a similar timescale, and (2) noise must be reduced to a minimum; what variation remains must be relatable to the state of the network. Both of these conditions are difficult to satisfy in standard laboratory assays which measure long-lasting states (e.g. freezing, escape, or choice between ports/arms)

that often relate poorly with what the animal is naturally skilled at doing. The VBA device 1 instead identifies easily-performed, short-latency, and short-lasting behavioral states, even if these are only transitions to subsequent, slower, more complex and longer-lasting states. The two conditions above would be satisfied by the following classes of behavior:
- initiation of an escape behavior in the presence of a threat (or predicted threat) from a predator
- initiation of an acquisition behavior in the presence of a reward (or predicted reward), while under pressure from a predator such that this threat forces rapid decision-making and action.

Placing the animal in such a context that it must continuously decide whether or not to enter/exit its "home" (VBA device 1) in order to maximize experimenter-generated rewards while evading experimenter-generated predators has at least the following advantages:

(A) The timescale of such behaviors lends itself to analysis alongside neuronal representation of the relevant sensory, cognitive and motor values, using the current analytical toolset available in systems neuroscience.

(B) Under such conditions, behavioral noise stands to be reduced because the expression of such a behavior is not a long, complex series of motor actions, or a binary state such as freezing or licking, but instead a continuous variable along a single dimension: position of animal relative to its safe haven. E.g.: the speed, frequency, or even dynamics characterizing how the animal enters or exits its safe haven could be instructive, especially under conditions in which predator threat and reward probability are approximately balanced and varied over a tight range; yet the underlying mechanisms governing that behavior would be masked by the measurement of binary variables such as freezing or licking, and interpreted under those measures as noise.

(C) Another potential source of behavioral noise in laboratory experiments is that mice are often forced to perform motor actions that are unnatural to them, for which they need to be trained extensively, sometimes against their natural inclinations. (E.g. running on a ball, sniffing at a port, pressing levers) Studies that rely on these motor behaviors as a readout for cognitive variables expose themselves to (1) animal-to-animal and trial-to-trial variability in the subject's ability to perform these unnatural and sometimes very difficult behaviors (both cognitively and kinetically) and (2) risk reporting signals related to the neuronal mechanisms that permit such complex motor behaviors, rather than understand the underlying cognitive question that is the principal target of the study.

Rather than teaching an animal to do "circus tricks", the VBA device 1 provides a solution to this source of noise by providing experimental contingencies around what it is the animal does naturally—what it is "built to do".

The VBA device 1 provides a simple assay to examine a broad class of problems that are central to behavioral, systems and circuits neuroscience:

- Innate behaviors driven by stereotypical stimuli that have been reinforced (positively or negatively) over the course of evolution—E.g. smelling/hearing/seeing prey, rewards, threatening conspecifics, mates.
- Learning and the underlying network/cellular plasticity that serves it: associating priorly neutral cues with predators, aversive stimuli or rewards.
- Encoding of probabilistic events by experimental generation of an environment in which the occurrence of rewards and punishments (and their relationship to sensory cues) is not deterministic but rather a function of stochastic processes.
- Flexibility in the encoding of probabilistic events in which the animal updates its model of the environment given changing conditions, or in a context-specific manner.
- Decision-making/action selection in which the animal has encoded the state of its environment at a given moment in time and must select which motor program to engage in response to it.
- Encoding of time in which the relationship between sensory variables and rewards/punishments can be varied according to rules in the time dimension, permitting a search for the representation of these rules and the mechanisms that produce them. E.g. a given priorly neutral cue could be made to predict a specific future time window during which a reward is available in the absence of a punishment/predator.

The animal inside the tube is in a baseline state characterized by calm, but alert sampling the environment. (The sampling may be in the olfactory, auditory and possibly visual modalities.) This relatively calm but alert baseline state is critical if the contingencies will result in value (positive or negative) being associated with priorly neutral cues.

- Rewards can be food or water (in restricted animals). Punishments can be standard laboratory unconditioned stimuli such as shock or air puff to the eye. Alternatively, and in order to (1) make the situation more naturalistic, (2) study aversion from threat rather than from pain, and (3) permit unimodal conditioning paradigms, naturally aversive stimuli such as predator odors can be employed as USs.
- Punishments/predators can be delivered such that they are only present when the animal exposes itself to them (establishing a relationship between the animal's state/position and its US—an operant contingency) or else be independent of its behavior (a Pavlovian conditioning contingency).
- Auditory USs are a very attractive option as they are easily controllable from the standpoint of experimental delivery and the resulting sensory representation. The sound of distressed conspecifics or predators may prove easier to deliver and interpret. This may prove an area of future expansion.

In addition, the virtual burrow assay device 1 may be used to:
- measure the dose dependence to an SSRI (e.g. fluoxetine) to assess its anxiolytic properties
- measure the dose dependence to agents that have succeeded in rodent assays of anxiety but failed to show activity in human clinical trials e.g. antagonists of corticotropin releasing factor (CRF) or Neurokinin 1 (NK1)
- measure the rate of ingress or egress to novel stimuli in a genetic mouse model of anxiety.
- genetically modified mouse can be used in connection with Parkinson's disease (e.g., determining whether symptoms in the mouse correspond to that which humans experience), and in connection with Alzheimer's disease, by, for example, using a genetically modified mouse in connection with the VBA device 1 to detect early signs of the disease
- automated rodent behavioral assay method for preclinical testing of anxiolytic drugs automated rodent behavioral assay for preclinical testing of drugs or therapies for other neurological disorders, method for studying burrowing mechanics in rodents research tool for identifying novel genes associated with neurological disorders diagnostic assay for identifying anxiety in different animal models diagnostic assay for identifying neurological and or psychiatric disorders in different animal models (including genetically modified animal models)

Figure 12:
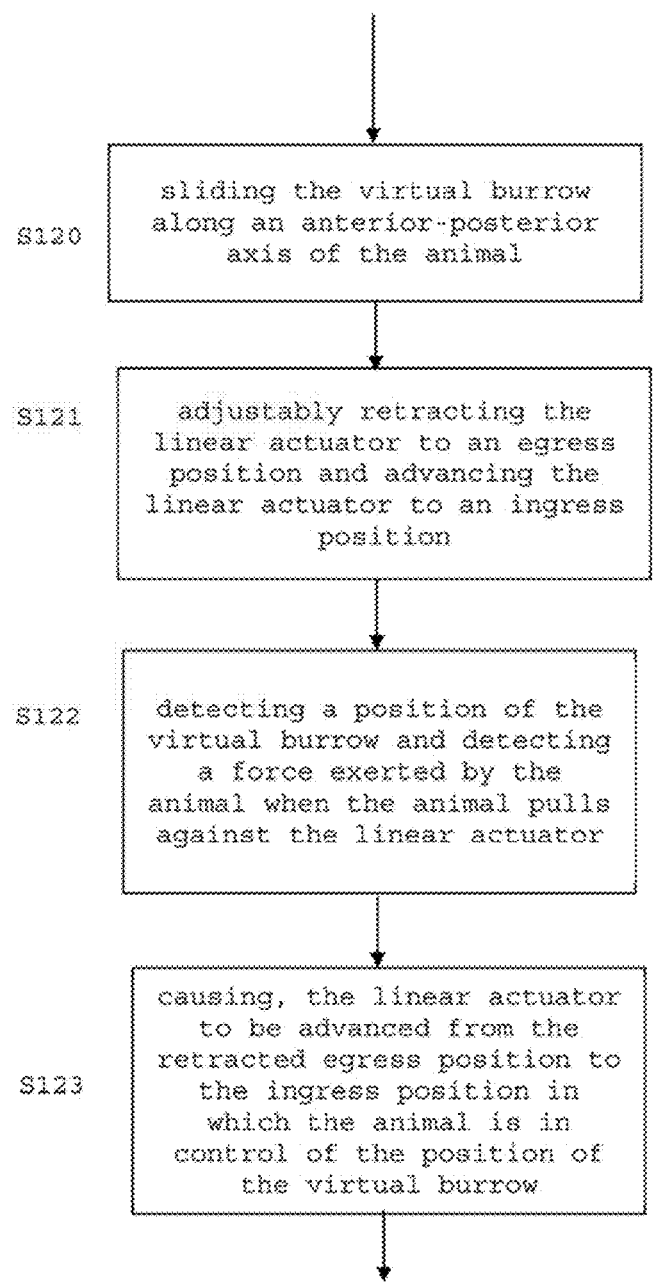
FIG. 12 shows a method of detecting behavioral responses of an animal to aversive stimuli.
Figure 13:
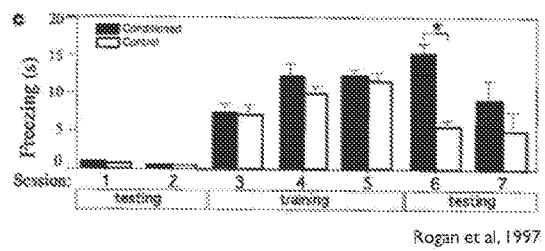
FIG. 13 shows standard measures of learned aversion.
Figure 13:
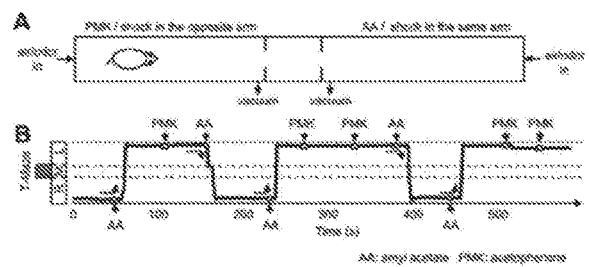

In addition, the virtual burrow assay device 1 may facilitate a method of testing whether (i) administering a predefined compound, or (ii) otherwise manipulating neuronal physiology of the animal (e.g., using optogenetic, chemogenetic or behavioral interventions), has an ameliorative effect on response of an animal, by subjecting the animal to such method shown in, for example, FIG. 12, of detecting behavioral responses of the animal, both with and without (i) administering the compound to the animal or (ii) otherwise manipulating the neuronal physiology of the animal, and determining the behavior response of the animal.

Additional applications of the VBA device 1 include:

psychophysics, including detection threshold and discrimination;

information-Seeking, including neophobia, neophilia and exploration learning/memory, including short-term habituation, long-term habituation, fear conditioning, sensory preconditioning, stimulus sequence learning, oddball paradigm motor function, including avoidance/flight, startle, trembling/freezing, limb and core strength, balance, tremor, involuntary movement, movement initiation and movement velocity.

In particular, short-term habituation and neophobia in the animals may be an assay for anxiety in human beings; short-term habituation, oddball paradigm, neophobia in the animals may be an assay for schizophrenia in human beings; neophobia and movement initiation in the animals may be an assay for obsessive-compulsive disorder in human beings; detection threshold, short-term habituation, neophobia and exploration in the animals may be an assay for autism-spectrum disorder in human beings; detection threshold, short-term habituation, long-term habituation, balance, tremor, movement initiation and movement velocity in the animals may be an assay for Parkinson's disease in human beings; detection threshold and long-term habituation in the animals may be an assay for Alzheimer's disease in human beings; detection threshold, balance, tremor and involuntary movement may be an assay for Huntington's disease in human beings; short-term habituation and involuntary movement in the animals may be an assay for Tourette syndrome in human beings; and limb and core strength in the animals may be an assay for muscular dystrophy, amyotrophic lateral sclerosis and multiple sclerosis in human beings.

The VBA device 1 can be used as an efficacy test for drugs, administered to the mouse, and based on data collected from the mouse's behavior, conclusions can be drawn leveraging the data, and such conclusions can be applied to humans. Different drugs may cause different reactive behavior of the mouse, as determined by the inventive VBA device 1 discussed in this application.

As discussed, while conventional approaches have relied on qualitative tests (e.g., Yes or No relative to a threshold), the VBA device 1 of the present application is advantageously a quantitative measurement of the animals reaction in the laboratory.

Ongoing experiments in the laboratory will determine whether the Virtual Burrow Assay better predicts activity in the clinic for small molecules such as NK1 antagonists.

The virtual burrow assay device 1 may be a part of a system that comprises one or more of the following: a stimulus delivery device, analog-to-digital acquisition board, software for behavioral control, stimulus control and data acquisition, disposable burrows (one per session), and disposable or re-usable head plates for head fixation (one per mouse).

This invention will be better understood by reference to the Experimental Details which follow, but those skilled in the art will readily appreciate that the specific experiments detailed are only illustrative of the invention as defined in the claims which follow thereafter.

Experimental Details

Table 1 shows the animals that were used in this study.

TABLE 1

Animals used in this study

| Animal number | Age at surgery | Age at expt. | Data | Notes |
|---|---|---|---|---|
| 2016082205 | 11 wks | 19 wks | Air puff, FIG. 2 | — |
| 2016082206 | 11 wks | 18 wks | Air puff, FIG. 2 | — |
| 2016082207 | 11 wks | 18 wks | Air puff, FIG. 2 | The representative example of flinch (FIG. 2B) is taken from this animal. |
| 2016071401 | 15 wks | 21 wks | Visual stimuli, FIG. 3 | Expanding disk |
| 2016072401 | 16 wks | 21 wks | Visual stimuli, FIG. 3 | EXpanding disk |
| 2016072702 | 17 wks | 21 wks | Visual stimuli, FIG. 3 | Expanding disk |
| 2016081901 | 10 wks | 11 wks | Visual stimuli, FIG. 3 | Receding disk |
| 2016081902 | 10 wks | 11 wks | Visual stimuli, FIG. 3 | Receding disk |
| 2016081903 | 10 wks | 11 wks | Visual stimuli, FIG. 3 | Receding disk |
| 2015111301 | 15 wks | 56 wks | Visual stimuli, FIG. 3 | Sweeping disk |
| 2015111602 | 12 wks | 52 wks | Visual stimuli, FIG. 3 | Sweeping disk |
| 2015111701 | 12 wks | 52 wks | Visual stimuli, FIG. 3 | Sweeping disk |
| 2016082302 | 11 wks | 18 wks | Odor habituation, FIG. 4 | O1: Limonene O2: Octanal O3: Hexenol |
| 2016082401 | 14 wks | 21 wks | Odor habituation, FIG. 4 | O1: Octanal O2: Hexenol O3: Limonene |

TABLE 1-continued

Animals used in this study

| Animal number | Age at surgery | Age at expt. | Data | Notes |
|---|---|---|---|---|
| 2016082402 | 14 wks | 21 wks | Odor habituation, FIG. 4 | O1: Hexenol<br>O2: Octanal<br>O3: Limonene |
| 2016082404 | 14 wks | 21 wks | Odor habituation, FIG. 4 | O1: Hexenol<br>O2: Octanal<br>O3: Limonene |
| 2016082405 | 14 wks | 21 wks | Odor habituation, FIG. 4 | O1: Octanal<br>O2: Hexenol<br>O3: Limonene |
| 2016082006 | 11 wks | 21 wks | Aversive odor learning, FIG. 5 | — |
| 2016082005 | 11 wks | 21 wks | Aversive odor learning, FIG. 5 | — |
| 2016082003 | 11 wks | 21 wks | Aversive odor learning, FIG. 5 | — |
| 2016082001 | 11 wks | 21 wks | Aversive odor learning, FIG. 5 | — |
| 2016071401 | 15 wks | 30 wks | Aversive odor learning, FIG. 5 | Animal also used for expanding disk experiment |
| 2016081903 | 10 wks | 20 wks | Aversive odor learning, FIG. 5 | Animal also used for receding disk experiment |
| 2016081902 | 10 wks | 20 wks | Aversive odor learning, FIG. 5 | Animal also used for receding disk experiment |
| 2016081901 | 10 wks | 20 wks | Aversive odor learning, FIG. 5 | Animal also used for receding disk experiment |
| 2016082602 | 14 wks | 23 wks | Aversive odor learning, FIG. 5 | — |

Materials and Methods

Subjects and Surgery

All procedures were approved by the Animal Care and Use Committee (protocol AC-AAAI8650). 10-17-week old male C57BL/6J mice (Jackson laboratories, Bar Harbor, Me.) were fitted with a titanium head plate (27.4 mm×9.0 mm×0.8 mm, G. Johnson, Columbia University). Animals were anesthetized with isoflurane (3% induction, 1.5-2% maintenance) and placed within a stereotaxic frame (David Kopf Instruments, Tujunga, Calif.) on a feedback-controlled heating pad (Fine Science Tools, Foster City, Calif.). Carprofen (5 mg/kg) was administered via subcutaneous injection as a preoperative analgesic and bupivacaine (2 mg/kg) was delivered underneath the scalp to numb the area of the incision. The skull was exposed, cleaned with sterile cotton swabs and covered in a thin layer of cyanoacrylate adhesive (Krazy Glue, Elmer's Products, Atlanta, Ga.). After applying a coating of adhesive luting cement (C&B-Metabond, Parkell, Inc., Edgewood, N.Y.) onto the layer of cyanoacrylate adhesive, the titanium head plate was lowered atop the skull and secured with additional application of luting cement. The headplate was centered about the body's anterior/posterior axis and equally spaced between bregma and lambda. For mice exposed to visual stimuli head plate position was sufficiently posterior to prevent occlusion of the visual stimuli by the head plate. Mice were allowed at least one full week and typically greater than 4 weeks to recover before any testing was performed (Table 1). All animals were singly housed on a 12 hour/12 hour light/dark cycle. All experiments were performed during the animals' dark phase.

Design of the Virtual Burrow Assay

The Virtual Burrow Assay (VBA) device 1 may comprise a tube enclosure (virtual burrow 10) constructed of a cardboard or 3D-printed polylactic acid tube (45.5-mm inner diameter, 49-mm outer diameter, 7-cm long). A 4-cm long, 0.5-mm diameter wooden rod is adhered to the front opening of the tube, 1 cm from the base, in order for animals to grip and rest their forelimbs. For the aversive learning experiments (FIG. 5) the tube included a 1-cm wide extension spanning approximately ⅓ of the tube's bottom circumference. The virtual burrow 10 is affixed to air bearings 30 (e.g., New Way Air Bearings, Aston, Pa.) that slide along two precision oriented rails, parallel to the anterior-posterior axis of the animal's body (design and assembly: T. Tabachnik, ZMBBI Advanced Instrumentation, Columbia University; Fabrication: Ronal Tool Company, Inc., York, Pa.; FIG. 1A, right and FIG. 1B). The animal may be head-fixed via custom-machined stainless steel head plate holders 20 (G. Johnson, Columbia University) that secure the titanium headplate. The entire VBA device 1 may rest atop an adjustable platform (Thorlabs, Newton, N.J.) to permit precise translation of the position of the tube with respect to the head. With its head thus secured, the animal's body rests freely within the virtual burrow, its forepaws resting on the horizontal bar placed at the burrow's threshold, its hind limbs gripping the burrow's interior.

A linear actuator 70 (e.g., Part number: L12-30-50-12-I, Firgelli Automations, Ferndale, Wash.), tethered to the virtual burrow 10 with fishing line (0.15-mm diameter nylon tippet, 4.75 pound test, Orvis, Sunderland, Vt.) constrains how far the animal may ingress into the burrow at any given time (FIG. 1B,C). This parameter can be manually or programmatically varied over the course of the experiment. A force sensor 50 (e.g., Futek FSH02664 load cell with Futek QSH00602 signal conditioner, Futek, Irvine, Calif.) reports whether, and how strongly, the animal is pulling against the linear actuator 70 in its effort to ingress. Upon head-fixation in the VBA device 1, mice invariably ingress as far as the linear actuator 70 command position permits, as indicated by continuous force measured by the force sensor 50. When the linear actuator 70 retracts the burrow away from the ingress position (egress position, 10-20 mm posterior to ingress position), mice resist the translation, pulling against the tether 40 in an effort to move the burrow back up around their body. This effort typically generates between 40 and 100 g of force, corresponding in some cases to more than three times animal's own body weight. Applicant have not observed any mice that fail to resist retraction of the virtual burrow 10.

A laser displacement sensor 60 (e.g., Part number: ILD1302-50, Micro-Epsilon, Dorfbach, Germany) is positioned so as to measure the linear displacement of the tube along its axis of motion. The laser displacement sensor 60 is aimed at a flag affixed to the horizontal bar that joins the air bearings 30, whose position moves with the virtual burrow 10. The readout of the laser displacement sensor 60 yields a continuous, time-dependent, one-dimensional variable. It is this quantity—how far the animal has pulled the virtual burrow 10 around its body—that tracks ingress in response to a given cue.

For all experiments reported here the analog voltage signals from the laser displacement sensor and the force meter 50 were acquired and digitized at 10 kHz using a Cerebus Neural Signal Processor (Blackrock Microsystems, Salt Lake City, Utah).

Trial Structure and Closed Loop Control

Before each trial the control system pulls the virtual burrow 10 back to the egress position and waits until the force meter 50 indicates that the animal has ceased to resist burrow retraction (FIG. 1D). The linear actuator 70 is then advanced to the ingress position, slackening the tether 40 and permitting free movement of the burrow. If the animal spontaneously ingresses prior to stimulus onset, as measured by the laser displacement sensor 60, the trial is aborted, the burrow is again retracted to the egress position, and the sequence repeats. Once the mouse has maintained the free, egress position without attempting to ingress within a specified duration, and has maintained the standard deviation of the tube position below a user-specified threshold for a specified delay period, the stimulus is delivered. During stimulus presentation, and a set duration following stimulus offset, the control system is switched to open loop, permitting the mouse to pull the burrow up to the ingress position if it wishes.

The burrow position (measured by the laser displacement sensor 60), burrow force (measured by the force sensor 50), and the servo position (state of the linear actuator 70) are analog inputs to a National Instruments card with analog and digital in/out (Part number: USB-6008, National Instruments, Austin, Tex.). The servo position was in turn controlled by the National Instruments card (FIG. 1C, FIG. 1D).

Prior to testing, naïve mice are head-fixed in the VBA device 1 and given 5-10 mn to acclimate to the contingencies in open loop (free movement of the burrow). Without exception, mice maintained the burrow in the ingress position throughout this habituation period. Then they are acclimated to the closed loop regime; after an initial period of sustained struggle to maintain the burrow in the ingress position, mice cease resisting and eventually consent to holding the burrow in the egress position even after the linear actuator 70 has advanced, slackening the tether 40 and granting the mouse control over the burrow. The duration of the closed-loop acclimation period varied across mice (5-20 mn). Trial blocks begin once the animal reliably holds the burrow in the egress position for >30 sec between spontaneous ingresses. Trial initiation is delayed until after the mouse has held the burrow in the egress position with minimal movement for several seconds so as to ensure that the animal is in a comparable behavioral state prior to each trial.

Air Puff Stimulus

Animals were head-fixed within the VBA device 1 and permitted to acclimate to head fixation for 5 mn with the VBA device 1 on open loop. The VBA device 1 was then switched to the closed loop configuration and air puff stimuli were delivered once the animal readily gave trials. An 18-gauge, blunt syringe needle delivered air puff stimuli to generate both flinch (FIG. 2D, needle tip 15 cm from nose, air pressure 2 PSI, puff duration 20 msec) and ingress (FIG. 2B, needle tip 2 mm from nose, air pressure 80 PSI, puff duration 200 msec, ITI 180 sec, 15 trials per animal).

To determine latency to air puff, applicant subsequently measured the time between the TTL pulse controlling valve opening and the displacement of a small polystyrene weighing boat placed 2 mm distant from the blunt syringe needle (data not shown). Applicant then subtracted the time between TTL pulse and measured displacement to determine the latency between TTL command and air puff stimulus at the nose. To account for variability in the position of the nose of the mouse with respect to the needle tip, applicant varied the precise location of the syringe needle over a range of distances similar to variability in distance between the syringe needle and the animal's nose across experiments. Applicant observed negligible variability in latencies across this distance range, demonstrating that this is not the reason why different animals exhibit different mean response latencies (FIG. 2D).

For this and all experiments, a background of acoustic white noise (1000-45000 Hz; approximately 7 dB) was played throughout. The VBA device 1 was placed within a custom-made sound attenuating chamber resting on an air table (TMC, Peabody, Mass.). For the experiments studying responses to visual stimuli, the chamber was open to accommodate the bulk of the display screen but the lights in the room were off and the door was closed.

Visual Stimulus

For experiments examining responses to visual stimuli, animals were acclimated to head fixation within the VBA device 1 for 3 mn in the open loop configuration. Following a subsequent 10-mn habituation period with the VBA device 1 in the closed loop configuration, the animal was again permitted to freely ingress in open loop for 3-5 mn. The VBA device 1 was then returned to the closed loop configuration and once the animal did not spontaneously ingress for periods greater than 30 sec (typically after approximately 3 mn) visual stimuli were delivered.

The visual stimuli employed were based on those described in de Francheschi et al. (2016). Briefly, the stimuli were presented on a Dell 1707FP 17" LCD monitor, 1280×1024, 60 Hz, elevated 30 cm and centered above the animal's head. The three stimuli, generated using the Psychophysics Toolbox 3 in MATLAB (Mathworks, Natick, Mass.), consisted of a black disk presented against a grey background: expanding disk ("loom"), widening from 2° to 50° over 250 msec, holding the 50° disk for 500 msec; contracting disk ("recede"), diminishing from 50° to 2° over 250 msec, holding the 2° disk for 500 msec; and sweeping disk ("sweep"), a 5° disk sweeping smoothly across the diagonal of the screen at a rate of 21°/sec. In order to permit synchronization of stimulus timing with burrow position measurement, the software controlling the visual stimulus also controlled a PWM signal (generated by an Arduino Uno, Adafruit, New York, N.Y.; acquired as an analog voltage input digitized at 10 KHz simultaneous to the position and force signals) that encoded the identity and timing of the visual stimuli.

Applicant divided nine mice into three groups of three animals, one group per stimulus type, and presented each mouse only one of the stimulus types in a single session of five stimulus presentations separated by a 10-mn ITI. The data for each stimulus type are pooled across animals for each group.

Odor Stimulus

Applicant used a custom built olfactometer 80 to deliver odor stimuli, although an off the shelf olfactometer may be used. Briefly, a nose port constructed of polyether ether ketone (PEEK) was placed approximately 1 mm away from the animal's nose. When no odor stimulus was given, the port delivered a steady stream of air (1 liter per minute, controlled by a mass flow controller, GFCS-010201 from Aalborg, Orangeburg, N.Y.) that had bubbled through a 50-ml glass bottle containing 15 ml dipropylene glycol (DPG, Part number: D215554, Sigma-Aldrich, St. Louis, Mo.). To deliver an odor stimulus, a four-way valve (Part number: LSH360T041, NResearch Inc., West Caldwell, N.J.) routed the air stream to exhaust, replacing it with a stream of odorized air; the odor stimulus was switched off by the four-way valve routing the odorized air back to exhaust. Monomolecular odorants (cis-3-Hexen-1-ol, catalog number W256307; (R)-(+)-Limonene, catalog number 183164; Octanal, catalog number 05608 all from Sigma-Aldrich, St. Louis, Mo.) were dissolved in 15 ml DPG at a concentration of 2% volume/volume in separate 50-ml glass bottles. After passing through the nose port all gas was routed to a photo-ionization detector (miniPID, Aurora Scientific, Aurora, ON, Canada) to permit constant monitoring of odorant concentration. To avoid contamination, all material in contact with the odorized air stream was constructed in either Teflon, Tefzel, or PEEK. The flow of the air and odor streams were equalized before each experiment (using mass flow meter GFMS-010786 from Aalborg, Orangeburg, N.Y.) and the tubing carrying the two streams from the four way valve was set to equal length and impedance to minimize variation in flow rate upon switching between the air and odor streams.

Odor Habitation

For odor habitation experiments, animals (five mice) were head-fixed in the VBA device 1 and allowed to acclimate in the open loop configuration for 5 mn. The VBA device 1 was then set to closed loop for 10-15 mn. After habitation to the VBA device 1, the animal was then presented with odor stimuli with the VBA device 1 in the closed loop regime. First, Odor 1 was presented 15 times. Then, a second odor, Odor 2, was introduced and the two odors were presented 15 times each, pseudo-randomly interleaved within blocks in which each of the two odors were presented in every block. Finally, a third odor, Odor 3, was added and all three odors were presented in 15 final blocks of three trials each. Each odor stimulus was presented once per block. All odor stimuli were 8 sec in duration and the ITI was 40 sec. Limonene, Octanal, and Hexenol were used as odor stimuli with different animals receiving different odors for the Odor 1, Odor 2, and Odor 3 stimuli (Table 1).

Odor-Shock Conditioning and Testing.

Day 1: Pre-Test.

Animals used in odor-conditioning experiments were first habituated to the three odor stimuli employed (CS+: Limonene, CS−: Hexenol, O3:Octanal). Animals were placed within the VBA device 1 and acclimated to head fixation for 5 mn with the VBA in open loop, after which the VBA device 1 was switched to closed loop for 10 mn. Following the 10-mn closed loop acclimation period, the VBA device 1 was restored to the open loop configuration for 5 mn to permit the animal to freely ingress before testing, and then returned to closed loop immediately before commencing odor stimulus delivery. Odor stimuli (8-sec duration) were presented in 10 blocks of three pseudo-randomly interleaved trials (60-sec ITI) such that each stimulus was presented once per block. Following completion of the 10 stimulus blocks, animals were immediately removed from the VBA device 1 and returned to their home cage.

Day 2: Conditioning.

Conditioning was performed one day after odor habituation. A fear conditioning box 11 (e.g., 14.2-mm wide, 16.2-mm long, 12.6-mm high, Med Associates, Fairfax, Vt.) was employed. Under conditions of darkness with an acoustic background of white noise, mice were placed within the fear conditioning box 11 on the open, gloved hand of the experimenter. Once the animal had freely entered the fear conditioning box 11, the door was closed and the animal was allowed to acclimate for 5 mn. Eight blocks of CS+ and CS− odor stimuli were presented in pairs of pseudo-randomly interleaved trials. The odor stimuli were 10 sec in duration with a 5-mn ITI. During the final 2 sec of presentation of the CS+ stimulus only, the floor of the fear conditioning box 11 was electrified (intensity 0.70-0.73 mAmp). Upon completion of all 8 trials, the mouse was permitted to recover for 5 mn in the fear conditioning box 11 and then returned to its home cage.

Day 3: Test.

One day after conditioning animals were returned to the VBA device 1 to test responses to all odor stimuli. Test was identical to pre-test except that eleven stimulus blocks were presented.

Statistics

To determine whether responses in the VBA device 1 differed across experimental conditions, applicant asked whether the likelihood of ingress was larger in one condition than another. For the purposes of this test applicant define an ingress as a maximum change in burrow position greater than a given threshold (here 0.75-0.85 mm; the results of the statistical tests are robust to the choice of threshold; see FIGS. 5 and 6). For each condition applicant pooled all ingress responses across mice and used a two-proportion z-test with the null hypothesis that the probability of ingress in the tested condition was less than or equal to the probability of ingress in the other condition. One star (*) indicates $p<0.05$, two stars () indicate $p<0.01$, and three stars (*) indicate $p<0.001$.

REFERENCES

Berlyne, D. E. (1950). Novelty and curiosity as determinants of exploratory behaviour. British Journal of Psychology General Section 41, 68-80.

Birke, L. I., D'Udine, B., and Albonetti, M. E. (1985). Exploratory behavior of two species of murid rodents, *Acomys cahirinus* and *Mus musculus*: a comparative study. Behavioral and Neural Biology 43, 143-161.

Blanchard, D. C., and Blanchard, R. J. (2008). Defensive behaviors, fear, and anxiety. In Handbook of Anxiety and Fear, R. J. Blanchard, D. C. Blanchard, G. Griebel, and D. Nutt, eds. (Amsterdam: Elsevier), pp. 63-79.

Blanchard, R. J., and Blanchard, D. C. (1989). Antipredator defensive behaviors in a visible burrow system. Journal of Comparative Psychology 103, 70-82.

Blanchard, R. J., Flannelly, K. J., and Blanchard, D. C. (1986). Defensive behavior of laboratory and wild *Rattus norvegicus*. Journal of Comparative Psychology 100, 101-107.

Blanchard, R. J., Hebert, M. A., Ferrari, P. F., Palanza, P., Figueira, R., Blanchard, D. C., and Parmigiani, S. (1998). Defensive behaviors in wild and laboratory (Swiss) mice: the mouse defense test battery. Physiology & Behavior 65, 201-209.

Bolles, R. C., and Collier, A. C. (1976). The effect of predictive cues on freezing in rats. Animal Learning & Behavior 4, 6-8.

Bouton, M. E., and Bolles, R. C. (1980). Conditioned fear assessed by freezing and by the suppression of three different baselines. Animal Learning & Behavior 8, 429-434.

Chitty, D., and Shorten, M. (1946). Techniques for the study of the Norway rat (*Rattus norvegicus*). Journal of Mammalogy 27, 63-78.

Cooke, S. F., Komorowski, R. W., Kaplan, E. S., Gavornik, J. P., and Bear, M. F. (2015). Visual recognition memory, manifested as long-term habituation, requires synaptic plasticity in V1. Nat Neurosci 18, 262-271.

Davis, M. (1984). The mammalian startle response. In Neural Mechanisms of Startle Behavior, R. C. Eatron, ed. (New York: Plenum Press), pp. 287-342.

De Franceschi, G., Vivattanasarn, T., Saleem, A. B., and Solomon, S. G. (2016). Vision Guides Selection of Freeze or Flight Defense Strategies in Mice. Current Biology 26, 2150-2154.

Domenici, P., and Blake, R. W. (1991). The kinematics and performance of the escape response in the angelfish (*Pterophyllum eimekei*). Journal of Experimental Biology 156, 187-205.

Dulawa, S. C., and Hen, R. (2005). Recent advances in animal models of chronic antidepressant effects: the novelty-induced hypophagia test. Neuroscience & Biobehavioral Reviews 29, 771-783.

Estes, W. K., and Skinner, B. F. (1941). Some quantitative properties of anxiety. Journal of Experimental Psychology 29, 390.

Fentress, J. C. (1968a). Interrupted ongoing behaviour in two species of vole (*Microtus agrestis* and *Clethrionomys britannicus*). I. Response as a function of preceding activity and the context of an apparently "irrelevant" motor pattern. Anim Behav 16, 135-153.

Fentress, J. C. (1968b). Interrupted ongoing behaviour in two species of vole (*Microtus agrestis* and *Clethrionomys britannicus*). II. Extended analysis of motivational variables underlying fleeing and grooming behaviour. Anim Behav 16, 154-167.

Groves, P. M., and Thompson, R. F. (1970). Habituation: a dual-process theory. Psychol Rev 77, 419-450.

Horn, G. (1967). Neuronal mechanisms of habituation. Nature 215, 707-711.

Karpicke, J., Greg, C., Peterson, G., and Hearst, E. (1977). Signal location and positive versus negative conditioned suppression in the rat. Journal of Experimental Psychology: Animal Behavior Processes 3, 105-118.

Pinel, J. P., and Triet, D. (1978). Burying as a defensive response in rats. Journal of Comparative and Physiological Psychology 92, 708.

Roitman, J. D., and Shadlen, M. N. (2002). Response of neurons in the lateral intraparietal area during a combined visual discrimination reaction time task. Journal of Neuroscience 22, 9475-9489.

Shorten, M. (1954). The reaction of the brown rat towards changes in its environment. Control of rats and mice 2, 307-334.

von Uexküll, J. (1957). A Stroll Through the Worlds of Animals and Men: A Picture Book of Invisible Worlds. In Instinctive Behavior: The Development of a Modern Concept, C. H. Schiller, ed. (New York: New York: International Universities Press, Inc.), pp. 5-80.

Walther, F. R. (1969). Flight behaviour and avoidance of predators in Thomson's gazelle (Gazella thomsoni Guenther 1884). Behaviour 34, 184-220.

Yilmaz, M., and Meister, M. (2013). Rapid innate defensive responses of mice to looming visual stimuli. Current Biology 23, 2011-2015.

What is claimed is:

1. A virtual burrow assay device for detecting behavioral responses of an animal which typically inhabits a burrow, based on entering (ingress) or exiting (egress) a virtual burrow, the virtual burrow assay device comprising:
   a virtual burrow configured to slide along an anterior-posterior axis of the animal;
   a head stabilizer to which the head of the animal is fixed, the head-fixed animal being permitted to egress out of and ingress into the virtual burrow;
   a port for delivering stimuli and/or rewards that is coupled to the virtual burrow, the animal being required to egress in order to approach and/or investigate the source of the stimulus and/or reward;
   a linear actuator which is coupled to the virtual burrow and configured to be adjustably retracted to an egress position along an axis of movement of the virtual burrow and to be advanced to an ingress position along the axis of movement of the virtual burrow;
   a position sensor to detect a position of the virtual burrow and a force sensor to detect a force exerted by the animal against the linear actuator, when the linear actuator is in the egress position; and
   a controller to cause, based on the position detected by the position sensor and the force detected by the force sensor, the linear actuator to be advanced from the retracted egress position to the ingress position in which the animal is in control of the position of the virtual burrow.

2. A virtual burrow assay device according to claim 1, wherein the linear actuator is coupled to the virtual burrow via a tether that is disposed to be slackened when the linear actuator is advanced to the ingress position to free the animal to ingress, and wherein
   the force sensor detects the force exerted by the animal against the linear actuator when the animal pulls on the tether.

3. A virtual burrow assay device according to claim 1, wherein the virtual burrow is constrained by near-frictionless or low friction air bearings that slide along respective precision oriented rails, in a sliding direction parallel to the anterior-posterior axis of the animal.

4. A virtual burrow assay device according to claim 1, wherein the controller detects the behavioral response of the animal based on at least one of the position detected by the position sensor and the force detected by the force sensor.

5. A virtual burrow assay device according to claim 1, wherein the controller detects the behavioral response of the animal based on a time period between the stimulus being delivered to the animal and the animal ingressing into the virtual burrow in response to the stimulus.

6. A virtual burrow assay device according to claim 5, wherein the stimulus is an aversive stimulus.

7. A virtual burrow assay device according to claim 5, wherein the stimulus is a neutral stimulus.

8. A virtual burrow assay device according to claim 5, wherein the stimulus is a positive stimulus and/or a rewarding stimulus.

9. A virtual burrow assay device according to claim 5, wherein the stimulus is a socially relevant stimulus.

10. A method of detecting behavioral responses of an animal based on the animal entering (ingress) or exiting (egress) a virtual burrow, using a virtual burrow assay device including the virtual burrow, a head stabilizer, a controller, a linear actuator, a position sensor and a force sensor, the method comprising:
- sliding the virtual burrow along an anterior-posterior axis of the animal, the animal being head-fixed to a head stabilizer and being permitted to egress out of and ingress into the virtual burrow;
- delivering stimuli and/or rewards via a port that is coupled to the virtual burrow, the animal being required to egress in order to approach and/or investigate the source of the stimulus and/or reward;
- adjustably retracting, by the controller, the linear actuator which is coupled to the virtual burrow to an egress position along an axis of movement of the virtual burrow and advancing the linear actuator to an ingress position along the axis of movement of the virtual burrow;
- detecting, via the position sensor, a position of the virtual burrow and detecting, via the force sensor, a force exerted by the animal against the linear actuator, when the linear actuator is in the egress position; and
- causing, by the controller and based on the position detected by the position sensor and the force detected by the force sensor, the linear actuator to be advanced from the retracted egress position to the ingress position in which the animal is in control of the position of the virtual burrow.

11. A method of testing whether (i) administering a pre-defined compound or (ii) otherwise manipulating neuronal physiology of the animal has an ameliorative effect on the behavioral responses of the animal which comprises subjecting the animal to the method of claim 10, both with and without (i) administering the compound to the animal or (ii) otherwise manipulating the neuronal physiology of the animal, and determining the behavioral responses of the animal.

12. The method according to claim 10, wherein the linear actuator is advanced from the retracted egress position to the ingress position when the controller determines that the position detected by the position sensor is less than a predetermined position threshold and the force detected by the force sensor is less than a predetermined force threshold.

13. The method according to claim 10, further comprising delivering the stimulus to the animal in response to the controller determining that the position of the virtual burrow has not exceeded a predetermined threshold position for a predetermined amount of time after the animal has egressed the virtual burrow, when the linear actuator is in the ingress position in which the animal is in control of the position of the virtual burrow.

14. The method according to claim 10, wherein the detected behavioral responses are indicative of short-term habituation and neophobia of the animal, and the detected behavioral responses are employed as an assay for anxiety in a human subject.

15. The method according to claim 10, wherein the detected behavioral responses of the animal correspond to at least one of the following (i) are indicative of short-term habituation, oddball paradigm, and neophobia in the animal, and are employed as an assay for schizophrenia in a human subject; (ii) are indicative of neophobia and movement initiation of the animal, and are employed as an assay for obsessive-compulsive disorder in a human subject; and (iii) are indicative of a detection threshold, short-term habituation, neophobia and exploration of the animal, and are employed as an assay for autism spectrum disorder in a human subject.

16. The method according to claim 10, wherein the detected behavioral responses of the animal correspond to at least one of the following (i) are indicative of detection threshold, short-term habituation, long-term habituation, balance, tremor, movement initiation and movement velocity of the animal, and are employed as an assay for Parkinson's disease in a human subject; and (ii) are indicative of long-term habituation of the animal, and are employed as an assay for Alzheimer's disease in a human subject.

17. The method according to claim 10, wherein the detected behavioral responses of the animal are indicative of detection threshold, balance, tremor and involuntary movement of the animal, and the detected behavioral responses are employed as an assay for Huntington's' disease in a human subject.

18. The method according to claim 10, wherein the detected behavioral responses of the animal are indicative of short-term habituation and involuntary movement of the animal, and the detected behavioral responses are employed as an assay for Tourette syndrome in a human subject.

19. The method according to claim 10, wherein the detected behavioral responses of the animal are indicative of limb and core strength of the animal, and the detected behavioral responses are employed as an assay for at least one of muscular dystrophy, amyotrophic lateral sclerosis and multiple sclerosis in a human subject.

20. A virtual burrow assay device for detecting behavioral responses of an animal which typically inhabits a burrow, the virtual burrow assay device comprising:
- a virtual burrow configured to slide along an anterior-posterior axis of the animal;
- a head stabilizer to which the head of the animal is fixed, the head-fixed animal being permitted to egress out of and ingress into the virtual burrow;
- a linear actuator which is coupled to the virtual burrow and configured to be adjustably retracted to an egress position along an axis of movement of the virtual burrow and to be advanced to an ingress position along the axis of movement of the virtual burrow;
- a position sensor to detect a position of the virtual burrow and a force sensor to detect a force exerted by the animal against the linear actuator, when the linear actuator is in the egress position; and
- a controller to cause, based on the position detected by the position sensor and the force detected by the force sensor, the linear actuator to be advanced from the retracted egress position to the ingress position in which the animal is in control of the position of the virtual burrow.

* * * * *